(12) United States Patent
Janjic et al.

(10) Patent No.: US 6,426,335 B1
(45) Date of Patent: *Jul. 30, 2002

(54) VASCULAR ENDOTHELIAL GROWTH FACTOR (VEGF) NUCLEIC ACID LIGAND COMPLEXES

(75) Inventors: Nebojsa Janjic; Larry Gold, both of Boulder; Paul Schmidt, Niwot; Chandra Vargeese, Thornton; Michael Willis, Louisville, all of CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,968

(22) PCT Filed: Oct. 17, 1997

(86) PCT No.: PCT/US97/18944

§ 371 (c)(1),
(2), (4) Date: Mar. 13, 2000

(87) PCT Pub. No.: WO98/18480

PCT Pub. Date: May 7, 1998

(51) Int. Cl.$^7$ ........................ A61K 31/70; C07H 21/04; C07H 21/02
(52) U.S. Cl. ........................................ 514/44; 536/23.1
(58) Field of Search .................. 514/44, 23.1; 536/23.1

(56) References Cited

U.S. PATENT DOCUMENTS

| | | | |
|---|---|---|---|
| 4,904,582 A | 2/1990 | Tullis | 435/6 |
| 4,914,210 A | 4/1990 | Levenson et al. | 435/6 |
| 4,962,029 A | 10/1990 | Levenson et al. | 435/6 |
| 4,997,652 A | 3/1991 | Wong | 435/6 |
| 5,149,794 A | 9/1992 | Yatvin et al. | 435/6 |
| 5,245,022 A | 9/1993 | Weis et al. | 435/6 |
| 5,270,163 A | 12/1993 | Gold et al. | 435/6 |
| 5,459,015 A | 10/1995 | Janjic et al. | 435/6 |
| 5,475,096 A | 12/1995 | Gold et al. | 435/6 |
| 5,595,877 A | 1/1997 | Gold et al. | 435/6 |
| 5,659,013 A | 8/1997 | Senger et al. | 435/6 |
| 5,670,633 A | 9/1997 | Cook et al. | 435/6 |
| 5,710,136 A | 1/1998 | Robinson et al. | 435/6 |
| 5,811,533 A | 9/1998 | Gold et al. | 435/6 |
| 6,168,778 B1 * | 1/2001 | Janjic et al. | 424/1.73 |

FOREIGN PATENT DOCUMENTS

| | | |
|---|---|---|
| EP | 0 292 128 A1 | 11/1988 |
| EP | 0 462 145 B1 | 4/1994 |
| WO | WO90/10448 | 9/1990 |
| WO | WO91/14696 | 10/1991 |
| WO | WO92/14843 | 9/1992 |
| WO | WO93/08210 | 4/1993 |
| WO | WO94/01448 | 1/1994 |
| WO | WO94/10202 | 5/1994 |
| WO | WO94/15619 | 7/1994 |
| WO | WO94/27615 | 12/1994 |
| WO | WO94/29479 | 12/1994 |
| WO | WO95/00529 | 1/1995 |
| WO | WO95/06474 | 3/1995 |
| WO | WO95/06659 | 3/1995 |
| WO | WO96/21469 | 7/1996 |
| WO | WO96/30046 | 10/1996 |
| WO | WO96/40062 | 12/1996 |
| WO | WO97/09427 | 3/1997 |

OTHER PUBLICATIONS

Orkin et al. Report and Recommendations of the Panel to Assess the NIH Investment in Research on Gene Therapy, 1995.*
Vieweg et al. Cancer Investigation 13(2):193–201, 1995.*
Jaschke et al. (1994) Nucleic Acids Research 22:4810–4817.
MacKellar et al. (1992) Nucleic Acids Research 20:3411–3417.
Shea et al. (1990) Nucleic Acids Research 18:3777–3783.
Jakeman et al. (1992) J. Clin. Invest. 89:244–252.
Szostak, "Structure and Activity of Ribozymes," in *Redesigning the Molecules of Life*, (S.A. Benner ed.) Springer–Verlag Berlin Heidelberg, pp. 87–113, (1988).

* cited by examiner

*Primary Examiner*—Stephanie Zitomer
(74) *Attorney, Agent, or Firm*—Swanson & Bratschun, LLC

(57) ABSTRACT

This invention discloses a method for preparing a complex comprised of a VEGF Nucleic Acid Ligand and a Non-Immunogenic, High Molecular Weight Compound or Lipophilic Compound by identifying a VEGF Nucleic Acid Ligand by SELEX methodology and associating the VEGF Nucleic Acid Ligand with a Non-Immunogenic, High Molecular Weight Compound or Lipophilic Compound. The invention further discloses Complexes comprising one or more VEGF Nucleic Acid Ligands in association with a Non-Immunogenic, High Molecular Weight Compound or Lipophilic Compound. The invention further includes a Lipid construct comprising a VEGF Nucleic Acid Ligand or Complex and methods for making the same.

23 Claims, 34 Drawing Sheets

NX-213
SEQ ID NO: 1

Ligand =
5'-TsTsTsTsmAaCaCaCaUrGrAaUmAmGrAaCmGaCaCmGmGmGmGaUmGTsTsTsTsT-3'

Structure =

Ligand component =
5'-TsTsTsTsmAaCaCaCaUrGrAaUmGrGaUmAmGrAaCmGaCaCmGmGmGmGaUmGTsTsTsTsT-3'
(VEGF ligand)   SEQ ID NO: 2

Structure =
scNX-278
Ligand component =
5'-TsTsTsTs mGaUaC mGmGaU mAaCrG mGrAmG aUmGrG rAaCaC mGaUaC mAaCmG TsTsTsTsT-3'
(VEGF ligand) SEQ ID NO: 3 scNX-213

Ligand =
5'-TsTsTsTsmGaUaCmGmGaUmAaCrGmGaUmGrGrAaCaCmGaUaCmAaCmGTsTsTsTsT-3'

SEQ ID NO: 4

Ligand Component =
fCmGmGrArAfUfCmAmGfUmGmAmAfUmGfCfUfUmAfUmAfCmAfUfCfCmG-3'3'-dT
(VEGF ligand)   SEQ ID NO: 5

NX31838 Lipid-amide 1

Ligand Component =
fCmGmGrArAfUfCmAmGfUmGmAmAfUmGfCfUfUmAfUmAfCmAfUfCfCmG-3'3'-dT
(VEGF ligand)   SEQ ID NO: 6

NX31838 Lipid-amide 2

Ligand Component = fCmGmGrArAfUfCmAmGfUmGmAmAfUmGfCfUfUmAfUmAfCmAfUfCmG-3'3'-dT (VEGF ligand)  SEQ ID NO: 7

NX31838 40K PEG

Ligand Component = fCmGmGrArAfUfCmAmGfUmGmAmAfUmGfCfUfUmAfUmAfCmAfUfCmG-3'3'-dT (VEGF ligand)  SEQ ID NO: 8

NX31838 20K PEG

Ligand Component = fCmGmGrArAfUfCfUfUmAfCmAfUmGfCfCmG-3′3′-dT
(VEGF ligand) SEQ ID NO: 9

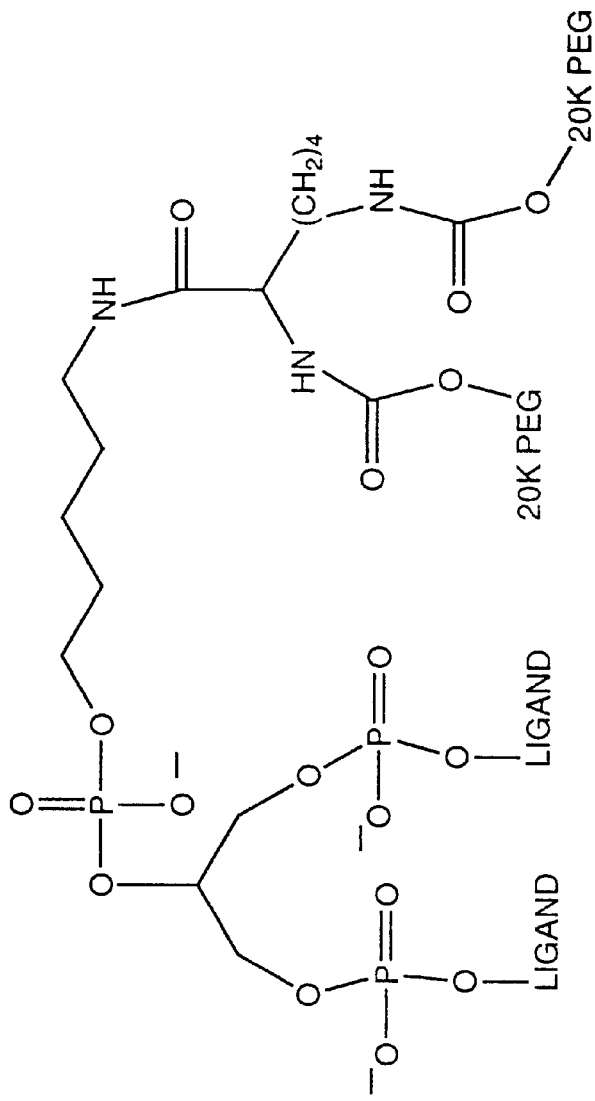
Ligand Component =
fCmGmGrArAfUfCmAfCmAmGfUmGmAmAfUmGfCfUfUmAfUmAfCmAfUfCfCmG-3

Ligand Component =
fCmGmGrArAfUfCmAmGfUmGmAmAfUmGfCfCfUfUmAfCmAfUfCfCmG-3'3'-dT
(VEGF ligand)   SEQ ID NO: 11

FIG. 1L

Ligand Component = fCmGmGrArAfUfCmAmGfUmGmAmAfUmGfCfUfUmAfUmAfCmAfUfCfCmG-3'3'-dT (VEGF ligand)   SEQ ID NO: 12

C-5 Amino linker

Glycerol bisphosphate 18 atom spacer

Ligand Component =
5'-[C5 NH2 link]-fCrAfUfUmAfCmAfCfCmGrAmAmGfUfUmAfCmGfUmGmAmGfUmAfUmG-3'3'dT-3'

SEQ ID NO: 13

Mean Tumor Volume ± SEM

US 6,426,335 B1

VASCULAR ENDOTHELIAL GROWTH FACTOR (VEGF) NUCLEIC ACID LIGAND COMPLEXES

CROSS-REFERENCE TO RELATED APPLICATIONS

This application is a 35 U.S.C. §371 filing of International Application Number PCT/US97/18944, filed Oct. 17, 1997, published as WO 98/18480 on May 7, 1998.

FIELD OF THE INVENTION

Described herein are high affinity 2'Fluoro(2'-F) pyrimidine RNA ligands to vascular endothelial growth factor (VEGF). The method utilized herein for identifying such Nucleic Acid Ligands is called SELEX, an acronym for Systematic Evolution of Ligands by Exponential enrichment. Further included in this invention is a method for preparing a therapeutic or diagnostic Complex comprised of a VEGF Nucleic Acid Ligand and a Non-Immunogenic, High Molecular Weight Compound or a Lipophilic Compound by identifying a VEGF Nucleic Acid Ligand by SELEX methodology and covalently linking the VEGF Nucleic Acid Ligand with a Non-Immunogenic, High Molecular Weight Compound or a Lipophilic Compound. The invention further includes Complexes comprised of one or more VEGF Nucleic Acid Ligands and a Non-Immunogenic, High Molecular Weight Compound or a Lipophilic Compound. The invention further relates to improving the Pharmacokinetic Properties of a VEGF Nucleic Acid Ligand by covalently linking the VEGF Nucleic Acid Ligand with a Non-Immunogenic, High Molecular Weight Compound or Lipophilic Compound to form a Complex. The invention further relates to improving the Pharmacokinetic Properties of a VEGF Nucleic Acid Ligand by using a Lipid Construct comprising a VEGF Nucleic Acid Ligand or a Complex comprising a VEGF Nucleic Acid Ligand and a Non-Immunogenic, High Molecular Weight Compound or Lipophilic Compound. This invention further relates to a method for targeting a therapeutic or diagnostic agent to a biological target that is expressing VEGF by associating the agent with a Complex comprised of a VEGF Nucleic Acid Ligand and a Lipophilic Compound or Non-Immunogenic, High Molecular Weight Compound, wherein the Complex is further associated with a Lipid Construct and the VEGF Nucleic Acid Ligand is further associated with the exterior of the Lipid Construct.

BACKGROUND OF THE INVENTION

A. Selex

The dogma for many years was that nucleic acids had primarily an informational role. Through a method known as Systematic Evolution of Ligands by EXponential enrichment, termed SELEX, it has become clear that nucleic acids have three dimensional structural diversity not unlike proteins. SELEX is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled Method for Indentifying, "Nucleic Acid Ligands," now U.S. Pat. No. 5,270,163 (see also WO 91/19813), each of which is specifically incorporated by reference herein. Each of these applications, collectively referred to herein as the SELEX Patent Applications, describes a fundamentally novel method for making a Nucleic Acid Ligand to any desired target molecule. The SELEX process provides a class of products which are referred to as Nucleic Acid Ligands, each ligand having a unique sequence, and which has the property of binding specifically to a desired target compound or molecule. Each SELEX-identified Nucleic Acid Ligand is a specific ligand of a given target compound or molecule. SELEX is based on the unique insight that Nucleic Acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the target under conditions favorable for binding, partitioning unbound Nucleic Acids from those Nucleic Acids which have bound specifically to target molecules, dissociating the Nucleic Acid-target complexes, amplifying the Nucleic Acids dissociated from the Nucleic Acid-target complexes to yield a ligand-enriched mixture of Nucleic Acids, then reiterating the steps of binding, partitioning, dissociating and amplifying through as many cycles as desired to yield highly specific high affinity Nucleic Acid Ligands to the target molecule.

It has been recognized by the present inventors that the SELEX method demonstrates that Nucleic Acids as chemical compounds can form a wide array of shapes, sizes and configurations, and are capable of a far broader repertoire of binding and other functions than those displayed by Nucleic Acids in biological systems.

The present inventors have recognized that SELEX or SELEX-like processes could be used to identify Nucleic Acids which can facilitate any chosen reaction in a manner similar to that in which Nucleic Acid Ligands can be identified for any given target. In theory, within a Candidate Mixture of approximately $10^{13}$ to $10^{18}$ Nucleic Acids, the present inventors postulate that at least one Nucleic Acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific Nucleic Acid Ligands able to discriminate between closely related molecules, which can be non-peptidic, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588, describes a SELEX-based method which achieves highly efficient partitioning between oligonucleotides having high and low affinity for a target molecule.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nuceosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Complexes." VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes." VEGF Nucleic Acid Ligands that are associated with a High Molecular Weight, Non-Immunogenic Compound, such as Polyethylene glycol or a Lipophilic Compound, such as Glycerolipid, phospholipid, or glycerol amide lipid, in a diagnostic or therapeutic complex are described in U.S. patent application Ser. No. 08/897,351, filed Jul. 21, 1997, entitled "Vascular Endothelial Growth Factor (VEGF) Nucleic Acid Complexes." Each of the above described patent applications which describe modifications of the basic SELEX procedure are specifically incorporated by reference herein in their entirety.

B. Lipid Constructs

Lipid Bilayer Vesicles are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline or other polar groups. Examples of lipophilic groups are saturated or unsaturated hydrocarbons such as alkyl, alkenyl or other lipid groups. Sterols (e.g., cholesterol) and other pharmaceutically acceptable adjuvants (including antioxidants like alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into small or Unilamellar Vesicles (UV), with the application of a shearing force.

The therapeutic use of liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. Antibodies are known to have a high specificity for their corresponding antigen and have been attached to the surface of liposomes, but the results have been less than successful in many instances. Some efforts, however, have been successful in targeting liposomes to tumors without the use of antibodies, see, for example, U.S. Pat. Nos. 5,019,369, 5,441,745, or 5,435,989.

An area of development aggressively pursued by researchers is the delivery of agents not only to a specific cell type but into the cell's cytoplasm and, further yet, into the nucleus. This is particularly important for the delivery of biological agents such as DNA, RNA, ribozymes and proteins. A promising therapeutic pursuit in this area involves the use of antisense DNA and RNA oligonucleotides for the treatment of disease. However, one major problem encountered in the effective application of antisense technology is that oligonucleotides in their phosphodiester form are quickly degraded in body fluids and by intracellular and extracellular enzymes, such as endonucleases and exonucleases, before the target cell is reached. Intravenous administration also results in rapid clearance from the bloodstream by the kidney, and uptake is insufficient to produce an effective intracellular drug concentration. Liposome encapsulation protects the oligonucleotides from the degradative enzymes, increases the circulation half-life and increases uptake efficiency as a result of phagocytosis of the Liposomes. In this way, oligonucleotides are able to reach their desired target and to be delivered to cells in vivo.

A few instances have been reported where researchers have attached antisense oligonucleotides to Lipophilic Compounds or Non-Immunogenic, High Molecular Weight Compounds. Antisense oligonucleotides, however, are only effective as intracellular agents. Antisense oligodeoxyribonucleotides targeted to the epidermal growth factor (EGF) receptor have been encapsulated into Liposomes linked to folate via a polyethylene glycol spacer (folate-PEG-Liposomes) and delivered into cultured KB cells via folate receptor-mediated endocytosis (Wang et al. (1995) Proc. Natl. Acad. Sci USA 92:3318–3322). In addition, alkylene diols have been attached to oligonucleotides (Weiss et al., U.S. Pat. No. 5,245,022). Furthermore, a Lipophilic Compound covalently attached to an antisense oligonucleotide has been demonstrated in the literature (EP 462 145 B1).

Loading of biological agents into liposomes can be accomplished by inclusion in the lipid formulation or loading into preformed liposomes. Passive anchoring of oligopeptide and oligosaccharide ligands to the external surface of liposomes has been described (Zalipsky et al. (1997) Bioconjug. Chem. 8:111:118).

C. VEGF

The growth of new blood vessels from existing endothelium (angiogenesis) is tightly controlled in healthy adults by opposing effects of positive and negative regulators. Under certain pathological conditions, including proliferative retinopathies, rheumatoid arthritis, psoriasis and cancer, positive regulators prevail and angiogenesis contributes to disease progression (reviewed in Folkman (1995) Nature Medicine 1:27–31). In cancer, the notion that angiogenesis represents the rate limiting step of tumor growth and metastasis (Folkman (1971) New Engl. J. Med. 285:1182–1186) is now supported by considerable experimental evidence (reviewed in Aznavoorian et al. (1993) Cancer 71:1368–1383; Fidler and Ellis (1994) Cell 79:185–188; Folkman (1990) J. Natl. Cancer Inst. 82:4–6).

The quantity of blood vessels in tumor tissue is a strong negative prognostic indicator in breast cancer (Weidner et al. (1992) J. Natl. Cancer Inst. 84:1875–1887), prostate cancer (Weidner et al. (1993) Am. J. Pathol. 143:401–409), brain tumors (Li et al.(1994) Lancet 344:82–86), and melanoma (Foss et al.(1996) Cancer Res. 56:2900–2903).

A number of angiogenic growth factors have been described to date among which vascular endothelial growth factor (VEGF) appears to play a key role as a positive regulator of physiological and pathological angiogenesis (reviewed in Brown et al.(1996) Control of Angiogenesis (Goldberg and Rosen, eds.) Birkhauser, Basel, in press; Thomas (1996) J. Biol. Chem. 271:603–606). VEGF is a secreted disulfide-linked homodimer that selectively stimulates endothelial cells to proliferate, migrate, and produce matrix-degrading enzymes (Conn et al.(1990) Proc. Natl. Acad. Sci. USA 87:1323–1327); Ferrara and Henzel (1989) Biochem. Biophys. Res. Commun. 161:851–858); Gospodarowiczet al.(1989) Proc. Natl. Acad. Sci. USA 7311–7315); Pepper et al.(1991) Biochem. Biophys. Res. Commun. 181:902–906; Unemori et al.(1992) J. Cell. Physiol. 153:557–562), all of which are processes required for the formation of new vessels. In addition to being the only known endothelial cell specific mitogen, VEGF is unique among angiogenic growth factors in its ability to induce a transient increase in blood vessel permeability to macromolecules (hence its original and alternative name, vascular permeability factor, VPF) (Dvorak et al.(1979) J. Immunol. 122:166–174; Senger et al.(1983) Science 219:983–985; Senger et al.(1986) Cancer Res. 46:5629–5632). Increased vascular permeability and the resulting deposition of plasma proteins in the extravascular space assists the new vessel formation by providing a provisional matrix for the migration of endothelial cells (Dvorak et al.(1995) Am. J. Pathol. 146:1029–1039). Hyperpermeability is indeed a characteristic feature of new vessels, including those associated with tumors (Dvorak et al.(1995) Am. J. Pathol. 146:1029–1039). Furthermore, compensatory angiogenesis induced by tissue hypoxia is now known to be mediated by VEGF (Levy et al.(1996) J. Biol. Chem. 2746–2753); Shweiki et al. (1992) Nature 359:843–845).

VEGF occurs in four forms (VEGF-121, VEGF-165, VEGF-189, VEGF-206) as a result of alternative splicing of the VEGF gene (Houck et al. (1991) Mol. Endocrin. 5:1806–1814; Tischer et al. (1991) J. Biol. Chem. 266:11947–11954). The two smaller forms are diffusable while the larger two forms remain predominantly localized to the cell membrane as a consequence of their high affinity for heparin. VEGF-165 also binds to heparin and is the most abundant form. VEGF-121, the only form that does not bind to heparin, appears to have a lower affinity for the receptors (Gitay-Goren et al. (1996) J. Biol. Chem. 271:5519–5523) as well as lower mitogenic potency (Keyt et al. (1996) J. Biol. Chem. 271:7788–7795). The biological effects of VEGF are mediated by two tyrosine kinase receptors (Flt-1 and Flk-1/KDR) whose expression is highly restricted to cells of endothelial origin (de Vries et al. (1992) Science 255:989–991; Millauer et al. (1993) Cell 72:835–846; Terman et al. (1991) Oncogene 6:519–524). While the expression of both functional receptors is required for high affinity binding, the chemotactic and mitogenic signaling in endothelial cells appears to occur primarily through the KDR receptor (Park et al. (1994) J. Biol. Chem. 269:25646–25654; Seetharam et al. (1995) Oncogene 10:135–147; Waltenberger et al. (1994) J. Biol. Chem. 26988–26995). The importance of VEGF and VEGF receptors for the development of blood vessels has recently been demonstrated in mice lacking a single allele for the VEGF gene (Carmeliet et al. (1996) Nature 380:435–439; Ferrara et al. (1996) Nature 380:439–442) or both alleles of the Flt-1 (Fong et al. (1995) 376:66–70) or Flk-1 genes (Shalaby et al. (1995) Nature 376:62–66). In each case, distinct abnormalities in vessel formation were observed resulting in embryonic lethality.

VEGF is produced and secreted in varying amounts by virtually all tumor cells (Brown et al. (1997) Regulation of Angiogenesis (Goldberg and Rosen, Eds.) Birkhauser, Basel, pp.233–269). Direct evidence that VEGF and its receptors contribute to tumor growth was recently obtained by a demonstration that the growth of human tumor xenografts in nude mice could be inhibited by neutralizing antibodies to VEGF (Kim et al. (1993) Nature 362:841–844), by the expression of dominant-negative VEGF receptor flk-1 (Millauer et al. (1996) Cancer Res. 56:1615–1620; Millauer et al. (1994) Nature 367:576–579), by low molecular weight inhibitors of Flk-1 tyrosine kinase activity (Strawn et al. (1966) Cancer Res. 56:3540–3545), or by the expression of antisense sequence to VEGF mRNA (Saleh et al. (1996) Cancer Res. 56:393–401). Importantly, the incidence of tumor metastases was also found to be dramatically reduced by VEGF antagonists (Claffey et al. (1996) Cancer Res. 56:172–181).

In addition to their use as anticancer agents, VEGF inhibitors may be useful in a wide variety of proliferative diseases characterized by excessive angiogenesis, including psoriasis, ocular disorders, collagen vascular diseases and rheumatoid arthritis. Although most tumor types are known to produce VEGF, until recently none has been shown to express functional VEGF receptors. It has been shown that Kaposi's Sarcoma (KS) cells not only produce abundant amounts of VEGF but also express functional VEGF receptors and therefore use VEGF for autocrine growth. Kaposi's sarcoma is typically treated with conventional antimetabolic drugs. However, a major shortcoming of the use of chemotherapy in KS patients is the accompanying induction of immunosuppression which has serious consequences in patients whose immune system is already compromised. The need for alternative therapies is especially great in early stages of the disease where KS lesions begin to appear but the patients otherwise feel fairly healthy. In this regard, encapsulation of chemotherapeutic drugs such as daunorubicin into liposomes has recently proved to be a promising method of minimizing side effects of chemotherapy while maintaining anti-tumor efficacy. Drugs with low toxicity that selectively target activated cells of endothelial origin, such as the Nucleic Acid Ligand VEGF antagonists described here, would be an enormous asset in the treatment of KS.

Other areas of potential clinical utility for the VEGF Nucleic Acid Ligands are ocular disorders characterized by excessive angiogenesis. Examples of such diseases are macular degeneration and diabetic retinopathy. In macular degeneration, progressive choroidal angiogenesis beneath the macula (a part of the retina responsible for the highest visual acuity) interferes with vision. In diabetic retinopathy, angiogenesis in the retina interferes with vision. While the initial stimuli that initiate blood vessel growth in macular degeneration and diabetic retinopathy are not known at present, VEGF appears to be a key angiogenesis inducer (Lopez, P. F. et al. (1996) Invest. Ophthalmol. Visual Science 37, 855–868; Kliffen, M. et al. (1997) Br. J. Ophthalmol. 81, 154–162; Kvanta, A. et al. (1996) Invest. Ophthalmol. Visual Science 37, 1929–1934; Paques et al. (1997) Diabetes & Metabolism 23:125–130). Inhibitors of VEGF therefore may be useful in attenuating angiogenesis in macular degeneration.

SUMMARY OF THE INVENTION

Described herein are high affinity 2' Fluoro (2'-F)-modifiedpyrimidine RNA ligands to vascular endothelial growth factor (VEGF). The method utilized herein for identifying such nucleic acid ligands is called SELEX, an acronym for Systematic Evolution of Ligands by Exponential enrichment. The ligands described herein were selected from an initial pool of about $10^{14}$ RNA molecules randomized at 30 or 40 contiguous positions. Included herein are the evolved ligands that are shown in Tables 2–6. Further included in this invention is a method for preparing a Complex comprised of a VEGF Nucleic Acid Ligand and a Non-Immunogenic, High Molecular Weight Compound or Lipophilic Compound by the method comprising identifying a Nucleic Acid Ligand from a Candidate Mixture of Nucleic Acids where the Nucleic Acid is a ligand of VEGF by the method of (a) contacting the Candidate Mixture of Nucleic Acids with VEGF, (b) partitioning between members of said Candidate Mixture on the basis of affinity to VEGF, and c) amplifying the selected molecules to yield a mixture of Nucleic Acids enriched for Nucleic Acid sequences with a relatively higher affinity for binding to VEGF, and covalently linking said identified VEGF Nucleic Acid Ligand with a Non-Immunogenic, High Molecular Weight Compound or a Lipophilic Compound. The invention further comprises a Complex comprised of a VEGF Nucleic Acid Ligand and a Non-Immunogenic, High Molecular Weight Compound or a Lipophilic Compound.

The invention further includes a Lipid Construct comprising a VEGF Nucleic Acid Ligand or a Complex. The present invention further relates to a method for preparing a Lipid Construct comprising a Complex wherein the Complex is comprised of a VEGF Nucleic Acid Ligand and a Lipophilic Compound.

In another embodiment, this invention provides a method for improving the pharmacokinetic properties of a VEGF Nucleic Acid Ligand by covalently linking the VEGF Nucleic Acid Ligand with a Non-Immunogenic, High Molecular Weight Compound or Lipophilic Compound to form a Complex and administering the Complex to a patient. The invention further relates to a method for improving the pharmacokinetic properties of a VEGF Nucleic Acid Ligand by further associating the Complex with a Lipid Construct.

It is an object of the present invention to provide Complexes comprising one or more VEGF Nucleic Acid Ligands in association with one or more Non-Immunogenic, High Molecular Weight Compounds or Lipophilic Compounds and methods for producing the same. It is a further object of the present invention to provide Lipid Constructs comprising a Complex. It is a further object of the invention to provide one or more VEGF Nucleic Acid Ligands in association with one or more Non-Immunogenic, High Molecular Weight Compounds or Lipophilic Compounds with improved Pharmacokinetic Properties.

In embodiments of the invention directed to Complexes comprised of a VEGF Nucleic Acid Ligand and a Non-Immunogenic, High Molecular Weight Compound, it is preferred that the Non-Immunogenic, High Molecular Weight Compound is Polyalkylene Glycol, more preferably, polyethylene glycol (PEG). More preferably, the PEG has a molecular weight of about 10–80K. Most preferably, the PEG has a molecular weight of about 20–45K. In embodiments of the invention directed to Complexes comprised of a VEGF Nucleic Acid Ligand and a Lipophilic Compound, it is preferred that the Lipophilic Compound is a glycerolipid. In the preferred embodiments of the invention, the Lipid Construct is preferably a Lipid Bilayer Vesicle and most preferably a Liposome. In the preferred embodiment, the VEGF Nucleic Acid Ligand is identified according to the SELEX method.

In embodiments of the invention directed to Complexes comprising a Non-Immunogenic, High Molecular Weight Compound or Lipophilic Compound covalently linked to a VEGF Nucleic Acid Ligand or Ligands, the VEGF Nucleic Acid Ligand or Ligands can serve in a targeting capacity.

Additionally, the VEGF Nucleic Acid Ligand can be associated through Covalent or Non-Covalent Interactions with a Lipid Construct without being part of a Complex.

Furthermore, in embodiments of the invention directed to Lipid Constructs comprising a VEGF Nucleic Acid Ligand or a Non-Immunogenic, High Molecular Weight or Lipophilic Compound/VEGF Nucleic Acid Ligand Complex where the Lipid Construct is of a type that has a membrane defining an interior compartment such as a Lipid Bilayer Vesicle, the VEGF Nucleic Acid Ligand or Complex in association with the Lipid Construct may be associated with the membrane of the Lipid Construct or encapsulated within the compartment. In embodiments where the VEGF Nucleic Acid Ligand is in association with the membrane, the VEGF Nucleic Acid Ligand can associate with the interior-facing or exterior-facing part of the membrane such that the VEGF Nucleic Acid Ligand is projecting into or out of the vesicle. In certain embodiments, a VEGF Nucleic Acid Ligand Complex can be passively loaded onto the outside of a preformed Lipid Construct. In embodiments where the Nucleic Acid Ligand is projecting out of the Lipid Construct, the VEGF Nucleic Acid Ligand can serve in a targeting capacity.

In embodiments where the VEGF Nucleic Acid Ligand of the Lipid Construct serves in a targeting capacity, the Lipid Construct can have associated with it additional therapeutic or diagnostic agents. In one embodiment, the therapeutic or diagnostic agent is associated with the exterior of the Lipid Construct. In other embodiments, the therapeutic or diagnostic agent is encapsulated in the Lipid Construct or associated with the interior of the Lipid Construct. In yet a further embodiment, the therapeutic or diagnostic agent is associated with the Complex. In one embodiment, the therapeutic agent is a drug. In an alternative embodiment, the therapeutic or diagnostic agent is one or more additional Nucleic Acid Ligands.

It is a further object of the present invention to provide a method for inhibiting angiogenesis by the administration of a VEGF Nucleic Acid Ligand or a Complex comprising a VEGF Nucleic Acid Ligand and Non-Immunogenic, High Molecular Weight Compound or Lipophilic Compound or a Lipid Construct comprising the Complex of the present invention. It is yet a further object of the present invention to provide a method for inhibiting the growth of tumors by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention. It is yet a further object of the invention to provide a method for inhibiting Kaposi's Sarcoma by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention. It is yet a further object of the invention to provide a method for inhibiting macular degeneration by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention. It is yet a further object of the invention to provide a method for inhibiting diabetic retinopathy by the administration of a VEGF Nucleic Acid Ligand or Complex comprising a VEGF Nucleic Acid Ligand and Non-Immunogenic, High Molecular Weight Compound or Lipophilic Compound or a Lipid Construct comprising a Complex of the present invention.

It is a further object of the invention to provide a method for targeting a therapeutic or diagnostic agent to a biological target that is expressing VEGF by associating the agent with a Complex comprised of a VEGF Nucleic Acid Ligand and a Lipophilic Compound or Non-Immunogenic, High Molecular Weight Compound, wherein the Complex is further associated with a Lipid Construct and the VEGF Nucleic Acid Ligand is further associated with the exterior of the Lipid Construct.

These and other objects, as well as the nature, scope and utilization of this invention, will become readily apparent to those skilled in the art from the following description and the appended claims.

DETAILED DESCRIPTION OF THE INVENTION

DEFINITIONS

Figure 1B:
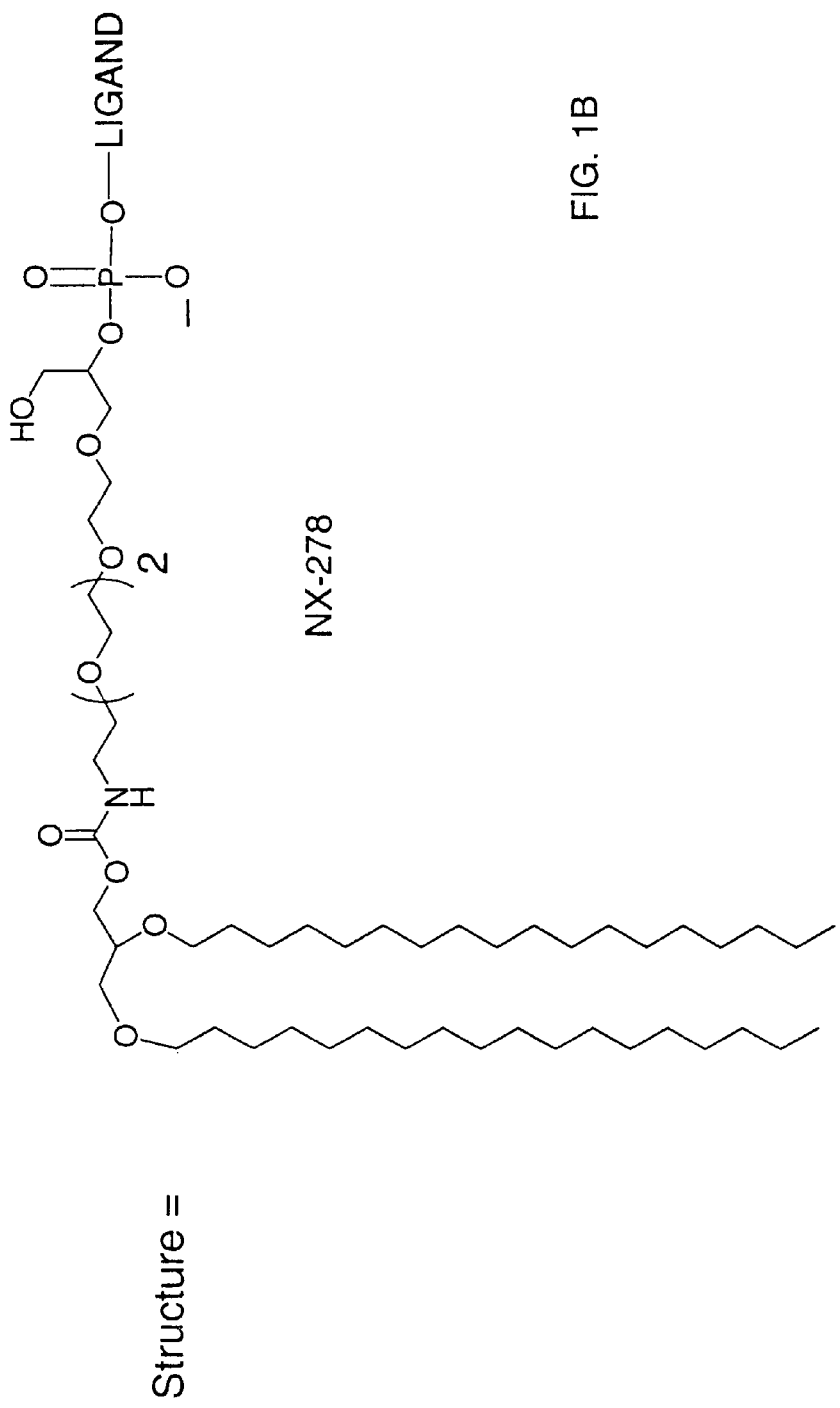
FIGS. 1A–1R show the molecular descriptions of NX213 (FIG. 1A), NX278 (FIG. 1B), scNX278 (FIG. 1C), scNX213 (FIG. 1D), NX31838-PL(FIG. 1E), NX31838 Lipid Amide 1 (FIG. 1F), NX31838 Lipid Amide 2 (FIG. 1G), NX31838-40K PEG (FIG. 1H), NX31838-20K PEG (FIG. 1I), NX31838 40K PEG dimer with no linker (NX31838d0) (FIG. 1J), NX31838 40K dimer with one C5 linker (NX31838d1) (FIG. 1K), NX31838 40K PEG dimer with two C5 linkers (NX31838d2) (FIG. 1L), C-5 Aminolinker (FIG. 1M), Glycerol Bisphosphate Linker (FIG. 1N), 18 Atom Spacer Linker (FIG. 1O), Aminotetraethylene Glycol Linker (FIG. 1P), 3'3' dT (FIG. 1Q), and NX31917 (FIG. 1R). The 5' phosphate group of the ligand is depicted in the figures, mPEG stands for methyl polyethylene glycol. A lower case letter preceding a nucleotide indicates the following: m=2'-O-Methyl, a=2'-amino, r=ribo, and f=2'-fluoro. No letter preceding a nucleotide indicates a deoxyribonucleotide(2'H). 3'3'-dT indicates a 3'3' inverted phosphodiesterlinkage at the 3' end. An S following a nucleotide denotes a backbone modification consisting of a phosphorothioate internucleoside linkage.
Figure 1C:
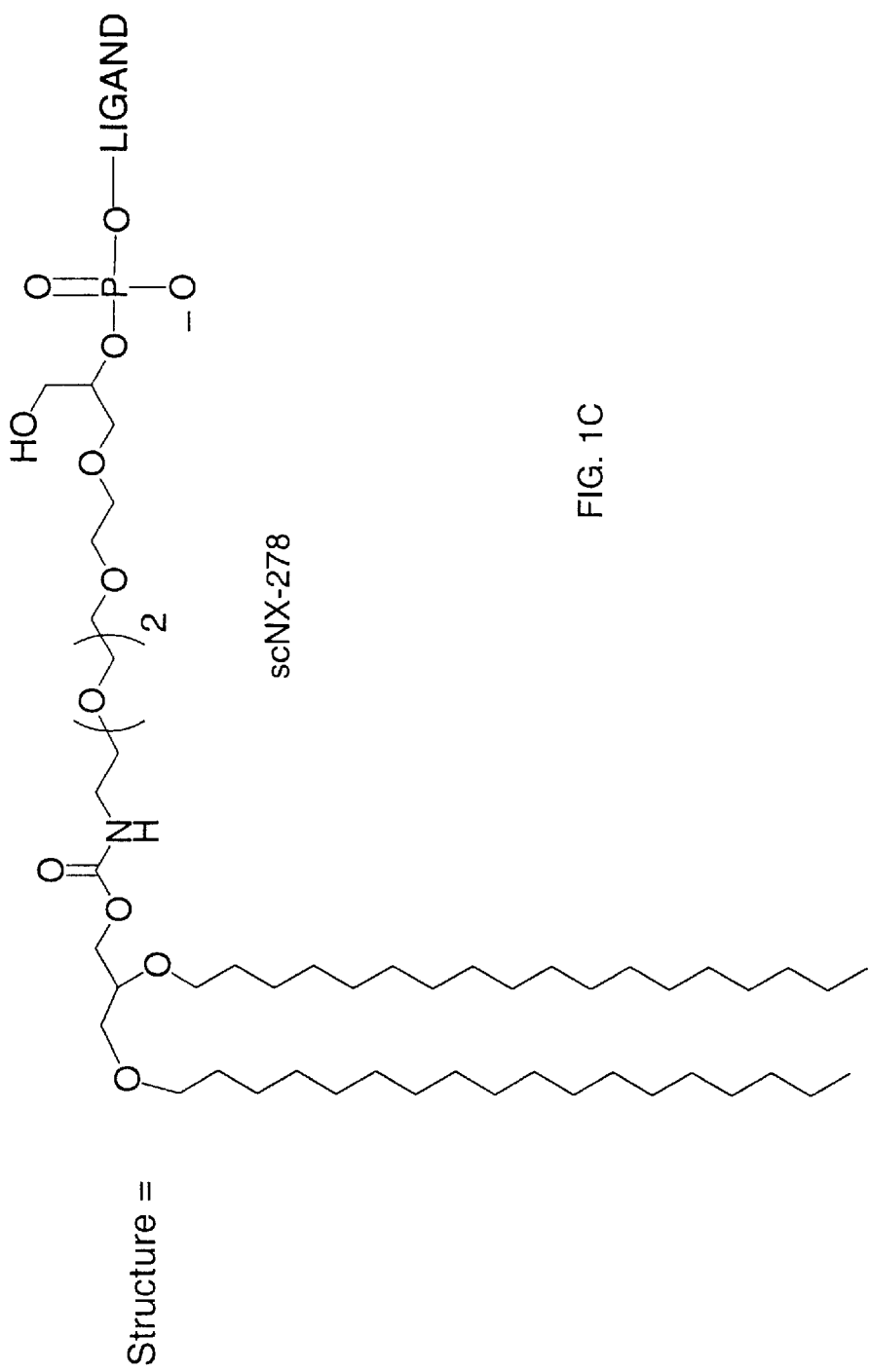

"Covalent Bond" is the chemical bond formed by the sharing of electrons.

"Non-Covalent Interactions" are means by which molecular entities are held together by interactions other than Covalent Bonds including ionic interactions and hydrogen bonds.

"Lipophilic Compounds" are compounds which have the propensity to associate with or partition into lipid and/or other materials or phases with low dielectric constants, including structures that are comprised substantially of lipophilic components. Lipophilic Compounds include lipids as well as non-lipid containing compounds that have the propensity to associate with lipid (and/or other materials or phases with low dielectric constants). Cholesterol, phospholipid, and glycerolipids, such as dialkylglycerol, and diacylglycerol, and glycerol amide lipids are further examples of Lipophilic Compounds. In one preferred embodiment of the invention, the lipophilic compound covalently linked to the VEGF Nucleic Acid Ligand is a glycerolipid having the structure

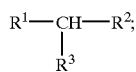

where $R^1$, $R^2$, and $R^3$ are independently selected from the group consisting of $CH_3(CH)_n$—$O(PO_3)$—$CH_2$—; and $CH_3(CH_2)_n$—$CONH_2$—$CH_2$—, $CH_3(CH_2)_nO$—, $CH_3(CH_2)_nOCH_2$—, $CH_3(CH_2)_n(CO)OCH_2$—, $CH_3(CH_2)_n(CO)O$— and X—, wherein at least one must be X—, and X is independently selected from the group consisting of $(PO_4)$, O and $CH_2OC$=$O$, and wherein n=0–30, preferably 10–20. When R is $CH_3(CH_2)_n$—$O(PO_3)$—$CH_2$—, the Lipophilic Compound is a phospholipid. When R is $CH_3(CH_2)_n$—$CONH_2$—$CH_2$—, the Lipophilic Compound is a glycerol amide lipid. When R is $CH_3(CH_2)_nO$— or $CH_3(CH_2)_nOCH_2$—, the Lipophilic Compound is a dialkylglycerollipid. When R is $CH_3(CH_2)_n(CO)OCH_2$— or $CH_3(CH_2)_n(CO)O$—; the Lipophilic Compound is diacylglycerol lipid. In a preferred embodiment, $R^3$ is X—.

"Complex" as used herein describes the molecular entity formed by the covalent linking of a VEGF Nucleic Acid Ligand to a Non-Immunogenic, High Molecular Weight Compound or Lipophilic Compound. In certain embodiments of the present invention, the Complex is depicted as A-B-Y, wherein A is a Lipophilic Compound or Non-Immunogenic, High Molecular Weight Compound as described herein; B is optional, and may be one or more linkers Z; and Y is a VEGF Nucleic Acid Ligand.

"Lipid Constructs," for purposes of this invention, are structures containing lipids, phospholipids, or derivatives thereof comprising a variety of different structural arrangements which lipids are known to adopt in aqueous suspension. These structures include, but are not limited to, Lipid Bilayer Vesicles, micelles, Liposomes, emulsions, lipid ribbons or sheets, and may be complexed with a variety of drugs and components which are known to be pharmaceutically acceptable. In the preferred embodiment, the Lipid Construct is a Liposome. The preferred Liposome is unilarnellar and has a relative size less than 200 nm. Common additional components in Lipid Constructs include cholesterol and alpha-tocopherol, among others. The Lipid Constructs may be used alone or in any combination which one skilled in the art would appreciate to provide the characteristics desired for a particular application. In addition, the technical aspects of Lipid Constructs and Liposome formation are well known in the art and any of the methods commonly practiced in the field may be used for the present invention.

"Nucleic Acid Ligand" as used herein is a non-naturally occurring Nucleic Acid having a desirable action on a Target. The Target of the present invention is VEGF, hence the term VEGF Nucleic Acid Ligand. A desirable action includes, but is not limited to, binding of the Target, catalytically changing the Target, reacting with the Target in a way which modifies/alters the Target or the functional activity of the Target, covalently attaching to the Target as in a suicide inhibitor, facilitating the reaction between the Target and another molecule. In the preferred embodiment, the action is specific binding affinity for VEGF, wherein the Nucleic Acid Ligand is not a Nucleic Acid having the known physiological function of being bound by VEGF.

In preferred embodiments of the invention, the VEGF Nucleic Acid Ligand of the Complexes and Lipid Constructs of the invention are identified by the SELEX methodology. VEGF Nucleic Acid Ligands are identified from a Candidate Mixture of Nucleic Acids, said Nucleic Acid being a ligand of VEGF, by the method comprising a) contacting the Candidate Mixture with VEGF, wherein Nucleic Acids having an increased affinity to VEGF relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids (see U.S. patent application Ser. No. 08/233,012, filed Apr. 25, 1994, entitled "High Affinity Oligonucleotides to Vascular Endothelial Growth Factor (VEGF)," U.S. patent application Ser. No. 08/447,169, filed May 19, 1995, entitled "High Affinity Oligonucleotide Ligands to Vascular Endothelial Growth Factor (VEGF)," which are hereby incorporated by reference herein).

"Candidate Mixture" is a mixture of Nucleic Acids of differing sequence from which to select a desired ligand. The source of a Candidate Mixture can be from naturally-occuring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications such as internucleoside phosphorothioate linkages, methylations, unusual base-pairing combinations such as the isobases isocytidine and isoguanidine and the like. Modifications can also include 3' and 5' modifications such as capping.

"Non-Immunogenic, High Molecular Weight Compound" is a compound between approximately 1000 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. Examples of Non-Immunogenic, High Molecular Weight Compounds include Polyalkylene Glycol and polyethylene glycol. In one preferred embodiment of the invention, the Non-Immunogenic, High Molecular Weight Compound covalently linked to the VEGF Nucleic Acid Ligand is a polyalkylene glycol and has the structure R(O(CH$_2$)$_x$)$_n$O—, where R is independently selected from the group consisting of H and CH$_3$, x=2–5, and n≈MW of the Polyalkylene Glycol/16+14x. In the preferred embodiment of the present invention, the molecular weight is about between 10–80 kDa. In the most preferred embodiment, the molecular weight of the polyalkylene glycol is about between 20–45 kDa. In the most preferred embodiment, x=2 and n=9×10$^2$. There can be one or more Polyalkylene Glycols attached to the same VEGF Nucleic Acid Ligand, with the sum of the molecular weights preferably being between 10–80 kDa, more preferably 20–45 kDa. In certain embodiments, the Non-Immunogenic, High Molecular Weight Compound can also be a Nucleic Acid Ligand.

"Lipid Bilayer Vesicles" are closed, fluid-filled microscopic spheres which are formed principally from individual molecules having polar (hydrophilic) and non-polar (lipophilic) portions. The hydrophilic portions may comprise phosphato, glycerylphosphato,carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable components (including anti-oxidants like alpha-tocopherol) may also be included to improve vesicle stability or confer other desirable characteristics.

"Liposomes" are a subset of Lipid Bilayer Vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into unilamellar vesicles (UV), with the application of a shearing force.

"Cationic Liposome" is a Liposome that contains lipid components that have an overall positive charge at physiological pH.

"SELEX" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. The SELEX methodology is described in the SELEX Patent Applications.

"Target" means any compound or molecule of interest for which a ligand is desired. A Target can be a protein (such as VEGF, thrombin, and selectin), peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. The principal Target of the subject invention is VEGF.

"Improved Pharmacokinetic Properties" means that the VEGF Nucleic Acid Ligand covalently linked to a Non-Immunogenic, High Molecular Weight Compound or Lipophilic Compound or in association with a Lipid Construct shows a longer circulation half-life in vivo relative to the same VEGF Nucleic Acid Ligand not in association with a Non-Immunogenic, High Molecular Weight Compound or Lipophilic Compound or in association with a Lipid Construct.

"Linker" is a molecular entity that connects two or more molecular entities through Covalent Bond or Non-Covalent Interactions, and can allow spatial separation of the molecular entities in a manner that preserves the functional properties of one or more of the molecular entities. A linker can also be known as a spacer. Examples of Linkers, include but are not limited to, the structures shown in FIGS. 1M–1P.

"Therapeutic" as used herein, includes treatment and/or prophylaxis. When used, Therapeutic refers to humans and other animals.

This invention includes RNA ligands to VEGF that are comprised of 2'F-modified nucleotides. This invention further includes the specific RNA ligands to VEGF shown in Tables 2–6 (SEQ ID NOS:15–132). More specifically, this invention includes nucleic acid sequences that are substantially homologous to and that have substantially the same ability to bind VEGF as the specific nucleic acid ligands shown in Tables 2–6. By substantially homologous it is meant a degree of primary sequence homology in excess of 70%, most preferably in excess of 80%, and even more preferably in excess of 90%, 95%, or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. Substantially the same ability to bind VEGF means that the affinity is within one or two orders of magnitude of the affinity of the ligands described herein. It is well within the skill of those of ordinary skill in the art to determine whether a given sequence—substantially homologous to those specifically described herein—has the same ability to bind VEGF.

A review of the sequence homologies of the nucleic acid ligands of VEGF shown in Tables 2–6 (SEQ ID NOS:15–132) shows that sequences with little or no primary homology may have substantially the same ability to bind VEGF. For these reasons, this invention also includes Nucleic Acid Ligands that have substantially the same postulated structure or structural motifs and ability to bind VEGF as the nucleic acid ligands shown in Tables 2–6. Substantially the same structure or structural motifs can be postulated by sequence alignment using the Zukerfold program (see Zuker (1989) Science 244:48–52). As would be known in the art, other computer programs can be used for predicting secondary structure and strutural motifs. Substantially the same structure or structural motif of Nucleic Acid Ligands in solution or as a bound structure can also be postulated using NMR or other techniques as would be known in the art.

Further included in this invention is a method for preparing a Complex comprised of a VEGF Nucleic Acid Ligand and a Non-Immunogenic, High Molecular Weight Compound or Lipophilic Compound by the method comprising identifying a Nucleic Acid Ligand from a Candidate Mixture of Nucleic Acids where the Nucleic Acid is a ligand of VEGF by the method of (a) contacting the Candidate Mixture of Nucleic Acids with VEGF, (b) partitioning between members of said Candidate Mixture on the basis of affinity to VEGF, and c) amplifying the selected molecules to yield a mixture of Nucleic Acids enriched for Nucleic Acid sequences with a relatively higher affinity for binding to VEGF, and covalently linking said identified VEGF Nucleic Acid Ligand with a Non-Immunogenic, High Molecular Weight Compound or a Lipophilic Compound.

It is a further object of the present invention to provide Complexes comprising one or more VEGF Nucleic Acid Ligands covalently linked to a Non-Immunogenic, High Molecular Weight Compound or Lipophilic Compound. Such Complexes have one or more of the following advantages over a VEGF Nucleic Acid Ligand not in association with a Non-Immunogenic, High Molecular Weight Compound or Lipophilic Compound: 1) Improved Pharmacokinetic Properties, and 2) improved capacity for intracellular delivery, or 3) improved capacity for targeting. Complexes further associated with a Lipid Construct have the same advantages.

The Complexes or the Lipid Constructs comprising the VEGF Nucleic Acid Ligand or Complexes may benefit from one, two, or three of these advantages. For example, a Lipid Construct of the present invention may be comprised of a) a Liposome, b) a drug that is encapsulated within the interior of the Liposome, and c) a Complex comprised of a VEGF Nucleic Acid Ligand and Lipophilic Compound, wherein the VEGF Nucleic Acid Ligand component of the Complex is associated with and projecting from the exterior of the Lipid Construct. In such a case, the Lipid Construct comprising a Complex will 1) have Improved Pharmacokinetic Properties, 2) have enhanced capacity for intracellular delivery of the encapsulated drug, and 3) be specifically targeted to the preselected location in vivo that is expressing VEGF by the exteriorly associated VEGF Nucleic Acid Ligand.

In another embodiment, this invention provides a method for improving the pharmacokinetic properties of a VEGF Nucleic Acid Ligand by covalently linking the VEGF Nucleic Acid Ligand with a Non-Immunogenic, High Molecular Weight Compound or Lipophilic Compound to form a Complex and administering the Complex to a patient. The invention further relates to a method for improving the pharmacokinetic properties of a VEGF Nucleic Acid Ligand by further associating the Complex with a Lipid Construct.

In another embodiment, the Complex of the present invention is comprised of a VEGF Nucleic Acid Ligand covalently attached to a Lipophilic Compound, such as a glycerolipid, or a Non-Immunogenic, High Molecular Weight Compound, such as Polyalkylene Glycol or polyethylene glycol (PEG). In these cases, the pharmacokinetic properties of the Complex will be enhanced relative to the VEGF Nucleic Acid Ligand alone. In another embodiment, the pharmacokinetic properties of the VEGF Nucleic Acid Ligand is enhanced relative to the VEGF Nucleic Acid Ligand alone when the VEGF Nucleic Acid Ligand is covalently attached to a Non-Immunogenic, High Molecular Weight Compound or Lipophilic Compound and is further associated with a Lipid Construct or the VEGF Nucleic Acid Ligand is encapsulated within a Lipid Construct.

In embodiments where there are multiple VEGF Nucleic Acid Ligands, there is an increase in avidity due to multiple binding interactions with VEGF. Furthermore, in embodiments where the Complex is comprised of multiple VEGF Nucleic Acid Ligands, the pharmacokinetic properties of the Complex will be improved relative to one VEGF Nucleic Acid Ligand alone. In embodiments where a Lipid Construct comprises multiple Nucleic Acid Ligands or Complexes, the Pharmacokinetic Properties of the VEGF Nucleic Acid Ligand may be improved relative to Lipid Constructs in which there is only one Nucleic Acid Ligand or Complex.

In certain embodiments of the invention, the Complex of the present invention is comprised of a VEGF Nucleic Acid Ligand attached to one (dimeric) or more (multimeric) other Nucleic Acid Ligands. The Nucleic Acid Ligand can be to VEGF or a different Target. In embodiments where there are multiple VEGF Nucleic Acid Ligands, there is an increase in avidity due to multiple binding interactions with VEGF. Furthermore, in embodiments of the invention where the Complex is comprised of a VEGF Nucleic Acid Ligand attached to one or more other VEGF Nucleic Acid Ligands, the pharmacokinetic properties of the Complex will be improved relative to one VEGF Nucleic Acid Ligand alone.

The Non-Immunogenic, High Molecular Weight compound or Lipophilic Compound may be covalently bound to a variety of positions on the VEGF Nucleic Acid Ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the VEGF Nucleic Acid Ligand. In embodiments where the Lipophilic Compound is a glycerolipid, or the Non-Immunogenic, High Molecular Weight Compound is polyalkylene glycol or polyethylene glycol, preferably it is bonded to the 5' or 3' hydroxyl of the phosphate group thereof. In the most preferred embodiment, the Lipophilic Compound or Non-Immunogenic, High Molecular Weight Compound is bonded to the 5' hydroxyl of the phosphate group of the Nucleic Acid Ligand. Attachment of the Non-Immunogenic, High Molecular Weight Compound or Lipophilic Compound to the VEGF Nucleic Acid Ligand can be done directly or with the utilization of Linkers or Spacers. In embodiments where the Lipid Construct comprises a Complex, or where the VEGF Nucleic Acid Ligands are encapsulated within the Liposome, a Non-Covalent Interaction between the VEGF Nucleic Acid Ligand or the Complex and the Lipid Construct is preferred.

One problem encountered in the therapeutic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the VEGF Nucleic Acid Ligand can be made to increase the in vivo stability of the VEGF Nucleic Acid Ligand or to enhance or to mediate the delivery of the VEGF Nucleic Acid Ligand. Modifications of the VEGF Nucleic Acid Ligands contemplated in this invention include, but are not limited to, those which provide other chemical groups that incorporate additional charge, polarizability, hydrophobicity, hydrogen bonding, electrostatic interaction, and fluxionality to the VEGF Nucleic Acid Ligand bases or to the VEGF Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield VEGF Nucleic Acid Ligands with both specificity for VEGF and improved in vivo stability. Post-SELEX modifications made to 2'-OH Nucleic Acid Ligands can result in improved in vivo stability without adversely affecting the binding capacity of the Nucleic Acid Ligands. The preferred modifications of the VEGF Nucleic Acid Ligands of the subject invention are 5' and 3' phosphorothioate capping and/or 3'3' inverted phosphodiester linkage at the 3' end. In the most preferred embodiment, the preferred modification of the VEGF Nucleic Acid Ligand is 3'3' inverted phosphodiester linkage at the 3' end. Additional 2' fluoro (2'-F), 2' amino (2'-NH$_2$) and 2' O methyl (2'-OMe) modification of some or all of the nucleotides is preferred.

In another aspect of the present invention, the covalent linking of the VEGF Nucleic Acid Ligand with a Non-Immunogenic, High Molecular Weight Compound or Lipophilic Compound results in Improved Pharmacokinetic Properties (i.e., slower clearance rate) relative to the VEGF Nucleic Acid Ligand not in association with a Non-Immunogenic, High Molecular Weight Compound or Lipophilic Compound.

In another aspect of the present invention, the Complex comprising a VEGF Nucleic Acid Ligand and Non-Immunogenic, High Molecular Weight Compound or Lipophilic Compound can be further associated with a Lipid Construct. This association may result in Improved Pharmacokinetic Properties relative to the VEGF Nucleic Acid Ligand or Complex not in association with a Lipid Construct. The VEGF Nucleic Acid Ligand or Complex can be associated with the Lipid Construct through covalent or Non-Covalent Interactions. In a preferred embodiment. the association is through Non-Covalent Interactions. In a preferred embodiment. the Lipid Construct is a Lipid Bilayer Vesicle. In the most preferred embodiment, the Lipid Construct is a Liposome.

Liposomes for use in the present invention can be prepared by any of the various techniques presently known in the art or subsequently developed. Typically, they are prepared from a phospholipid, for example, distearoyl phosphatidylcholine,and may include other materials such as neutral lipids, for example, cholesterol, and also surface modifiers such as positively charged (e.g., sterylamine or aminomannose or aminomannitol derivatives of cholesterol) or negatively charged (e.g., diacetyl phosphate, phosphatidyl glycerol) compounds. Multilamellar Liposomes can be formed by conventional techniques, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MILVs. UVs can then be formed by homogenization, sonication or extrusion (through filters) of MLV'S. In addition, UVs can be formed by detergent removal techniques.

In certain embodiments of this invention. the Lipid Construct comprises a targeting VEGF Nucleic Acid Ligand(s) associated with the surface of the Lipid Construct and an encapsulated therapeutic or diagnostic agent. Preferably the Lipid Construct is a Liposome. Preformed Liposomes can be modified to associate with the VEGF Nucleic Acid Ligands. For example, a Cationic Liposome associates through electrostatic interactions with the VEGF Nucleic Acid Ligand. A VEGF Nucleic Acid Ligand covalently linked to a Lipophilic Compound, such as a glycerolipid, can be added to preformed Liposomes whereby the glycerolipid, phospholipid, or glycerol amide lipid becomes associated with the liposomal membrane. Alternatively, the VEGF Nucleic Acid Ligand can be associated with the Liposome during the formulation of the Liposome.

It is well known in the art that Liposomes are advantageous for encapsulating or incorporating a wide variety of therapeutic and diagnostic agents. Any variety of compounds can be enclosed in the internal aqueous compartment of the Liposomes. Illustrative therapeutic agents include antibiotics, antiviral nucleosides, antifungal nucleosides, metabolic regulators, immune modulators, chemotherapeutic drugs, toxin antidotes, DNA, RNA, antisense oligonucleotides, etc. By the same token, the Lipid Bilayer Vesicles may be loaded with a diagnostic radionuclide (e.g., Indium 111, Iodine 131, Yttrium 90, Phosphorous 32, or gadolinium) and fluorescent materials or other materials that are detectable in in vitro and in vivo applications. It is to be understood that the therapeutic or diagnostic agent can be encapsulated by the Liposome walls in the aqueous interior. Alternatively, the carried agent can be a part of, that is, dispersed or dissolved in the vesicle wall-forming materials.

During Liposome formation, water soluble carrier agents may be encapsulated in the aqueous interior by including them in the hydrating solution, and lipophilic molecules incorporated into the lipid bilayer by inclusion in the lipid formulation. In the case of certain molecules (e.g., cationic or anionic lipophilic drugs), loading of the drug into preformed Liposomes may be accomplished, for example, by the methods described in U.S. Pat. No. 4,946,683, the disclosure of which is incorporated herein by reference. Following drug encapsulation, the Liposomes are processed to remove unencapsulated drug through processes such as gel chromatography or ultrafiltration. The Liposomes are then typically sterile filtered to remove any microorganisms which may be present in the suspension. Microorganisms may also be removed through aseptic processing.

If one wishes to encapsulate large hydrophilic molecules with Liposomes, larger unilamellar vesicles can be formed by methods such as the reverse-phase evaporation (REV) or solvent infusion methods. Other standard methods for the formation of Liposomes are known in the art, for example, methods for the commercial production of Liposomes include the homogenization procedure described in U.S. Pat. No. 4,753,788 and the thin-film evaporation method described in U.S. Pat. No. 4,935,171, which are incorporated herein by reference.

It is to be understood that the therapeutic or diagnostic agent can also be associated with the surface of the Lipid Bilayer Vesicle. For example, a drug can be attached to a phospholipid or glyceride (a prodrug). The phospholipid or glyceride portion of the prodrug can be incorporated into the lipid bilayer of the Liposome by inclusion in the lipid formulation or loading into preformed Liposomes (see U.S. Pat. Nos. 5,194,654 and 5,223,263, which are incorporated by reference herein).

It is readily apparent to one skilled in the art that the particular Liposome preparation method will depend on the intended use and the type of lipids used to form the bilayer membrane.

Lee and Low (1994, JBC, 269: 3198–3204) and DeFrees et al. (1996, JACS, 118: 6101–6104) first showed that co-formulation of ligand-PEG-lipid with lipid components gave liposomes with both inward and outward facing orientations of the PEG-ligand. Passive anchoring was outlined by Zalipsky et al. (1997, Bioconj. Chem. 8: 111–118) as a method for anchoring oligopeptide and oligosaccharide ligands exclusively to the external surface of liposomes. The central concept presented in their work is that ligand-PEGlipid conjugates can be prepared and then formulated into pre-formed liposomes via spontaneous incorporation ("anchoring") of the lipid tail into the existing lipid bilayer. The lipid group undergoes this insertion in order to reach a lower free energy state via the removal of its hydrophobic lipid anchor from aqueous solution and its subsequent positioning in the hydrophobic lipid bilayer. The key advantage to such a system is that the oligo-lipid is anchored exclusively to the exterior of the lipid bilayer. Thus, no oligo-lipids are wasted by being unavailable for interactions with their biological targets by being in an inward-facing orientation.

The efficiency of delivery of a VEGF Nucleic Acid Ligand to cells may be optimized by using lipid formulations and conditions known to enhance fusion of Liposomes with cellular membranes. For example, certain negatively charged lipids such as phosphatidylglycerol and phosphatidylserine promote fusion, especially in the presence of other fusogens (e.g., multivalent cations like $Ca^{2+}$, free fatty acids, viral fusion proteins, short chain PEG, lysolecithin, detergents and surfactants). Phosphatidylethanolamine may also be included in the Liposome formulation to increase membrane fusion and, concomitantly, enhance cellular delivery. In addition, free fatty acids and derivatives thereof, containing, for example, carboxylate moieties, may be used to prepare pH-sensitive Liposomes which are negatively charged at higher pH and neutral or protonated at lower pH. Such pH-sensitive Liposomes are known to possess a greater tendency to fuse.

In the preferred embodiment, the VEGF Nucleic Acid Ligands of the present invention are derived from the SELEX methodology. SELEX is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Method for Indentifying Nucleic Acid Ligands, now U.S. Pat. No. 5,270,163 (see also WO 91/19813). These applications, each specifically incorporated herein by reference, are collectively called the SELEX Patent Applications.

The SELEX process provides a class of products which are Nucleic Acid molecules, each having a unique sequence, and each of which has the property of binding specifically to a desired Target compound or molecule. Target molecules are preferably proteins, but can also include among others carbohydrates, peptidoglycans and a variety of small molecules. SELEX methodology can also be used to Target biological structures, such as cell surfaces or viruses, through specific interaction with a molecule that is an integral part of that biological structure.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-target pairs between the Target and those Nucleic Acids having the strongest affinity for the Target.

3) The Nucleic Acids with the highest affinity for the target are partitioned from those Nucleic Acids with lesser affinity to the target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity for the target are then amplified to create a new Candidate Mixture that is enriched in Nucleic Acids having a relatively higher affinity for the target.

5) By repeating the partitioning and amplifying steps above, the newly formed Candidate Mixture contains fewer and fewer unique sequences, and the average degree of affinity of the Nucleic Acids to the target will generally increase. Taken to its extreme, the SELEX process will yield a Candidate Mixture containing one or a small number of unique Nucleic Acids representing those Nucleic Acids from the original Candidate Mixture having the highest affinity to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935,filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV Rev," now U.S. Pat. No. 5,496,938, describes methods for obtaining improved Nucleic Acid Ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660, 985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637, 459, and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Complexes." The SELEX method further encompasses combining selected VEGF Nucleic Acid Ligands with lipophilic compounds, such as diacyl glycerol or dialkyl glycerol, as described in U.S. patent application Ser. No. 08/739,109, filed Oct. 25, 1996, entitled "Vascular Endothelial Growth Factor (VEGF) Nucleic Acid Ligand Complexes." VEGF Nucleic Acid Ligands that are associated with a High Molecular Weight, Non-Immunogenic Compound, such as Polyethylene glycol, or a Lipophilic Compound, such as Glycerolipid, phospholipid, or glycerol amide lipid, in a diagnostic or therapeutic complex are described in U.S. patent application Ser. No. 08/897,351, filed Jul. 21, 1997, entitled "Vascular Endothelial Growth Factor (VEGF) Nucleic Acid Complexes." Each of the above described patent applications which describe modifications of the basic SELEX procedure are specifically incorporated by reference herein in their entirety.

SELEX identifies Nucleic Acid Ligands that are able to bind targets with high affinity and with outstanding specificity, which represents a singular achievement that is unprecedented in the field of Nucleic Acids research. These characteristics are, of course, the desired properties one skilled in the art would seek in a therapeutic or diagnostic ligand.

In order to produce Nucleic Acid Ligands desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand has the highest possible affinity to the target. Additionally, Nucleic Acid Ligands can have facilitating properties.

In commonly assigned U.S. patent application Ser. No. 07/964,624, filed Oct. 21, 1992 ('624), now U.S. Pat. No. 5,496,938, methods are described for obtaining improved Nucleic Acid Ligands after SELEX has been performed. The '624 application, entitled Nucleic Acid Ligands to HIV-RT and HIV-1 Rev, is specifically incorporated herein by reference.

The SELEX process has been used to identify a group of high affinity RNA Ligands to VEGF from random 2'-aminopyrimidine RNA libraries and ssDNA ligands from random ssDNA libraries (U.S. patent application Ser. No. 08/447,169, filed May 19, 1995, entitled High-Affinity Oligonucleotide Ligands to Vascular Endothelial Growth Factor (VEGF), which is a Continuation-in-Part Application of U.S. patent application Ser. No. 08/233,012, filed Apr. 25, 1994, entitled High-Affinity Oligonucleotide Ligands to Vascular Endothelial Growth Factor (VEGF), both of which are incorporated herein by reference; see also Green et al. (1995) Chemistry and Biology 2:683–695).

In embodiments where the VEGF Nucleic Acid Ligand(s) can serve in a targeting capacity, the VEGF Nucleic Acid Ligands adopt a three dimensional structure that must be retained in order for the VEGF Nucleic Acid Ligand to be able to bind its target. In embodiments where the Lipid Construct comprises a Complex and the VEGF Nucleic Acid Ligand of the Complex is projecting from the surface of the Lipid Construct, the VEGF Nucleic Acid Ligand must be properly oriented with respect to the surface of the Lipid Construct so that its target binding capacity is not compromised. This can be accomplished by attaching the VEGF Nucleic Acid Ligand at a position that is distant from the binding portion of the VEGF Nucleic Acid Ligand. The three dimensional structure and proper orientation can also be preserved by use of a Linker or Spacer as described supra.

Any variety of therapeutic or diagnostic agents can be attached to the Complex for targeted delivery by the Complex. In addition, any variety of therapeutic or diagnostic agents can be attached encapsulated, or incorporated into the Lipid Construct as discussed supra for targeted delivery by the Lipid Construct.

In embodiments where the Complex is comprised of a Lipophilic Compound and a VEGF Nucleic Acid Ligand in association with a Liposome, for example, the VEGF Nucleic Acid Ligand could target tumor cells expressing VEGF (e.g., in Kaposi's sarcoma) for delivery of an anti-tumor drug (e.g., daunorubicin) or imaging agent (e.g., radiolabels). It should be noted that cells and tissues surrounding the tumor may also express VEGF, and targeted delivery of an antitumor drug to these cells would also be effective.

In an alternative embodiment, the therapeutic or diagnostic agent to be delivered to the Target cell could be another Nucleic Acid Ligand.

It is further contemplated by this invention that the agent to be delivered can be incorporated into the Complex in such a way as to be associated with the outside surface of the Liposome (e.g., a prodrug, receptor antagonist, or radioactive substance for treatment or imaging). As with the VEGF Nucleic Acid Ligand, the agent can be associated through covalent or Non-Covalent Interactions. The Liposome would provide targeted delivery of the agent extracellularly, with the Liposome serving as a Linker.

In another embodiment, a Non-Immunogenic, High Molecular Weight Compound (e.g., PEG) can be attached to the Liposome to provide Improved Pharmacokinetic Properties for the Complex. VEGF Nucleic Acid Ligands may be attached to the Liposome membrane or may be attached to a Non-Immunogenic, High Molecular Weight Compound which in turn is attached to the membrane. In this way, the Complex may be shielded from blood proteins and thus be made to circulate for extended periods of time while the VEGF Nucleic Acid Ligand is still sufficiently exposed to make contact with and bind to its Target.

In another embodiment of the present invention, more than one VEGF Nucleic Acid Ligand is attached to the surface of the same Liposome. This provides the a possibility of bringing the same VEGF molecules in close proximity to each other and can be used to generate specific interactions between the VEGF molecules.

In an alternative embodiment of the present invention, VEGF Nucleic Acid Ligands and a Nucleic Acid Ligand to a different Target can be attached to the surface of the same Liposome. This provides the possibility of bringing VEGF in close proximity to a different Target and can be used to generate specific interactions between VEGF and the other Target. In addition to using the Liposome as a way of bringing Targets in close proximity, agents could be encapsulated in the Liposome to increase the intensity of the interaction.

The Lipid Construct comprising a Complex allows for the possibility of multiple binding interactions to VEGF. This, of course, depends on the number of VEGF Nucleic Acid Ligands per Complex, and the number of Complexes per Lipid Construct, and mobility of the VEGF Nucleic Acid Ligands and receptors in their respective membranes. Since the effective binding constant may increase as the product of the binding constant for each site, there is a substantial advantage to having multiple binding interactions. In other words, by having many VEGF Nucleic Acid Ligands attached to the Lipid Construct, and therefore creating multivalency, the effective affinity (i.e., the avidity) of the multimeric Complex for its Target may become as good as the product of the binding constant for each site.

In certain embodiments of the invention, the Complex of the present invention is comprised of a VEGF Nucleic Acid Ligand attached to a Lipophilic Compound such as a glycerol lipid. In this case, the pharmacokinetic properties of the Complex will be improved relative to the VEGF Nucleic Acid Ligand alone. As discussed supra, the glycerol lipid, phospholipid or glycerol amide lipid may be covalently bound to the VEGF Nucleic Acid Ligand at numerous positions on the VEGF Nucleic Acid Ligand. In embodiments where a glycerol lipid is used, it is preferred that the VEGF Nucleic Acid Ligand is bonded to the lipid through phosphodiester linkages.

In another embodiment of the invention, the Lipid Construct comprises a VEGF Nucleic Acid Ligand or Complex. In this embodiment, the glycerolipid can assist in the incorporation of the VEGF Nucleic Acid Ligand into the Liposome due to the propensity for a glycerolipid to associate with other Lipophilic Compounds. The glycerolipid in association with a VEGF Nucleic Acid Ligand can be incorporated into the lipid bilayer of the Liposome by inclusion in the formulation or by loading into preformed Liposomes. The glycerolipid can associate with the membrane of the Liposome in such a way so as the VEGF Nucleic Acid Ligand is projecting into or out of the Liposome. In embodiments where the VEGF Nucleic Acid Ligand is projecting out of the Complex, the VEGF Nucleic Acid Ligand can serve in a targeting capacity. It is to be understood that additional compounds can be associated with the Lipid Construct to further improve the Pharmacokinetic Properties of the Lipid Construct. For example, a PEG may be attached to the exterior-facing part of the membrane of the Lipid Construct.

In other embodiments, the Complex of the present invention is comprised of a VEGF Nucleic Acid Ligand covalently linked to a Non-Immunogenic, High Molecular Weight Compound such as Polyalkylene Glycol or PEG. In this embodiment, the pharmacokinetic properties of the Complex are improved relative to the VEGF Nucleic Acid Ligand alone. The Polyalkylene Glycol or PEG may be covalently bound to a variety of positions on the VEGF Nucleic Acid Ligand. In embodiments where Polyalkylene Glycol or PEG are used, it is preferred that the VEGF Nucleic Acid Ligand is bonded through the 5' hydroxyl group via a phosphodiester linkage.

In certain embodiments, a plurality of Nucleic Acid Ligands can be associated with a single Non-Immunogenic, High Molecular Weight Compound, such as Polyalkylene Glycol or PEG, or a Lipophilic Compound, such as a glycerolipid. The Nucleic Acid Ligands can all be to VEGF or VEGF and a different Target. In embodiments where there are multiple VEGF Nucleic Acid Ligands, there is an increase in avidity due to multiple binding interactions with VEGF. In yet further embodiments, a plurality of Polyalkylene Glycol, PEG, glycerol lipid molecules can be attached to each other. In these embodiments, one or more VEGF Nucleic Acid Ligands or Nucleic Acid Ligands to VEGF and other Targets can be associated with each Polyalkylene Glycol, PEG, or glycerol lipid. This also results in an increase in avidity of each Nucleic Acid Ligand to its Target. In embodiments where multiple VEGF Nucleic Acid Ligands are attached to Polyalkylene Glycol, PEG, or glycerol lipid, there is the possibility of bringing VEGF molecules in close proximity to each other in order to generate specific interactions between VEGF. Where multiple Nucleic Acid Ligands specific for VEGF and different Targets are attached to Polyalkylene Glycol, PEG, or glycerol lipid, there is the possibility of bringing VEGF and another Target in close proximity to each other in order to generate specific interactions between the VEGF and the other Target. In addition, in embodiments where there are Nucleic Acid Ligands to VEGF or Nucleic Acid Ligands to VEGF and different Targets associated with Polyalkylene Glycol, PEG, or glycerol lipid, a drug can also be associated with Polyalkylene Glycol, PEG, or glycerol lipid. Thus the Complex would provide targeted delivery of the drug, with Polyalkylene Glycol, PEG, or glycerol lipid serving as a Linker.

VEGF Nucleic Acid Ligands selectively bind VEGF. Thus, a Complex comprising a VEGF Nucleic Acid Ligand and a Non-Immunogenic, High Molecular Weight Compound or Lipophilic Compound or a Lipid Construct comprising a VEGF Nucleic Acid Ligand or a Complex are useful as pharmaceuticals or diagnostic agents. The present invention, therefore, includes methods of inhibiting angiogenesis by administration of a Complex comprising VEGF Nucleic Acid Ligand and a Non-Immunogenic, High Molecular Weight Compound or Lipophilic Compound, a Lipid Construct comprising VEGF Nucleic Acid Ligand or a Complex comprising a VEGF Nucleic Acid Ligand and a Non-Immunogenic, High Molecular Weight Compound or Lipophilic Compound. The VEGF Nucleic Acid Ligand-containing Complexes and Lipid Constructs can be used to treat, inhibit, prevent or diagnose any disease state that involves inappropriate VEGF production, particularly angiogenesis. Angiogenesis rarely occurs in healthy adults, except during the menstrual cycle and wound healing. Angiogenesis is a central feature, however, of various disease states, including, but not limited to cancer, diabetic retinopathy, macular degeneration, psoriasis and rheumatoid arthritis. The present invention, thus, also includes, but is not limited to, methods of treating, inhibiting, preventing or diagnosing diabetic retinopathy, macular degeneration, psoriasis and rheumatoid arthritis. Additionally, VEGF is produced and secreted in varying amounts by virtually all tumor cells. Thus, the present invention, includes methods of treating, inhibiting, preventing, or diagnosing cancer by administration of a Complex comprising a VEGF Nucleic Acid Ligand and a Non-Immunogenic, High Molecular Weight Compound or Lipophilic Compound, a Lipid Construct comprising a Complex, or a VEGF Nucleic Acid Ligand in association with a Lipid Construct without being part of the Complex. It has been shown that in a type of cancer, Kaposi's sarcoma (KS), cells not only produce abundant amounts of VEGF but also express functional VEGF receptors and therefore use VEGF for autocrine growth. Thus, the present invention includes a method of inhibiting Kaposi's Sarcoma by administration of a Complex comprising VEGF Nucleic Acid Ligand and a Non-Immunogenic, High Molecular Weight Compound or a Lipophilic Compound, a Lipid Construct comprising a Complex, or a VEGF Nucleic Acid Ligand in association with a Lipid Construct without being part of a Complex.

In one embodiment of the present invention, the Lipid Construct comprises a Complex comprised of a VEGF Nucleic Acid Ligand and a Lipophilic Compound with an additional diagnostic or therapeutic agent encapsulated in the Lipid Construct or associated with the interior of the Lipid Construct. In the preferred embodiment, the Lipid Construct is a Lipid Bilayer Vesicle, and more preferably a Liposome. The therapeutic use of Liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. In one embodiment of the present invention, the VEGF Nucleic Acid Ligand is associated with the outside surface of the liposome, and serves in a targeting capacity. Additional targeting components, such as antibodies or specific receptor ligands can be included on the liposome surface, as would be known to one of skill 25 in the art. In addition, some efforts have been successful in targeting liposomes to tumors without the use of antibodies, see, for example, U.S. Pat. Nos. 5,019,369, 5,435,989, and 4,441,775, and it would be known to one of skill in the art to incorporate these alternative targeting methods.

Therapeutic or diagnostic compositions of a Complex comprising VEGF Nucleic Acid Ligand and a Non-Immunogenic, High Molecular Weight Compound or Lipophilic Compound, a Lipid Construct comprising a Complex comprised of a VEGF Nucleic Acid Ligand and a Non-Immunogenic, High Molecular Weight Compound or Lipophilic Compound, and a VEGF Nucleic Acid Ligand in association with a Lipid Construct without being part of a Complex may be administered parenterally by injection, although other effective administration forms, such as intraarticular injection, inhalant mists, orally active formulations, transdermal iotophoresis or suppositories, are also envisioned. One preferred carrier is physiological saline solution, but it is contemplated that other pharmaceutically acceptable carriers may also be used. In one embodiment, it is envisioned that the carrier and the VEGF Nucleic Acid Ligand Complex constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the VEGF Nucleic Acid Ligand. Such excipients are those substances usually and customarily employed to formulate dosages for parental administration in either unit dose or multi-dose form.

Once the therapeutic or diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to administration. The manner of administering formulations containing VEGF Nucleic Acid Ligand for systemic delivery may be via subcutaneous, intramuscular, intravenous, intranasal or vaginal or rectal suppository.

The advantages of the Complexes and Lipid Constructs of the invention include: i) improving the plasma pharmacokinetics of the Nucleic Acid Ligand; ii) presenting Nucleic Acid Ligands in a multivalent array with the aim of increasing the avidity of interaction with their targets; iii) combining two or more presenting Nucleic Acid Ligands with different specificities in the same liposome particle; iv) enhancing the delivery of presenting Nucleic Acid Ligands to tumors by taking advantage of the intrinsic tumor targeting properties of liposomes; and v) using the high affinity and specificity of presenting Nucleic Acid Ligands, which is comparable to that of antibodies, to guide liposomal contents to specific targets. Presenting Nucleic Acid Ligands are well suited for the kinds of preparations described here since, unlike most proteins, the denaturation of presenting Nucleic Acid Ligands by heat, various molecular denaturants and organic solvents is readily reversible.

The following examples are provided to explain and illustrate the present invention and are not to be taken as limiting of the invention. The structures of the Nucleic Acid Ligands described in the examples below are shown in FIG. 1. Example 1 describes the conjugation of Nucleic Acid Ligands with lipid reagents. The ability of a dialkylglycerol derivative of the VEGF Nucleic Acid Ligand (NX278), either as a free ligand or incorporated in the bilayer of liposomes (NX278-L), to inhibit the activity of VEGF in vitro and in vivo is described in Example 2. Example 3 describes the experimental procedures for generating 2'-F pyrimidine modified RNA ligands to VEGF. Example4 describes the 2'-F pyrimidine-modified RNA ligands to VEGF. Example 5 describes the synthesis of glycerolipid, phospholipid, and glycerol amide lipid, and PEG-modified VEGF Nucleic Acid Ligands. Example 6 describes the pharmacokinetic properties of phospholipid (PL) and PEG modified VEGF Nucleic Acid Ligands. Example 7 describes preparations of NX3 1838 PL-Liposome Complex. Examples 8–10 describe the in vivo efficacy of VEGF Nucleic Acid Ligand Complexes. Example 11 describes the intravitreal pharmacokinetics of NX31838-40K PEG in rabbits.

Example 1

Synthesis of a dialkyl glycerol (1,2-di-O-octadecyl-sn-glycerol)-modified VEGF Nucleic Acid Ligand In this example, conjugation of Nucleic Acid Ligands with lipid reagents is described. Synthesis of (1,2-di-O-octadecyl-sn-glycerol)—modified VEGF Nucleic Acid Ligand is shown below.

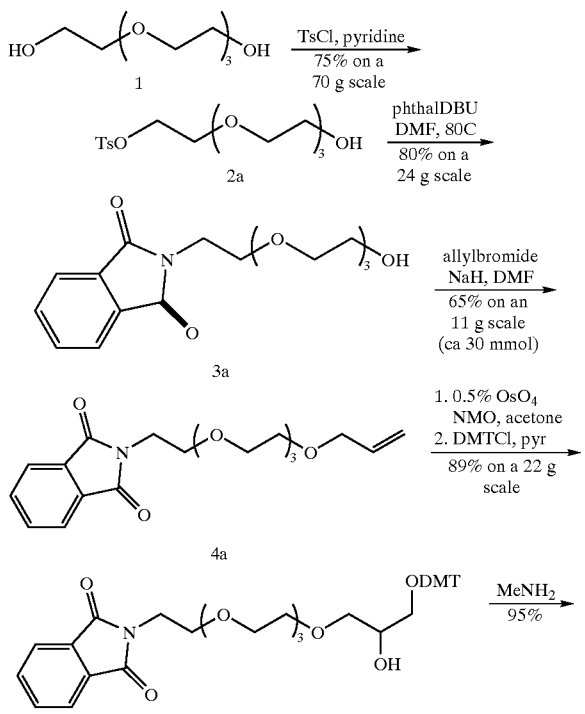

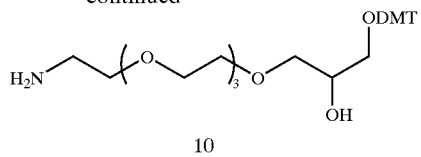

Tetraethylene glycol monotosylate (2a)

Tetraethylene glycol (200 mL, 1.15 mol) was dissolved in 500 mL of pyridine and cooled to 0° C. and treated with 22.0 g (0.115 mol) of p-toluenesulfonyl chloride. When solution was complete, the reaction mixture was stored in the refrigerator overnight, and then concentrated in vacuo. The residue was dissolved in 800 mL of EtOAc and extracted with 3×600 mL of $H_2O$. The $H_2O$ fractions were back-extracted with EtOAc, and the combined EtOAc fractions were extracted with saturated aqueous $Na_2HPO_4$. The organic phase was dried over $MgSO_4$ and concentrated to a colorless oil. The oil was purified by flash chromatography using 800 mL of silica gel and eluting with hexane, 25% EtOAc-50% EtOAc in hexane, then EtOAc, then 10% MeOH-20% MeOH in EtOAc to afford 23.7 g (60%) of pure product and 11% of product containing a minor impurity. 2a: $^1H$ NMR (300 MHz, $CDCl_3$) d 7.77 (d, J=8.1 Hz, 2H), 7.32 (d, J=8.1 Hz, 2H), 4.13 (t, J=4.8 Hz, 2H), 3.68–3.53 (m, 14H), 2.58 (t, J=5.6 Hz, 1H), 2.42 (s, 3H); $^{13}C$ NMR (75 MHz, $CDCl_3$) d 168.2, 158.3, 144.8, 135.9, 133.8, 132.0, 129.9, 128.0, 127.7, 126.6, 123.1, 113.0, 85.9, 73.0, 70.6, 70.4, 70.0, 69.7, 67.8, 64.4, 55.1, 37.1; Low resolution MS m/e calculated for $C_{15}H_{24}O_8S$ (M+1): 349.1.

Tetraethylene glycol monophthalimide (3a)

To a stirred solution of 31.96 g (0.092 mol) of 2a in 400 mL of anhydrous DMF was added 14.2 g (1.05 equiv.) of phthalimide and 14.4 mL (1.05 equiv.) of 1,8-diazabicyclo [5.4.0]undec-7-ene. The solution was heated at 70° C. for 18 h then concentrated in vacuo. The crude yellow oil was purified by flash chromatography using 1600 mL of silica gel and eluting with 25% EtOAc-50% EtOAc-75% EtOAc in hexane, then EtOAc, then 10% MeOH-20% MeOH in EtOAc to afford 23.8 g (80%) of 3a as an oil. Upon standing, 3a became a waxy white solid. $^1H$ NMR (300 MHz, $CDCl_3$) d 7.84–7.78 (m, 2H), 7.70–7.66 (m, 2H), 3.86 (t, J=5.6 Hz, 2H) 3.70 (t, J=5.6 Hz, 2H), 3.64–3.51 (m, 12H), 2.67 (bs, 1H); $^{13}C$ NMR (75 MHz, $CDCl_3$) d 168.2, 133.8, 132.0, 123.1, 72.4, 70.5, 70.4, 70.2, 70.0, 67.8, 61.6, 37.2.

Synthesis of compound 4a

A solution of 15 g (0.0464 mol) of 3a in 150 mL of THF and 15 ml, of DMF was cooled to 0° C. under Ar. Allyl bromide (6.0 mL, 1.5 equiv.) was added to the solution, followed by addition of 1.76 g (1.5 equiv.) of NaH as a solid. The opaque yellow suspension was stirred at 0° C. for 30 minutes and then at room temperature for 18 hr. MeOH (50–100 mL) was added and concentrated then mixture was concentrated in vacuo. The crude material was purified by flash chromatography using 1500 mL of silica gel and eluting with 25% EtOAc-50% EtOAc-75% EtOAc in hexane, then EtOAc, then 10% MeOH in EtOAc to afford 11.05 g (65%) of 4a as a yellow oil. $^1H$ NMR (300 MHz, $CDCl_3$) d 7.84–7.80 (m, 2H), 7.72–7.67 (m, 2H), 5.94–5.84 (m, 1H), 5.28–5.14 (m, 2H). 3.99 (d, J=5.61 Hz, 2H), 3.88 (t, J=5.85 Hz, 2H), 3.72 (t, J=5.76 Hz, 2H), 3.64–3.54 (m, 13H); $^{13}C$ NMR (75 MHz, $CDCl_3$) d 168.0, 134.6, 133.7, 131.9, 123.0, 116.9, 72.0, 70.4, 69.9, 69.2, 67.7, 37.0.

1-Dimethoxytrityl-3-(phthalimidotetraethyleneglycolyl)-sn-glycerol (9)

According to Scheme 1, compound 9 was synthesized as follows: To a stirred solution of 4a (10.13 g, 0.0279 mol) in 100 mL of acetone and 1 mL of H$_2$O was added 3.98 g (1.22 equiv.) of N-methylmorpholineN-oxide. To this suspension was added 1.75 mL (0.005 equiv.) of Osmium tetroxide as a 2.5% solution in iPrOH. After addition of the OsO$_4$ solution, the reaction mixture became clear yellow. After TLC analysis indicated complete conversion of 4a (ca 16 h), the reaction mixture was treated with 1.5 g of sodium hydrosulfite and 5.0 g of florisil and stirred 30 minutes. The suspension was filtered through florisil, the filtrate was concentrated to an oil. This crude product was combined with another batch prepared in the same manner from 1.0 g of 4a. Two 100 mL portions of pyridine were co-evaporated from the combined lots and the residue was dissolved in 300 mL pyridine. The solution was cooled to 0° C. and 10.89 g (1.05 equiv.) of 4,4'-dimethoxytrityl chloride was added. A ture was heated at 50° C. for 5 hr, and then was concentrated in vacuo and coevaporated with toluene. The crude material was purified by flash chromatography on 200 mL of silica gel, eluting with 15% methanolic ammonia in dichloromethane. Collected 3.94 g (96%) of 10 as a pale yellow oil. $^1$H NMR (300 MHz, CDCl$_3$) d 7.46–7.21 (m, 9H, DMT), 6.81 (d, 4H, DMT), 4.00 (m, 1H), 3.80 (s, 6H), 3.70–3.49 (overlapping m, 18H), 3.20 (dd, J=9.24, 5.49 Hz, 1H), 3.12 (dd, J=9.21, 6.0 Hz, 1H), 2.84–2.80 (m, 3H); $^{13}$C NMR (75 MHz, CDCl$_3$) d 158.30, 144.82, 136.01, 129.95, 128.04, 127.66, 126.61, 112.95, 85.85, 73.46, 72.85, 70.55, 70.45, 69.99, 69.51, 64.43, 55.10, 41.40; Low resolution MS m/e calculated for C$_{32}$H$_{44}$O$_8$N (M+1+): 570.353, found 570.4.

Scheme 2

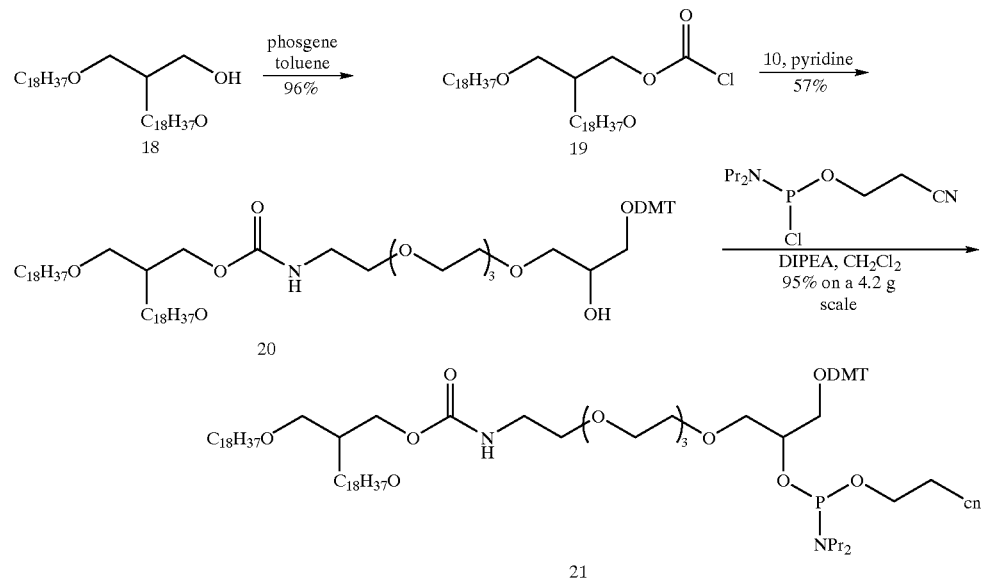

drying tube was inserted in the flask and the reaction mixture was stirred at room temperature 16 h. The solution was treated with 20 mL of MeOH and concentrated in vacuo, keeping the temperature of the water bath below 40° C. The crude oil was purified by flash chromatography using 1100 mL of silica gel (wet-packed onto column using 3% triethylamine in hexane) and eluting with 10–100% EtOAc in hexane (all containing 3% triethylamine)to give 21.3 g (89% after two steps) of 9 as a yellow oil. $^1$H NMR (300 MHz, CDCl$_3$) d 7.80–7.77 (m, 2H), 7.66–7.64 (m, 2H), 7.39–7.22 (m, 9H), 7.20–6.76 (m, 4H), 3.97 (bs, 1H), 3.84 (t, J=5.97 Hz, 2H), 3.74 (s, 6H), 3.68 (t, J=5.7 Hz, 2H), 3.60–3.49 (m, 14H), 3.13–2.76(m, 2H), 2.00 (bs, 1H); $^{13}$C NMR (75 MHz, CDCl3) d 168.2, 158.3, 144.8, 135.9, 133.8, 132.0, 129.9, 128.0, 127.7, 126.6, 123.1, 113.0, 85.9, 73.0, 70.6, 70.4, 70.0, 69.7, 67.8, 64.4, 55.1, 37.1; Low resolution MS m/e calculated for C$_{40}$H$_{45}$O$_{10}$N (M+NH$_4$+): 717.5.

1-Dimethoxytrityl-3-(aminotetraethyleneglycolyl)-sn-glycerol (10)

According to Scheme 1, compound 10 was synthesized as follows: Compound 9 (5.2 g, 7.2 mmol) was taken up in 50 mL of 40% methylamine in H$_2$O and 10 mL of methanol was added to solubilize the starting material. The reaction mix- Chloroformate 19: To a stirred solution of 3 g (5.03 mmol) of 1,2di-O-octadecyl-sn-glycerol 18 in 60 mL of toluene was added 20 mL of a 1.93 M solution of phosgene. Additional phosgene solution (2×10 mL; 15.4 equiv phosgene total) was added until no further alcohol starting material remained (by $^1$H NMR analysis of concentrated aliquots). The excess phosgene and HCl was removed by aspirator and the reaction mixture was concentrated in vacuo to afford 3.3 g (98%) of the desired chloroformate 19 as a white powder. $^1$H NMR (300 MHz, CDCl$_3$) d 4.45 (dd, J=11.22, 3.69 Hz, 1H), 4.34 (dd, J=11.22, 6.15 Hz, 1H), 3.65 (m, 1H), 3.56–3.40 (m, 6H), 1.53 (m, 4H), 1.24 (m, 62H), 0.87 (t, J=6.36 Hz, 6H); $^{13}$C NMR (75 MHz, CDCl$_3$) d 75.90, 71.91, 71.35, 70.93, 69.36, 31.99, 29.96–29.44 (overlapping signals from hydrocarbon chains), 26.13, 26.04, 22.76, 14.18.

Conjugate 20: To a stirred solution of 2.25 g (3.95 mmol) of 10 in 60 mL of pyridine was added 2.6 g of the distearyl glycerol chloroformate 18. $^1$H NMR analysis of a concentrated aliquot after 2 h revealed no remaining chloroformate and the mixture was concentrated in vacuo. The crude residue was combined with material similarly prepared from 0.5 g (0.88 mmol) of 10 and 0.58 g of the chloroformate and the combined lots purified by flash silica gel chromatography on a column of 100 mL of silica gel (packed in hexanes containing 2% triethylamine) eluting with 200 mL hexanes, then 250 mL each of 10–20 and 30% EtOAc in hexanes, 500 mL 40% EtOAc in hexanes, then 250 mL each of 50–60–70 and 80% EtOAc in hexanes, and finally with 250 mL of EtOAc. The product containing fractions were concentrated to afford 3.3 g (57%) of the conjugate 20.

Phosphoramidite21: To a stirred solution of 3.8 g (3.26 mmol) of the conjugate in 25 mL of $CH_2Cl_2$ was added 1.14 mL (6.52 mmol) of diisopropylethylaminethen 1.09 mL (4.88 mmol) of 2-cyanoethyl N,N-diisopropylchlorophosphoramidite. After 2 hours, the mixture was diluted with $CH_2Cl_2$ and washed with saturated $NaHCO_3$ solution, dried over $Na_2SO_4$, and concentrated, The crude residue was purified by flash silica gel chromatography on a column of 125 mL of silica gel (packed in hexanes containing 2% triethylamine) eluting with 100 mL hexanes, then 250 mL each of 10 and 20% EtOAc in hexanes, 500 mL 30% EtOAc in hexanes, then 250 mL of 50% EtOAc in hexanes. The product containing fractions were concentrated to afford 4.2 g (95%) of the phosphoramidite21. $^{31}P$ NMR ($CDCl_3$) d 151.52, 151.08.

The VEGF Nucleic Acid Ligand-1,2-di-O-octadecyl-sn-glycerolconjugate

The 1,2-di-O-octadecyl-sn-glycerolgroup was conjugated to VEGF Nucleic Acid Ligand NX213 (See FIG. 1A) using phosphoramidite 21 (Scheme 2). The resulting conjugate was named NX278 (See FIG. 1B). NX278 (SEQ ID No: 2) was purified by reverse phase HPLC and its composition was confirmed by electrospray mass spectroscopy (m/z observed=11703"±4, m/z calculated=11720). Phosphorothioate internucleoside linkages were used at 8 positions in NX278 (at the 3' and 5' ends) and the difference of 0.16 mass units between the expected and observed masses is probably due to incomplete oxidation by the sulfurizing agent resulting, on average, in one less phosphorothioate linkage per molecule than expected.

Example 2

In vitro and in vivo efficacy of Nucleic Acid Ligand-Liposome Complex. Dialkylglycerol(DAG)-modified VEGF Nucleic Acid Ligand (NX278) embedded in Liposome bilayer.

NX278-Liposome Complex was prepared by incubating NX-278 (1 mg) (FIG. 1B; SEQ ID NO: 2) with a spray-dried mixture of DSPC:cholesterol(50 mg/ml; 2:1, Mol:Mol) in 25 mM phosphate (pH 7.4) buffer containing 9% sucrose and sonicated for 15–30 min at approximately 60 degrees C. using a probe-type sonicator until opalescent solution was obtained. The control Nucleic Acid Ligand-Liposome Complex containing a sequence scrambled analog of ligand NX-278 (scNX278) (FIG. 1C; SEQ ID NO:3) was prepared in the same manner. In a typical preparation, liposomes with a mean diameter of 50 nm and a distribution width at half height of 20 nm were obtained. The size of Liposome particles was determined in a particle analyzer (Leeds & Northrup Model Microtrack UPA 150, Horsham, Pa.). Liposomes of comparable size distribution were obtained with the same lipid composition but without the lipid-conjugated Nucleic Acid Ligand. A 50 nm liposome is expected to contain an average of 40 Nucleic Acid Ligands, displayed on both sides of the bilayer. The calculation was made as follows. Assuming a surface area of 19 Å for cholesterol and 60 Å for distearylphoshatidylcholine in the liposome, a number of lipid molecules per liposome of $3.13 \times 10^4$ was obtained, for a spherical liposome with 50 nm outer diameter and membrane thickness of 20 Å. From the composition of the liposome (2:1 mol:mol distearyphosphatidylcholine (MW=790.2):cholesterol(MW=386.7)), assuming homogeneous distribution of lipids, molecular mass of $2.1 \times 10^7$ for the liposome was calculated.

To determine the partitioning of the Nucleic Acid Ligands between the inside and outside surfaces of liposomes, the accessibility of NX278 in the liposomal formulation to $T_1$ ribonuclease was examined. With two riboguanosines in the sequence (Green et al. (1995) Chemistry and Biology 2:683–695), NX278 is efficiently cleaved by ribonuclease $T_1$. Simple incubation of NX278 with preformed liposomes does not protect the Nucleic Acid Ligand from ribonuclease $T_1$. However, when NX278 is incorporated in liposomes by sonication (NX278-Liposome), about ⅓ is protected from the nuclease. The addition of 0.1% triton X-100 to NX278-Liposome, which disrupts the liposomes without affecting the activity of the nuclease, exposes the previously protected Nucleic Acid Ligand to digestion. These results are consistent with the notion that the Nucleic Acid Ligand is distributed on both sides of the bilayer.

Binding Affinities of NX213, NX278, and NX278-Liposome for VEGF

Figure 2:
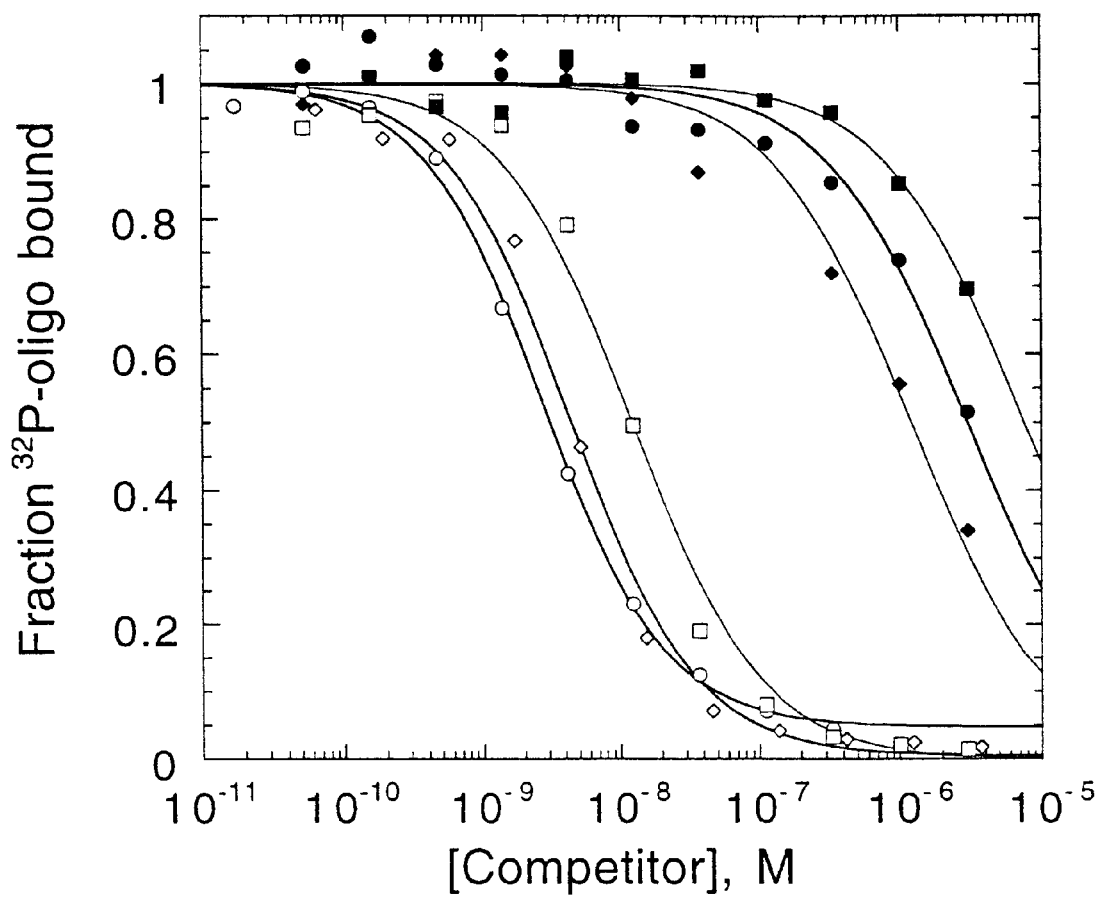
FIG. 2 shows binding properties of various Nucleic Acid Ligands to VEGF. The binding affinities of the unmodified Nucleic Acid Ligand (NX213, open circle), its dialkyl glycerol modified analog (NX278, open diamond) and liposomal NX278 (NX278-L, open square), along with the sequence scrambled (sc) controls (scNX213, closed circle; scNX278, closed diamond; and scNX278-L, closed square) were determined by a competition electrophoreticmobility shift assay. NX213 is 5'-TsTsTsTs mAaCaC aCaUrG rAaUmG rGaUmA mGrAaC mGaCaC mGmGmG mGaUmG TsTsTsTsT-3' and scNX213 is (SEQ ID NO:1) 5'-TsTsTsTs mGaUaC mGmGaU mAaCrG mGrAmG aUmGrG rAaCnC mGaUaC mAaCmG TsTsTsTsT-3' (SEQ ID NO:4) $^{32}$P 5=end-labeled NX-213 (1.5 nM) was incubated in binding buffer (phosphate buffered saline with 0.01% human serum albumin) at 37° C. for 20 min in the presence of VEGF (0.33 nM) and competitor oligonucleotide(5 pM-0.33 µM). The $^{32}$p NX-213/VEGF complex was resolved from the free $^{32}$p NX-213 by electrophoresison 8% polyacrylamide gel (19:1 acrylamide:bisacrylamide, Tris-borate, 89 mM, 1 mM EDTA as the running buffer). The intensity of the band corresponding to $^{32}$P NX-213/VEGF complex at varying competitor concentrations was quantitated by phosphorimager analysis. Data normalized for the amount of complex formed in the absence of competitor were fitted by the least squares method to the competition binding equation.

The binding affinities of NX213, NX278 and NX278-Liposome for VEGF were examined using a competition electrophoretic mobility shift method (FIG. 2). The binding affinity of NX278 for VEGF was comparable to that of NX213. The apparent binding affinity of NX278-Liposome was 3-fold lower compared with NX278. A part of the observed affinity reduction is potentially due to the confinement of a fraction of the Nucleic Acid Ligand to the liposome interior. As expected, the sequence scrambled analogs bind to VEGF with substantially lower affinities (FIG. 2).

Plasma Pharmacokinetic Properties of NX213, NX278, and NX278-Liposome

Figure 15:
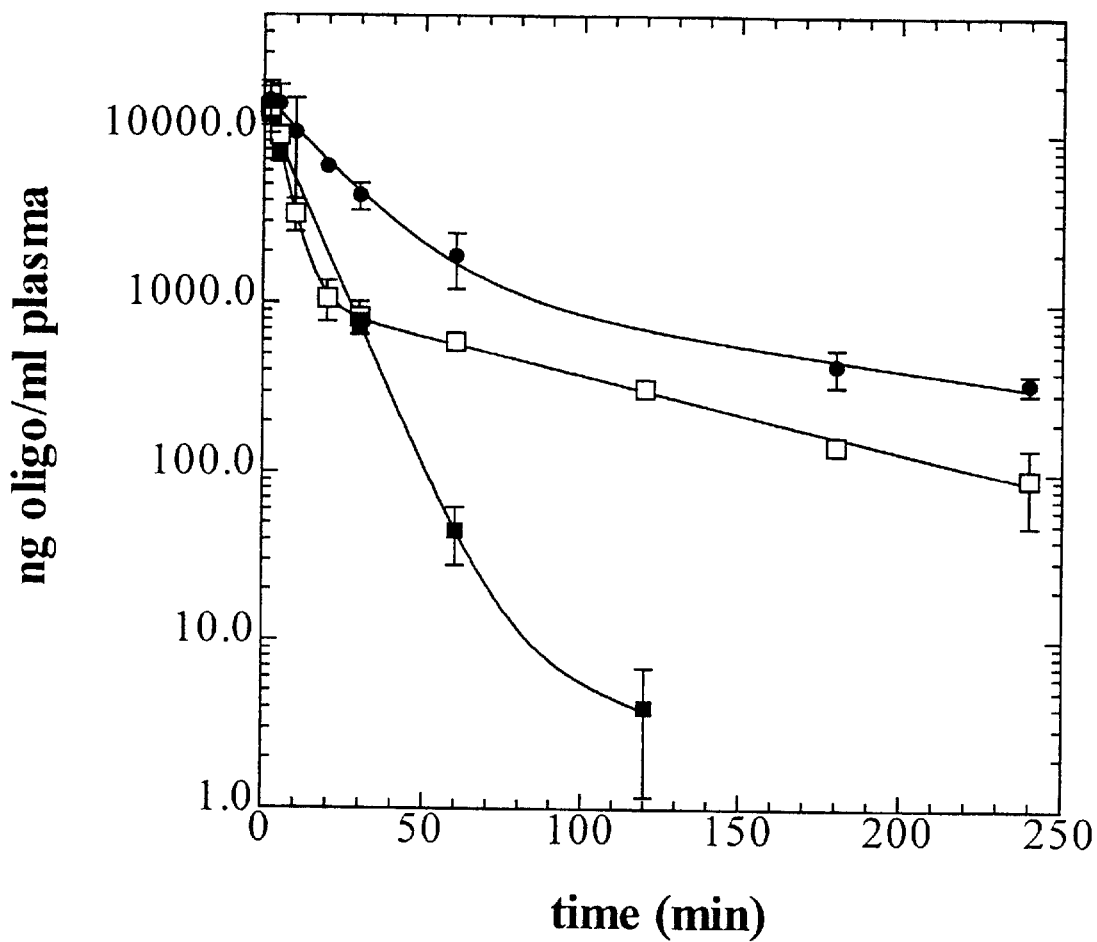
FIG. 15 summarizes the data for the plasma concentration of NX213, NX278, NX278-Liposome following bolus injection.

The concentrations of NX213, NX278 and NX278-Liposome in the plasma of Sprague Dawley rats as a function of time are shown in FIG. 15, and the parameters from compartmental analysis are summarized in Table 1. The majority of NX213 is cleared rapidly in the alpha phase with a $t_{1/2}$ of 7 minutes and an overall clearance rate of 6.8 ml/kg/min. Conjugation of a phospholipid group to the Nucleic Acid Ligand results in highly biphasic clearance from the blood with increased $\beta(t_{1/2})$ and somewhat slower overall rate of clearance (4.95 ml/kg/min) relative to NX213. Incorporation of NX278 into a liposome shows a substantial additional decrease in clearance of the Nucleic Acid Ligand from plasma (1.88 ml/kg/min).

The Effect of NX278 on HUVEC Proliferation and Angiogenesis

The effects of NX278-liposome, scNX278-liposome and NX213 on the proliferation of human umbilical vein endothelial cells (HUVEC) was examined. HUVECs were grown in the presence of VEGF (10 ng/ml) in IMDM:Ham's F12 (1:1) medium containing 10% fetal calf serum (FCS) and heparin (45 $\mu$g/ml). Cells were plated in 24-well gelatin-coated plates at a density of 20,000 cells per well on day zero and treated with the above ligands at concentrations between 0.1 nM to 1 $\mu$M on days 1, 2, and 3 (replacing the media along with the ligands. NX278-Liposome inhibited the proliferation of HUVECs with an IC50 of ≈300 nM (the concentration refers to the Nucleic Acid Ligand component); scNX278-Liposome and NX213 were significantly less effective (IC50>1 $\mu$g).

VEGF induces angiogenesis in chicken allantoic membrane (CAM) assays, and this assay can be utilized to study compounds that inhibit angiogenesis. The assay is done by placing filter discs soaked in VEGF on the CAM and the development of new blood vessels can be quantitiated. NX278-Liposome effectively blocked VEGF induced angiogenesis (data not shown), while NX213, NX278, and scNX278-Liposome had no effect. Together these studies demonstrate that NX278 is a specific inhibitor of VEGF induced endothelial cell proliferation in vitro and new vessel formation in vivo.

Effect of NX278 on VEGF Induced Capillary Permeability

Figure 3:
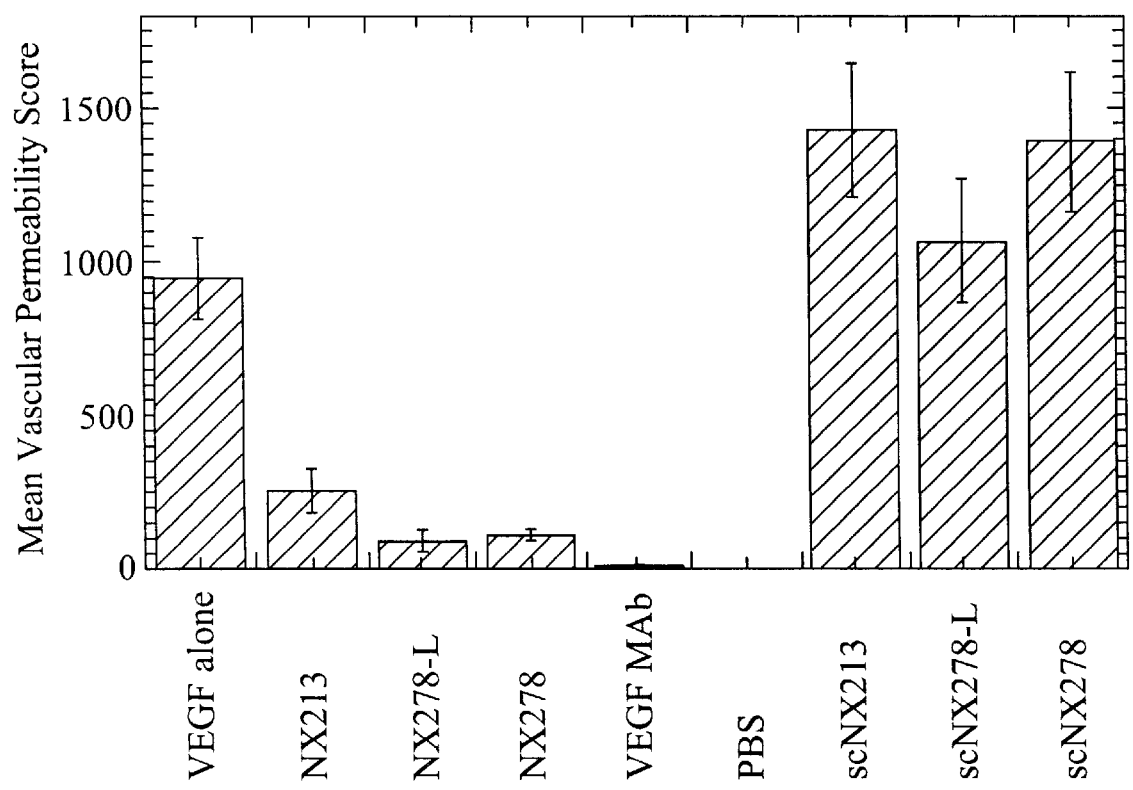
FIG. 3 shows the effect of various Nucleic Acid Ligands on VEGF-induced increases in vascular permeability. VEGF (20 nM) with or without Nucleic Acid Ligands was injected intradermally to guinea pigs that had previously received an injection of Evans blue dye. The amount of dye leakage was quantitated by measuring the relative amount of light absorbed by the skin at the site of injection.

VEGF is the only known angiogenic factor that transiently enhances capillary permeability. The ability of NX278-Liposome to inhibit the vascular permeability activity of VEGF in vivo was examined. The vascular permeability assay (also known as the Miles assay (Miles, A. A. and Miles, E. M. (1952) *J. Physiol.* (London) 118:228) was performed in guinea pigs essentially as described (Senger, R. S. et al., (I 1983) *Science* 219:983). NX278-Liposome, NX278, and NX213 at the concentration of 1 μM were injected intradermally with VEGF (20 nM) in guinea pigs preinjected with Evans blue dye. In response to VEGF, an increase in vascular permeability causes extravasation of albumin-bound Evans blue dye resulting in a blue spot at the site of injection. Because the recovery of the dye by organic solvent extraction is generally very poor, a quantitation method has been developed that measures the absorption of light through the skin. NX213, NX278, NX278-Liposome and neutralizing monoclonal antibody to VEGF all significantly inhibited VEGF-induced permeability as shown in FIG. 3. Among the Nucleic Acid Ligands, NX278-Liposome appeared to be the most potent antagonist. Sequence scrambled analogs of these compounds were not inhibitory. The differences were dramatic and noticeable to the naked eye.

NX278-L Inhibits Kaposi's Sarcoma Cell Lines in vitro

Inhibitors of VEGF have a potential utility in a variety of diseases, including malignancies where tumor progression and metastasis are dependent on new vessel formation. While most tumor types are known to produce VEGF, previously none has been shown to express functional VEGF receptors. It has been shown recently that Kaposi's Sarcoma (KS) cells not only produce abundant amounts of VEGF but also express functional VEGF receptors and therefore use VEGF for autocrine growth. KS cell lines thus provide a unique opportunity to examine the ability of NX278 to interrupt the autocrine VEGF growth activity.

Figure 4:
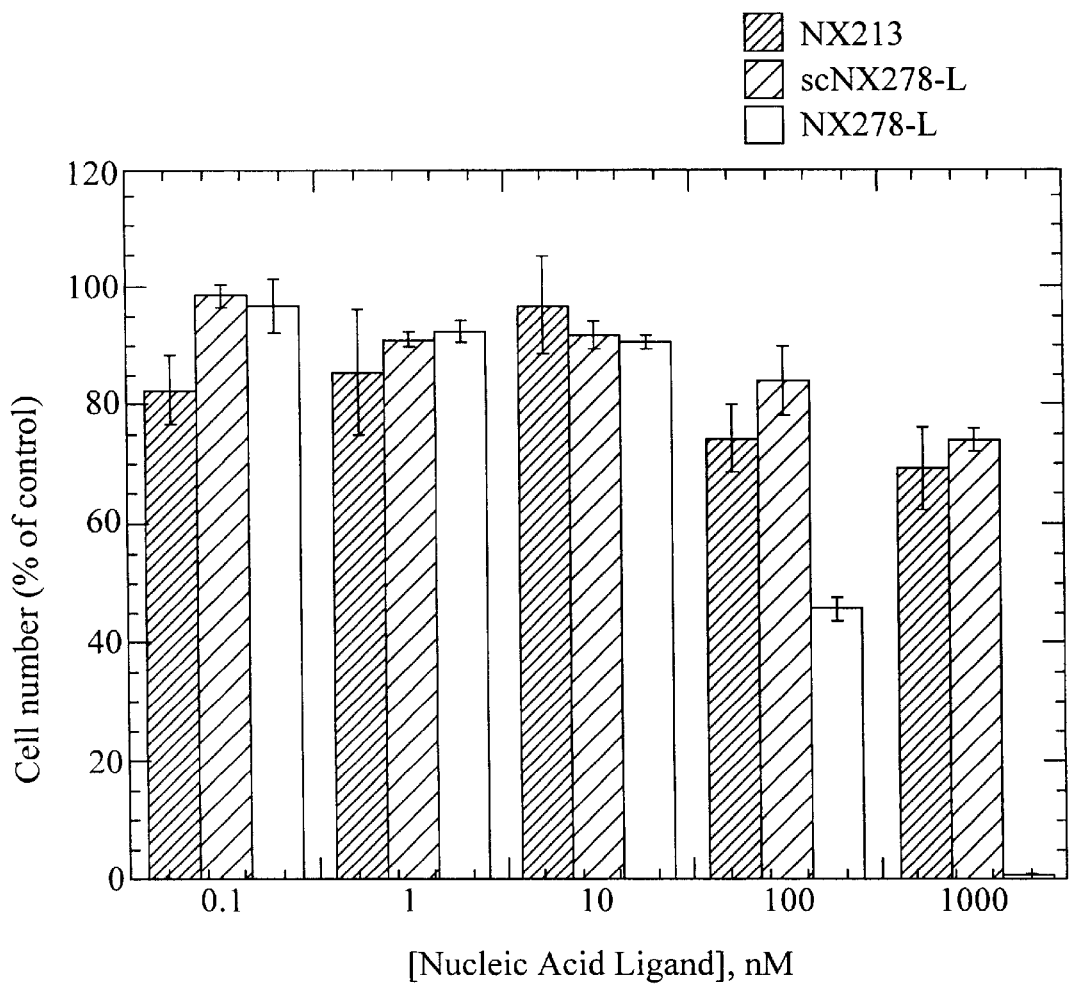
FIG. 4 shows that NX278-L inhibits KS cell growth. Growth of KSY-1 cells in the presence of various concentrations of NX213, NX278-L and scNX278 -L. KSY-1 cells were seeded in 24 well plates at a density of $1 \times 10^4$ cells/well on day 0. Fresh medium treated identically was replaced on days 1 and 3. The cell numbers were determined by trypsinization of cells on day 5 or 6 of culture using particle coulter counter. The experiments were done in triplicates several times. Results shown are the average and SE of representative experiment.

The effects of NX278-Liposome, scNX278-Liposome and NX213 on the proliferation of KS cells was examined. KS cell line KSY-1 was plated in 24-well gelatin coated plates at a density of 7,500–10,000 cells per well on day zero in medium containing RPMI 1640 supplemented with 2% FCS, L-glutamine, penicillin and streptomycin. Nucleic Acid Ligands were added at concentrations between 0.1 nM to 1 μM in fresh medium on day 1, 2, and 3 and the cell count was performed on day 4. NX278-Liposome inhibited the proliferation of KS cells with an IC50 of 100 nM; at 1 M NX278-Liposome, the growth of these cells was completely inhibited. scNX278-Liposome and NX213 exhibited IC50 values of >1 μM (FIG. 4).

NX278-Liposome Inhibits KS Cell Growth in vivo

Figure 5A:
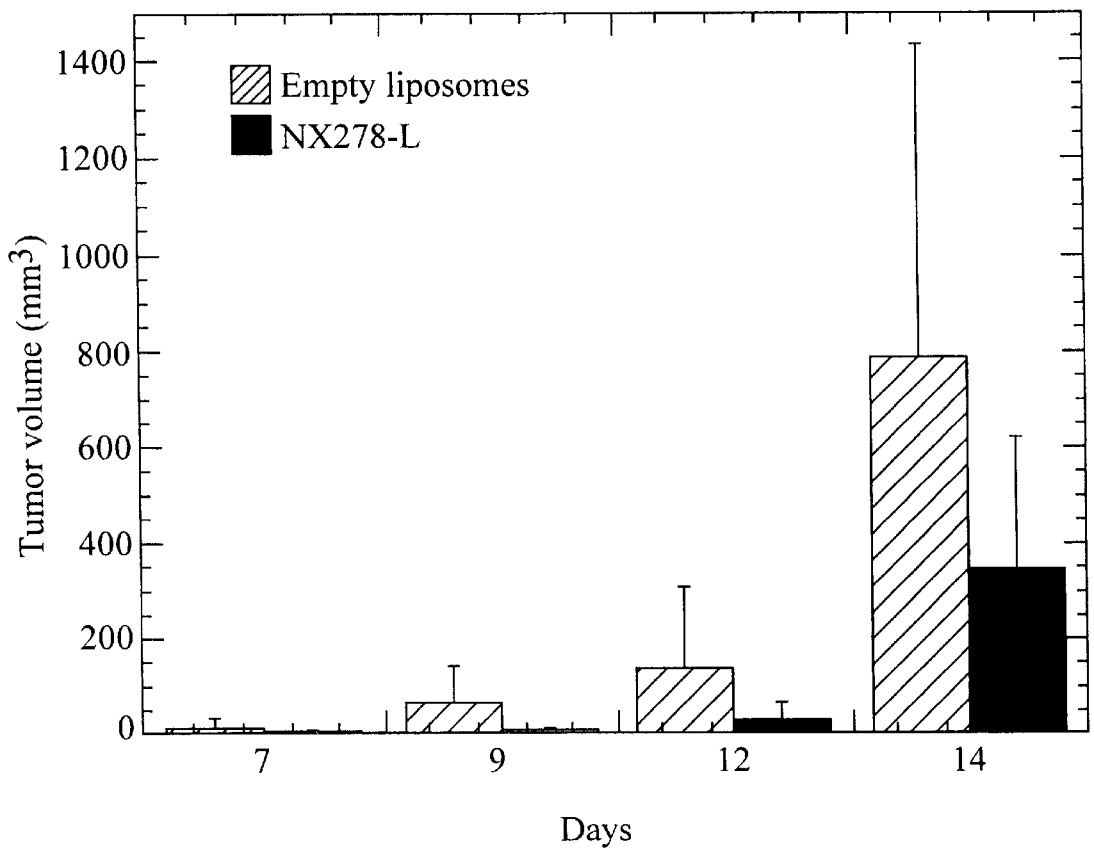
FIGS. 5A and 5B show that NX278 inhibits KS cell growth in athymic mice. Athymic mice were implanted with KS tumor behind the forelegs on day 1. Mice were treated with NX278-L (50 μg/day/mouse, FIG. 5A and 150 μg/day/mouse, FIG. 5B) by intraperitoneal injection daily for five days beginning on day 2. Control mice were treated with empty liposomes using the same quantity of lipids as the Nucleic Acid Ligand treated group. The tumor sizes were measured over the period of two weeks. The tumors were removed on day 14 and measured.
Figure 5B:
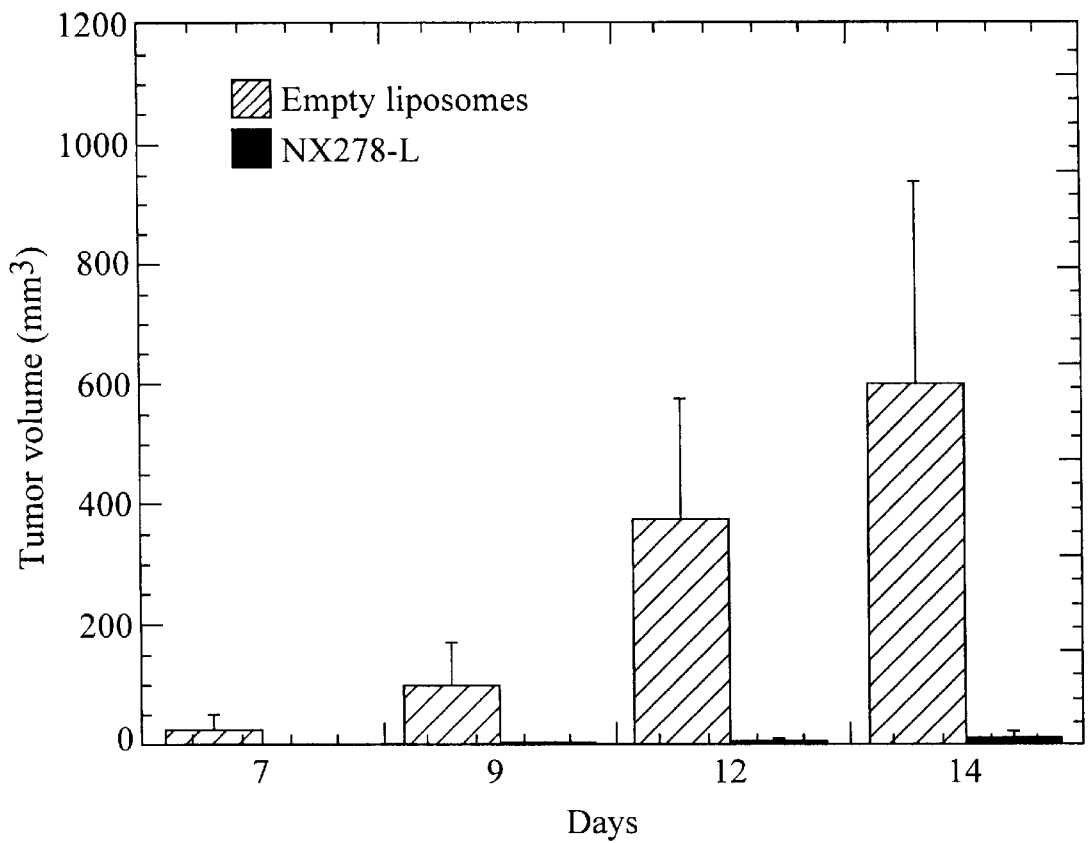

Because VEGF is a growth factor for KS cells, the effect of VEGF anatagonists on KS tumors in vivo is likely to be two-fold: inhibition of paracrine growth effect of VEGF on tumor associated endothelial cells and inhibition of autocrine growth effect on tumor cells. KS tumors may thus be particularly sensitive to VEGF antagonists. To test the activity of the Nucleic Acid Ligands in vivo, tumor trocars (3 mm$^3$) were implanted in athymic mice on day one and treated for five consecutive days beginning on day two with 50, 100 or 150 μg/day/mouse. The rate of tumor growth was measured for a period of two weeks. NX278-Liposome inhibited the tumor growth in a dose dependent manner with very little inhibition of tumor growth at the lowest dose level of 50 μg/day/mouse dose (FIG. 5A), and marked inhibition of tumor growth at both 100 and 150 μg/day/mouse dose levels (FIG. 5B, 150 μg/day/mouse shown). Empty liposomes (FIGS. 5A, B), scNX278-Liposome as well as NX213 and NX278 were ineffective at all doses examined. In addition, NX278-Liposome blocked the VEGF-induced fluid leakage from blood vessels.

Example 3

Experimental Procedures for 2'-Fluoro Pyrimidine-Modified RNA Ligands to VEGF

This example provides general procedures followed and incorporated in Example 4 for the evolution of 2'-Fluoro-modified Nucleic Acid Ligands to VEGF.

Materials

Recombinant human VEGF$_{165}$ purified from the insect cell-line Sf21 was purchased from R & D Systems as a carrier-free lyophilized powder. The protein was resuspended in phosphate-buffered saline to a concentration of 10 μM and stored at −20° C. in small aliquots until use. Aliquots were stored at 4° C. for up to 4 weeks after thawing. Sf21-expressed mouse VEGF$_{164}$, and *E. coli*-expressed human VEGF$_{121}$, VEGF/PlGF heterodimer, and PlGF were also purchased from R & D Systems as carrier-free, lyophilized preparations.

Oligonucleotides were purchased from Operon Technologies, Inc. or were synthesized using an Applied Biosystems Model 394 oligonucleotide synthesizer according to optimized protocols. 2'-F-and 2'-OMe-ribonucleotide phosphoramidites were prepared by JBL Scientific, Inc. (San Luis Obispo, Calif.). 2'-F-pyrimidine NTPs were also purchased from JBL. 2'-OH-purine NTPs and dNTPs were from Pharmacia Biotech, Piscataway, N.J.

*T. aquaticus* thermostable DNA polymerase (Taq polymerase) was purchased from Perkin Elmer-Cetus, (Foster City, Calif.); AMV reverse transcriptase (AMV RT) was from Life Sciences, Inc.; Klenow DNA polymerase was from New England Biolabs, Beverly, Mass. T7 RNA polymerase was from Enzyco, Inc. (Denver, Colo.). Sequenase DNA polymerase is produced by United States Biochemical Corp. (Cleveland, Ohio.).

α-[$^{32}$P]-ATP and γ-[$^{32}$P]-ATP were obtained from New England Nuclear (Boston, Mass.).

The SELEX Protocol

The SELEX procedure has been described in detail in the SELEX Patent Applications. Chemically synthesized DNA oligonucleotide libraries ("30N7" and "40N7") were prepared with randomized regions of 30 or 40 nucleotides flanked by common 5' and 3' fixed sequences (5'-TAATACGACTCACTATAGGGAGGACGATGCGG(30 or 40 N) CAGACGACTCGCCCGA-3'; SEQ ID NO: 133 and 134). Italicized nucleotides at the 5' end of each template correspond to the T7 RNA polymerase promoter sequence. Oligonucleotide primers were also synthesized for use in template preparation and amplification, and reverse transcription: 5'-TCGGGCGAGTCGTCTG-3' ("3N7"; SEQ ID NO: 135) and 5'-TAATACGACTCACTATAGGGAGGACGATGCGG-3' ("5N7" SEQ ID NO:136). Double-stranded DNA templates were prepared by annealing primer 3N7 to the 30N7 or 40N7 libraries and extending the primer using Klenow DNA polymerase or AMV RT. The higher temperature of incubation used for AMV RT (45° C. rather than 37° C.) may better promote complete extension through highly structured template oligonucleotides. The libraries were transcribed using T7 RNA polymerase in the presence of 1 mM each 2'-OH-ATP and GTP, 3 mM each 2'-F-CTP and UTP, and 50 μCi α-$^{32}$P-ATP. RNAs were purified from denaturing polyacrylamide gels by excising the gel slice containing the RNA, crushing it, and soaking for an extended time in 2 mM EDTA.

The SELEX process of affinity selection followed by selected pool amplification has been described in detail (See the SELEX Patent Applications). In brief, one round of selection and amplification was performed as follows: VEGF was mixed with a 5- or 10-fold excess of RNA in phosphate-buffered saline with 1 mM $MgCl_2$ (PBSM) (30N7 and 40N7 libraries) or in Tris-buffered saline, 1 mM $MgCl_2$, 1 mM $CaCl_2$ (TBSMC) (30N7 library only), and the mixture was serially diluted by three. After incubation at 37° C. for 15 minutes, the mixtures were passed through 0.45μ Type HA filters (Millipore) to collect complexes of VEGF with RNA. RNAs were eluted from selected filters by incubation in 2:1 phenol, pH 7:7 M urea. After precipitation from the aqueous phase, RNAs were annealed to primer 3N7 and reverse transcribed using AMV RT. The resultant cDNAs were amplified with 15 cycles of the polymerase chain reaction (PCR) using the 3N7 and 5N7 primers and Taq DNA polymerase. Transcription of the PCR product yielded a new library enriched for sequences with affinity for VEGF. At round 4, a substantial background filter-binding signal in the absence of VEGF had emerged in all three selected RNA pools. To deplete the pools of filter-binding RNAs, rounds 5 and 6 were performed with an alternative scheme for partitioning VEGF-bound RNAs from unbound molecules: after incubation of the RNA pool with the growth factor, each mixture was applied to an 8% polyacrylamide, non-denaturing gel and electrophoresed at 10 W for 45–60 minutes at 4° C. VEGF/RNA complexes migrated above the unbound RNA in this system and were visualized by exposure of X-ray film to the gel. For these rounds, selected RNAs were purified by the crush and soak method, as described above. After twelve rounds of selection and amplification, individual molecules in the selected pools were cloned using the pCR-Script Direct Cloning kit from Stratagene (La Jolla, Calif.). Plasmids were purified using the alkaline lysis method (PERFECTprep Plasmid DNA kit, 5 Prime→3 Prime, Boulder, Colo.) and sequences of the cloned regions were obtained using the Dye Terminator Cycle Sequencing kit available from Perkin Elmer (Foster City, Calfi.). Fluorescent sequencing ladders were read at the National Jewish Center, laboratory of Brian Kotzin, Denver, Colo. Sequences were grouped into families and aligned by eye.

Measurement of Binding Affinities

Nucleic Acid Ligands radiolabeled during transcription by incorporation of α-[$^{32}$P]-labeled NTPs, or after synthesis using γ-[$^{32}$P]-ATP and T4 polynucleotide kinase, were incubated in low concentration (between 20 and 71 pM) with varying concentrations of VEGF or other growth factors at 37° C. for 15 minutes. Incubations were in TBS, PBS, or HEPES-buffered saline (HBS), pH 7.4, with or without the addition of supplemental divalent cations. Samples were passed through prewashed 0.45μ Type HA filters (Millipore) followed by a 5–10 ml wash with binding buffer. Filters were immersed in scintillant and counted to quantitate the amount of protein-bound RNA retained by each filter. The equilibrium dissociation constant ($K_D$) of Nucleic Acid Ligand binding to a specific protein was calculated from the data points as described in Green et al. (1996) Biochem. 35:14413–14424.

Affinity Selection of Nucleic Acid Ligand Fragments

Ten pmol internally-radiolabeled transcripts of high affinity VEGF Nucleic Acid Ligands were partially digested with S7 nuclease to generate a mixture of radiolabeled fragments. One-tenth of the fragmented RNA was incubated with 10 pM VEGF in 45 ml binding buffer, prior to filtration through nitrocellulose. Selected fragments recovered from the filter were run out on a high resolution denaturing polyacrylamide gel next to a lane loaded with the unselected fragment pool. The smallest selected bands were individually purified from the gel and further labeled at their 5' ends with polynucleotide kinase to increase their specific activity. One-half of the sample was annealed to a cDNA of the original transcript and extended to the end of the template using Sequenase DNA polymerase. Comparison of the migration of the purified fragment and its extension product to a standard sequencing ladder was used to determine the probable size and position of the selected fragment within the original transcript. Synthetic oligonucleotides corresponding in sequence to the affinity selected fragments were prepared to verify that the truncated Nucleic Acid Ligand retained affinity for VEGF.

2'-OMe-substitution

The 2'-OMe substitution experiments were performed essentially as described in Green et al. (1995) Chem. Biol. 2:683–695. Three or four libraries were prepared for each of three truncated ligands (t22, t2, t44) in which five or six 2'-OH-purine positions were partially 2'-OMe-substituted. Each purine position was partially 2'-OMe-modified in only one of the libraries. Each 5'-radiolabeled library was incubated with VEGF, and substituted oligonucleotides bound by the protein were collected on nitrocellulose filters. The selected pool and the starting unselected library were partially hydrolyzed by alkali and the products were displayed on a high resolution polyacrylamide gel. A "band intensity ratio" was determined for each purine position by dividing the phosphorimage signal obtained from hydrolysis at that position in the selected pool by the signal obtained for the same position in the unselected library. Band intensity ratios that fall well above the range for a particular position are indicative of a bias for 2'-OH (against 2'-OMe) in the affinity selected pool.

Binding Rate Constants

A small amount (typically less than 1 pmol) of 5'-radiolabeled Nucleic Acid Ligands were incubated with 1 nM VEGF at 37° C. in 1 ml buffered saline supplemented with divalent cations. At time "zero," 50 μl were filtered through nitrocellulose to determine the fraction of RNA bound to protein, then an excess (100 or 500 nM in different experiments) of unlabeled Nucleic Acid Ligand was added and 50 μl aliquots were filtered at time points thereafter. Filters were counted in scintillant to determine the amount of radiolabeled RNA still bound to VEGF at each time point. The data, plotted as fraction of RNA bound (f) vs time, was fitted to an equation for exponential decay:

$$f(t)=f_0 e^{-kt}+b,$$

where $f_0$ is the fraction of RNA bound at time zero, k is the dissociation rate constant ($k_d$) and b is the residual binding of radiolabeled RNA to the filter at the end of the experiment (effectively, in the absence of protein). Association rate constants ($k_a$s) were calculated from the measured $k_d$ and $K_D$ values according to the equation:

$$k_a=k_d/K_D$$

Example 4

2'-Fluoro-modified RNA Ligands to VEGF
Selection of Ligands

Ligands to VEGF were isolated in three separate SELEX experiments from libraries of 2'-F-pyrimidine-modified RNAs containing 30 or 40 random nucleotides. Selections were performed in PBS supplemented with 1 mM $MgCl_2$ (30N and 40N libraries) or in Tris-buffered saline with 1 mM $MgCl_2$ and 1 mM $CaCl_2$ (30N library only). Approximately $10^{14}$ unique sequences were included in the first selection cycle of each experiment. After ten cycles, the affinity between VEGF and each RNA pool had improved approximately 1000-fold relative to the starting pools. As no further improvement in binding affinity was observed after two additional cycles, individual members of the twelfth round pools were cloned and sequences were determined for about 50 isolates from each selection.

Oligonucleotide ligands to $VEGF_{165}$ were isolated in three separate SELEX experiments. Individual clones were isolated and sequenced and the sequences grouped into families based on shared primary structural motifs (Table 2). The name of each ligand indicates the target (V=VEGF), the selection buffer (P=PBS; T=TBS), the length of the randomized region in the library (30 or 40 nucleotides) and the clone number (following the decimal). The frequency with which a sequence appeared among the clones analyzed is indicated in parentheses; sequences that differed by only one nucleotide were attributed to PCR mutagenesis of a common precursor and were grouped together with the variable base indicated in the sequence by the appropriate symbol (Y=U or C). The fixed sequences common to all ligands are shown in lower case letters at the top. For individual clones the sequence of the variable region is shown in upper case. For some ligands, fixed region sequences in lower case are appended to the variable region sequence where they contribute to possible secondary structures. The high affinity Kd for binding to VEGF is shown for each ligand. One ligand in each family was selected for further analysis (gray box).

Of a total of 143 clones analyzed, 76 sequences differing by more than one nucleotide were obtained. 44 of these sequences could be grouped into three major families based on conserved primary structural motifs (Table 2). Sequences that may be grouped in minor families with five or fewer members and "orphan" sequences that were unique among the isolates are shown in Table 6. Ligands containing the primary structural motif defined by Families 1 and 2 arose in all three affinity selections. Similarities between the conserved primary structures of both families suggest that they may also share similar secondary structures and/or that they may interface with VEGF using similar contact regions. Members of Family 2 share the possibility of forming a short basepaired stem enclosing the conserved sequence motif in a large "loop" (underlined in Table 2). With the exception of the closing AXU basepair, the sequence identity of bases in the putative stem regions is not conserved. Such "covariation" of bases that conserves secondary rather than primary structure supports the existence of the putative stem and suggests that this structure may be important for the high affinity conformation of this family of VEGF ligands. No similarly conserved basepairing interactions were detected among Family 1 sequences. A third family of ligands arose only in the selections performed in TBSMC (Family 3, Table 2). In addition to a highly conserved primary structure motif, in all members of this family, sequences 3' of the conserved region share basepairing complementarity to nucleotides in the 5' fixed region (underlined in Table 2). Since, for most of the ligands, the bases on the 5' side of the putative stem cannot be said to covary with their basepairing partners, this observation is less predictive of a common secondary structure; nevertheless, our initial guess for a minimal high affinity sequence derived from this family (described below) was guided by the strong conservation of this motif. The affinities of the individual RNA ligands for VEGF were estimated based on a single determination of the $K_D$ for their interaction. With few exceptions, the ligands showed very high affinity for the growth factor, with $K_D$s between 5 and 50 pM.

Minimal Ligands

The shared primary and secondary structural motifs that define each sequence family hint at the minimal sequence elements required for high affinity binding to VEGF. Nested truncations of a representative ligand from each family (indicated by gray boxes in Table 2) were produced by chemical synthesis and their relative affinities for VEGF were determined (Table 3). Truncated versions of ligands VP30.22, VP30.2 and VT30.44 were prepared by chemical synthesis and their affinities for VEGF were determined as described in Example 3. Initial truncations (t22, t2, t44) were further refined by synthesis of oligonucleotides with additional bases lacking from the 5' and/or 3' ends. In order to initiate the chemical synthesis, the 3'-most nucleotide of several of the ligands was modified either by substitution of 2'-OH-cytidine for 2'-F-cytidine (underlined) or by addition of a 3'-3'-linked deoxythymidine "cap" (asterisks). The length of each oligonucleotide (minus the cap) and its high affinity $K_D$ for binding to VEGF are shown.

An initial prediction for the minimal sequence from clone VP30.22 (Family 1) was made by mapping the ends of a purified, affinity-selected fragment of the full-length ligand (see Example 3). This 29 nucleotide molecule ("t22") showed an approximately three-fold loss in binding affinity for VEGF relative to the full length ligand. Further truncation at the 3' end of this molecule caused a precipitous loss in affinity but up to 6 additional nucleotides could be removed from the 5' end with little or no consequence (Table 3). For clone VP30.2 from Family 2 and clone VT30.44 from Family 3, truncated ligands "t2" and "t44" were synthesized that encompassed the putative five basepair stem and all of the conserved sequence motif. Both truncated ligands retained nearly all of the binding activity of the full length molecule. Further truncation by deleting one putative basepair at a time (one nucleotide from each end of the ligand) caused a gradual loss in affinity. Thus, for these sequences, truncations based on possible secondary structures predicted very well the minimal high affinity ligand, and further supports the hypothesis that the putative stems contribute to the high affinity conformation of these ligands.

2'-OMe Modification

Substitution at the 2'-OH positions of RNA oligonucleotides by 2'OMe has been observed to improve their stability against nucleases present in rat urine as well as in other biological fluids. Stabilization of oligonucleotides to nucleases is likely to be critical to their success as therapeutic or diagnostic agents. Unfortunately, 2'-OMe-modified nucleoside triphosphates are not generally accepted as substrates by RNA polymerases under standard reaction conditions. However, 2'-OMe purines may be introduced into a specific oligonucleotide by chemical synthesis. It has been observed that some high affinity 2'-OH purine RNA ligands will accept a surprisingly high percentage of 2'-OMe purine substitutions with little loss of affinity for the target protein.

To identify those purine positions for which 2'-OMe substitution is compatible with high affinity binding to VEGF, several syntheses of ligands t2, t22 and t44 were prepared in which five or six purines at a time were partially substituted with the modified nucleotide (described in Example 3). Affinity selection of each partially substituted library was used to isolate those molecules that retained substantial affinity for VEGF. In such an affinity selected pool, positions that do not tolerate substitution are biased for 2'-OH and thus show higher sensitivity to hydrolysis by alkali relative to the same position in the unselected library. 5'-radiolabeled unselected and affinity selected pools were partially hydolysed by alkali and the products were displayed on a high resolution polyacrylamide gel. In ligand t22, G10 and A12 showed substantial bias for 2'OH in the affinity selected pool, as did A6 and G21 in ligand t2, and A5 and A6 in ligand t44. While the foregoing analysis identifies those positions that are likely to disallow substitution with 2'OMe nucleotides, one cannot predict from these data how simultaneous modification of all other purines will affect binding affinity. In fact, ligand t22, synthesized with all 2'-OMe-purines except G10, A12 and G22 (which showed a marginal preference for 2'-OH), bound to VEGF with an affinity equal to if not better than the all 2'-OH-purine sequence (Table 4).

Truncated oligonucleotides (t22, t2, and t44) were chemically synthesized with all but one, two or three purine positions substituted with 2'-OMe-purines. The remaining 2'-OH-purines are indicated in each ligand name and are shown in bold in the ligand sequence. $KD_S$ for the binding of each substituted ligand to VEGF are shown. Further substitution at G22 had little effect on binding to VEGF, but incorporation of 2'-OMe at G10 or A12, as predicted, was detrimental to binding affinity. Similarly, ligands t2 and t44 tolerated 2'-OMe-substitution at all but two purines with a three- to four-fold impact on the affinity of the Nucleic Acid Ligand for VEGF (Table 4).

Binding Affinities and Rate Constants for Substituted Truncates

In the hope of identifying highly 2'-substituted VEGF Nucleic Acid Ligands of minimal length, all 2'-OMe-substitutions that did not dramatically decrease binding were incorporated into truncated ligands t22c, t2a, and t44a (see Table 3). 2'OH nucleotides are indicated in bold, and 2'OMe nucleotides are indicated in plain text. The resultant Nucleic Acid Ligands, t22-OMe and t44-OMe, bound to VEGF with KDS of 67 pM and 49 pM, respectively, while ligand t2OMe bound with a KD of approximately 140 pM (Table 5). These KDS compare favorably with that of NX-213 ($K_D$=140 pM), a 2'-$NH_2$-pyrimidine-, 2'-OMe-purine-substituted oligonucleotide inhibitor of VEGF described previously (see U.S. patent application Ser. No. 08/447,169, which is incorporated herein by reference). Each of the truncated 2'-OMe-substituted oligonucleotides was found to compete with NX-213 and with one another for binding to VEGF.

Dissociation rate constants ($k_d$) were determined for each of the three 2'-OMe-substituted ligands by following the loss of a preformed complex between radiolabeled ligand and VEGF upon the addition of a large excess of unlabeled ligand. Ligand t22-OMe showed the fastest rate of dissociation with a half life of approximately 60 seconds. Ligands t2-OMe and t44-OMe showed slightly slower rates of dissociation with half lives on the order of 170 and 90 seconds, respectively. Association rate constants ($k_a$), calculated from the equilibrium dissociation constant and the dissociation rate constant ($K_D=k_d/k_a$), ranged from $3\times10^7$ to $2\times10^8$ $M^{-1}$ $sec^{-1}$ (Table 5). Such rapid rates of association suggest a near diffusion limited binding interaction between these ligands and VEGF, and are in line with the association rate constants observed for SELEX-derived Nucleic Acid Ligands to other targets.

Divalent Cation Dependence

Ligands in Families 1 and 2 were selected in the presence of magnesium cations while Family 3 ligands were selected in a buffer containing both magnesium and calcium. Since divalent cations may contribute to RNA/protein interactions through nonspecific or specific stabilization of high affinity RNA structures, we asked whether magnesium and/or calcium were required for the high affinity binding of representative ligands to VEGF. The affinities of Nucleic Acid Ligands t22-OMe and t2-OMe (from Families 1 and 2, respectively) were unchanged in the presence or absence of supplemental divalent cations or the chelating agent EDTA (data not shown). However, Family 3 ligands, as represented by ligand t44-OMe, showed an absolute dependence on the presence of calcium for high affinity binding to VEGF. Binding was dramatically reduced ($K_D>10^{-7}$) when divalent cations in the binding buffer were replaced with EGTA. The addition of excess $MgCl_2$ to divalent-cation-depleted binding buffer gave no improvement in binding affinity, but $CaCl_2$, in two-fold molar excess over EGTA, fully restored binding activity. Identical binding behavior was observed for the unmodified ligand t44 (data not shown).

Protein Specificity

The oligonucleotides described here were selected based on their affinities for $VEGF_{165}$, the larger of two diffusible isoforms of the growth factor. $VEGF_{121}$, the smaller isoform, lacks one of the exons in $VEGF_{165}$ and, unlike the latter, does not bind to heparin. None of the three truncated, 2'-OMe-substituted oligonucleotides bound with any measurable affinity to $VEGF_{121}$. Furthermore, the native structure of $VEGF_{165}$ is essential for the binding of all three Nucleic Acid Ligands, as no binding is observed when the protein is reduced with DTT prior to incubation with the oligonucleotides.

VEGF is a highly conserved protein across species, the human $VEGF_{165}$ and mouse $VEGF_{164}$ isoforms showing 88% sequence identity. The truncated, 2'-OMe-substituted ligands bound equally well to human and murine VEGF. However, no binding was observed for any of the ligands to homodimers of PlGF, a placenta-derived protein that shares 53% sequence identity with VEGF across the conserved platelet derived growth factor-like domain. Heterodimers between VEGF and PlGF have recently been isolated from the supernatants of both normal and tumor-derived cell lines, and such heterodimers show activity in binding to one of two high affinity VEGF receptors and in inducing responses in cultured endothelial cells. The biological relevance of VEGF/PlGF heterodimers is unknown. Substantial binding, though with greatly reduced affinities, was observed with VEGF/PlGF heterodimers. These data may indicate that the Nucleic Acid Ligands bind at or near the interface between the two subunits in a dimer and that PlGF does not present all of the contact sites necessary for high affinity binding. Alternatively, the structure of the VEGF subunit may be altered by participation in a heterodimer with PlGF with consequent distortion of the Nucleic Acid Ligand binding surface.

Example 5

Synthesis of Phospholipid, Glycerol Amide Lipid, and PEG-modified VEGF Nucleic Acid Ligands Three different formulations were used for the synthesis of various Lipophilic Compound/Nucleic Acid Ligand Complexes as follows:

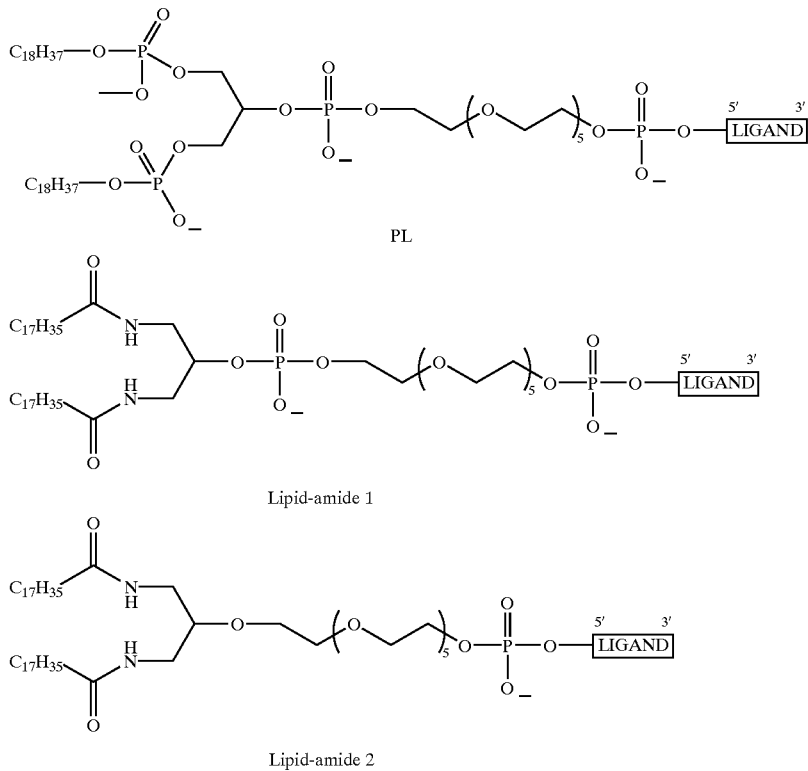

PL

Lipid-amide 1

Lipid-amide 2

1. C-18 Phosphoramidite for the Synthesis of PL Formulation

An outline for the preparation of C-18 phosphoramidite is shown in Scheme 3. 1-Octadecanol was phosphorylated under standard condition. After work up the reaction mixture, the residue was purified on silica gel column with hexane:ethyl acetate:triethylamine (90:10:5) to offer 21.5 g of pure product (57% yield).

Scheme 3

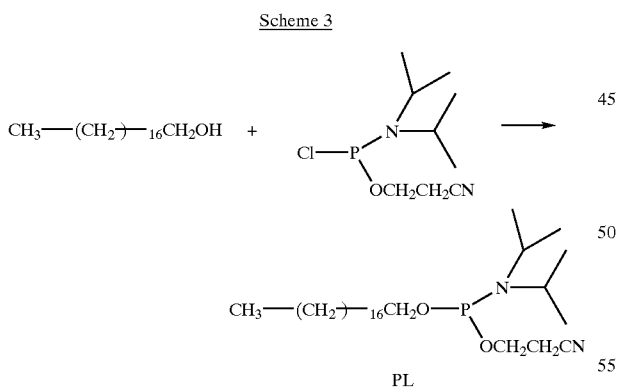

PL

II. Synthesis of Lipid Amide 1

This phosphoramidite, unlike the above PL, has amide linkages. The structure of the oligo resulting from conjugation of this lipid is shown below. Several experiments demonstrated that the high insolubility of compound 22 in organic solvents made NMR and MS characterization and further phosphitylation of compound 22 to DAG amidite 23 impossible, however, from the results for preparation of Lipid-spacer amidite (Scheme 3), we expected the phosphylation of compound 22 with chloro-(2-cyanoethoxy)-N,N-diisopropylamino-phosphine might go if the mixture was refluxed. The approach to prepare the DAG amidite is shown in Scheme 4.

Scheme 4

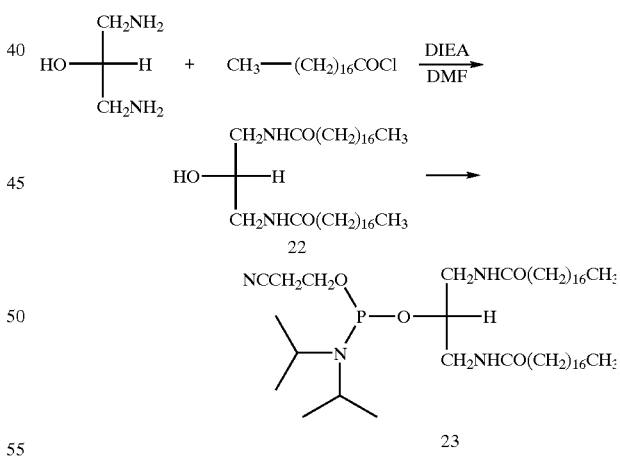

N,N'-Bis(stearoyl)-1,3-diamino-2-propanol (22) (2)

A solution of stearoyl chloride (6.789 g, 22.41 mmol) in $ClCH_2CH_2Cl$ (50 mL) was added dropwise to a solution of 1,3-diamino-2-hydroxy propane (1.0 g, 11.10 mmol) in $ClCH_2CH_2Cl$ (100.0 mL) and TEA (2.896 g, 22.41 mmol) with stirring at R.T. After finishing addition, the mixture was heated to 70° C. overnight, a clear solution was formed, and the solution was cooled to R.T., filtered, and the solids were washed with $CH_2Cl_2$, $CH_3OH$, 5% $NaHCO_3$ and ethyl ether, and dried in vacuo to give 22 (6.40 g, 93% yield) as white solids. $^1$H NMR (pyridine-d$_5$; 60° C., δ, ppm): 3.82–3.78 (m, 1H), 2.37 (t, J=7.5 Hz, 4H), 1.81–1.76 (m, 4H), 1.30–1.27 (m, 60H), 0.87 (t, J=5.7 Hz, 6H).

N,N'-Bis(stearoyl)-O-(diisopropylamino-2-cyanoethoxyphosphinyl)-1,3-diamino-2-propanol (23)

To compound 22 (5.80 g, 9.31 mmol), dried overnight in vacuo, was in anhydrous CH$_2$Cl$_2$ (150.0 mL) and N,N-diisopropylethylamine (4.2 mL, 18.62 mmol) was injected. The mixture was cooled in an ice-water bath and chloro-(2-cyanoethoxy)-N,N-diisopropylamino-phosphine (8.6 mL, 0.47 mmol) was injected. After stirring for 30 min, the mixture was heated at 60° C. for 90 min. After cooling to R.T. insoluble materials were filtered and the solution was washed with 5% NaHCO$_3$ and brine, dried over Na$_2$SO$_4$, and concentrated in vacuum. The crude product was purified by precipitation from CH$_3$CN to afford pure product (4.65 g, 61% yield) as white solids. $^{31}$P NMR (CDCl$_3$, ppm): 154.04.

1. Synthesis of DAG-Spacer Amidite, Lipid Amide 2

Hexa(ethylene glycol) was incorporated into the llipid amidite in order to alleviate the insolubility of diamide compound 22, which is a immediate intermediate to lipid amidite 23. An outline of the preparation of lipid-spacer amidite 29 is shown in Scheme 5. The coupling step of compound 25 with 1,3-diamino-2-hydroxypropane and potassium t-butoxide in THF did not go well, and the yield was only about 20%. One attempt to improve yield was made by reacting 25 and diamide 22, however, no desired product was detected.

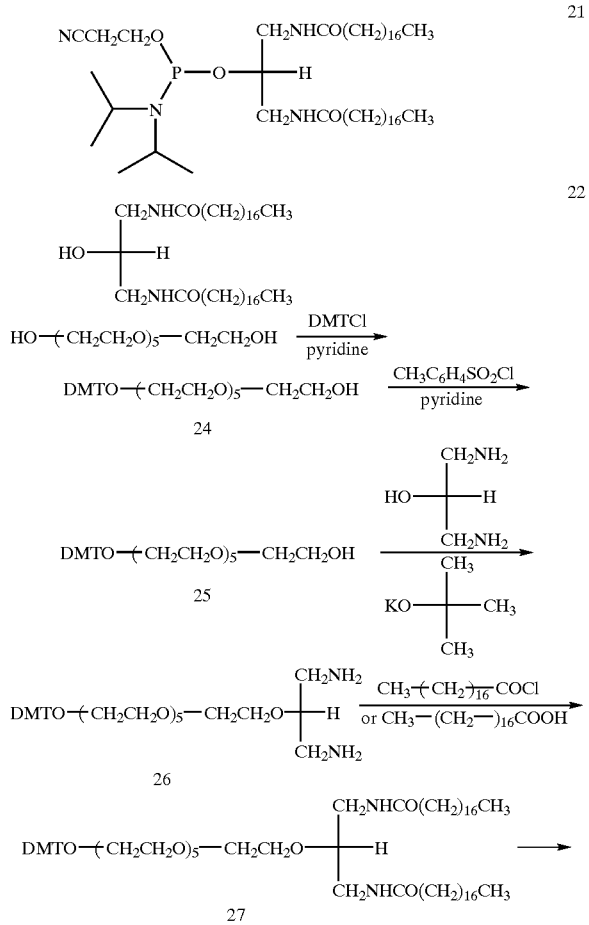

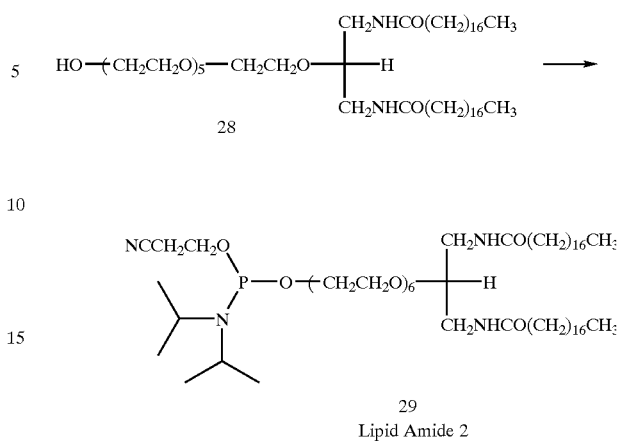

Lipid Amide 2

(4,4'-Dimethoxytrityloxy)-hexaethylene glycol (24)

Hexa(ethylene glycol)(18.93 g, 67.05 mmol) was coevaporated with anhydrous pyridine (3×50 mL), dissolved in anhydrous pyridine (400 mL), and, after cooling to 0° C, DMTrCl (23.85 g, 70.40 mmol) in pyridine (50 mL) was added dropwise during 30 min with stirring under Ar. The reaction mixture was kept at R.T. overnight. The pyridine was removed under high vacuum and the residue was dissolved in CH$_2$Cl$_2$, which was washed with 5% NaHCO$_3$ and brine, dried over Na$_2$SO$_4$, and concentrated in vacuum. The crude product was purified by wet-flash silica gel column chromatography in a gradient of ethyl acetate, then CH$_2$Cl$_2$ and methanol (95/5) containing 0.5% TEA. The appropriate fractions were combined, evaporated, and dried in vacuum to give 24 (26.1 g, 66.6% yield) as a light yellow oil. $^1$H NMR (DMSO-d$_6$; δ, ppm): 7.40 (d, J=7.2 Hz, 2H), 7.33–7.24 (m, 7H), 6.89 (d, J=8.9 Hz, 4H), 4.61 (t, J=5.1 Hz, 1H), 3.73 (s, 6H), 3.05 (m, 24H); $^{13}$C NMR (DMSO-d$_6$; δ, ppm): 158.02, 145.02, 135.78, 129.67, 128.13, 127.71, 126, 61, 113.14, 85.29, 72.33, 72.27, 70.06, 69.87, 69.80, 69.75, 69.70, 62.84, 60.25, 60.19, 55.01.

(4,4'-Dimethoxytrityloxy)-hexaethylene glycol tosylate (25)

To an ice cooled solution (0° C.) of 24 in anhydrous pyridine (50 mL), was added a solution of toluene sulfonyl chloride in pyridine (30 mL). After 2 h at R. T., the solution was evaporated to a light yellow oil. The residue was taken-up in CH$_2$Cl$_2$ and washed with 5% NaHCO$_3$ and brine, dried over Na$_2$SO$_4$, filtered and evaporated in vacuo. The product was purified by wet-flash silica gel chromatography, eluting with ethyl acetate to give the product (4.08 g, 93% yield) as light yellow oil. $^1$H NMR (DMSO-d$_6$; δ, ppm); 7.78 (d, J=8.3 Hz, 2H), 7.46 (d, J=8.1 Hz, 2H), 7.40 (d, J=7.4 Hz, 2H), 7.32–7.23 (m, 7H), 6.88 (d, J=8.8 Hz, 4H), 4.09 (t, J=4.3 Hz, 2H), 3.72 (s, 6H), 3.06 (m, 22H), 2.40 (s, 3H); $^{13}$C NMR (DMSO-d$_6$; δ, ppm): 158.01, 145.01, 135.78, 132.38, 130.12, 129.67, 128.12, 128.02, 127.80, 127.70, 127.62, 113.13.

2-(4,4'-Dimethoxytrityloxy)-hexaethylene glycol-1,3-diaminopropane (26)

A mixture of 1,3-diamino-2-hydroxypropane (747 mg, 8.28 mmol) and potassium t-butoxide (2.78 g, 24.84 mmol) in anhydrous THF was heated to 70° C. for 2 h and then cooled to R.T. Compound 25 (4.08 g, 5.25 mmol) in THF was injected, and the mixture was stirred at 70° C. overnight until TLC showed on more 25 was left. After the solution was cooled to R.T., THF was removed in vacuo, and 25 mL of CH$_2$Cl$_2$ and 25 mL water were added. The CH$_2$Cl$_2$ layer was separated, and the water later was extracted with CH$_2$Cl$_2$. The CH$_2$Cl$_2$ solutions were combined, dried over Na$_2$SO$_4$ and evaporated under reduced pressure. The crude product (2.43 g) was directly used for reaction without further purification. $^1$H NMR (DMSO-d$_6$; δ, ppm): 7.41 (d, J=7.7 Hz, 2H), 7.32–7.21 (m, 7H), 6.87 (d, J=8.8 Hz, 4H), 3.73 (s, 6H), 3.52–3.40 (m, 24H), 3.17 (s, 1H), 3.07–3.02 (m, 4H).

N,N'-Bis(stearoyl)-2-(4,4'-dimethoxytrityloxy)-hexaethyleneglycol-1,3-diaminopropane (27)

A solution of stearoyl chloride (3.363 g, 11.1 mmol) in ClCH$_2$CH$_2$Cl was injected to a solution of 26 in ClCH$_2$CH$_2$Cl and TEA (1.9 mL, 11.1 mmol) with stirring at R.T. The mixture was kept at R.T. for 2 h, then heated to 70° C. overnight. After the solution was cooled to R.T., the solution was washed with 5% NaHCO$_3$ and brine, dried over Na$_2$SO$_4$, and concentrated in vacuum. The crude product was purified by wet-flash silica gel column chromatography in a gradient of ethyl acetate and CH$_2$Cl$_2$ (50/50) and then ethyl acetate and methanol (50/50). The second fraction was collected, evaporated, and dried in vacuum to give 27 (640 mg) as a light yellow solid. $^1$H NMR (DMSO-d$_6$; δ, ppm): 7.40 (d, J=7.2 Hz. 2H), 7.37–7.20 (m, 7H), 6.74 (d, J=8.9 Hz, 4H), 3.71 (s, 6H), 3.63–3.51 (m, 24H), 3.17 (s, 1H), 3.16–3.13 (m, 4H), 2.12 (t, J=7.3 Hz, 4H), 1.18 (m, 60H), 0.80 (t, J=6.2 Hz, 6H).

N,N'-Bis(stearoyl)-2-hexaethylene glycol-1,3-diaminopropane (28)

A mixture of compound 27 (640 mg), 2.5% DCA solution in CH$_2$Cl$_2$ (5 mL) and trihexylsilane (2 mL) was stirred at R.T. until orange color turned to pale color. After removal of CH$_2$Cl$_2$, the residue was repeatedly precipitated from hexane to give a light yellow solid (210 mg, 63% yield). $^1$H NMR (CDCl$_3$, δ, ppm): 3.3.69–3.59 (m, 24H), 3.17 (s, 1H), 3.06–3.01 (m, 4H), 2.21 (t, J=7.9 Hz, 4H), 1.18 (m, 60H), 0.81 (t, J=6.3 Hz, 6H).

N,N'-Bis(stearoyl)-2-(diisopropylamino-2-cyanoethoxyphosphinyl-hexaethylene glycol)-1,3-diaminopropane (29)

Compound 28 (210 mg, 0.237 mmol), dried overnight in vacuo, was dissolved in anhydrous CH$_2$Cl$_2$ (5.0 mL) and N,N-diisopropylethylamine (218 μL, 1.25 mmol) was added. The solution was cooled in an ice-water bath and chloro-(2-cyanoethoxy)-N,N-diisopropylamino-phosphine (106 μL, 0.47 mmol) was injected. After stirring for 30 min, the reaction mixture was diluted with CH$_2$Cl$_2$ and washed with 5% NaHCO$_3$ and brine, dried over Na$_2$SO$_4$, and concentrated in vacuum to afford compound 29 $^{31}$P NMR (CDCl$_3$, ppm): 154.04.

Conjugation of 20K or 40K PEG NHS ester to VEGF Nucleic Acid Ligands

General procedure: VEGF oligonucleotide was exchanged for Triethylammonium salt and lyophilysed. The crude oligonucleotide was dissolved in 100 mM sodium borate buffer (pH 9) to 60 mg /ml concentration. 2 Eq of PEG NHS ester (Shearwater Polymers, Inc.) was dissolved in dry DMF (Ratio of borate:DMF 1:1), and the mixture was warmed to dissolve the PEG NHS ester. The oligonucleotide solution was quickly added to the PEG solution and the mixture was vigorously stirred at room temperature for 10 min. About 90% of the oligonucleotide becomes conjugated to PEG NHS ester. See FIGS. 1H and 1I.

Synthesis of Dimeric VEGF Nucleic Acid Ligands

The dimeric VEGF Nucleic Acid Ligands shown in FIGS. 1J, K, and L were made as follows.

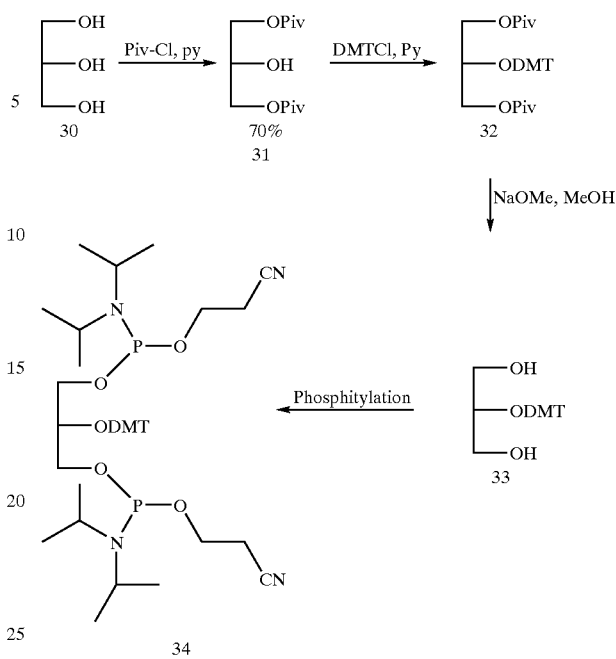

Synthesis of 1,3-Dipivalolyl-2-O-dimethoxy tritylglycerol 32

To a stirred pyridine solution of compound 31 (62 g of 70% pure product, 200 mmol, in 200 ml of pyridine), prepared according to McGee et al. (1988, Synthetic Communication, 1651), was added dimethoxy trityl chloride (84 g, 240 mmol, 1.2-fold excess) and the reaction was allowed to stir at room temperature for 16 hours. The reaction mixture was concentrated under reduced pressure and the residue was taken in CH$_2$Cl$_2$, (1 L) washed with water, and dried (MgSO$_4$) and concentrated. The crude mixture (130 g) was used as such in the next reaction.

Synthesis of 2-O-dimethoxy trityl glycerol 33

A mixture of crude compound 33 (130 g), NaOMe (28 g) and methanol (900 ml) was heated at 50° C. for 16 h. After the reaction was complete (TLC), the mixture was concentrated to dryness and the residue was dissolved in water and CH$_2$Cl$_2$ (1:1). The organic layer was separated, and the aqueous layer was washed with saturated NH$_4$Cl, water and brine and dried (MgSO$_4$). Evaporation of the solvent afforded a gummy compound, which was purified by silica gel column using 1:1 hexane/ethyl acetate containing 2% TEA to afford compound 33 in 75% isolated yield. $^1$H NMR (DMSO-d$_6$) 3.02–3.07 (m, 2H), 3.17–3.23 (m, 2H), 3.3–3.35 (m, 1H), 3,7 (s, 6H), 4.26 (t, J=4.1 2H, D$_2$O exchangeable), 6.59–6.86 (m, 4H), 7.17–7.68 (m, 9H).

Synthesis of Bisamidite 34

To an ice cold stirred solution of the alcohol 3 (16.2 g, 41.1868 mmol) in CH$_2$Cl$_2$ (125 ml) and diisopropyl ethylamine (58 ml, 320 mmol) was added phophitylating reagent (20.5 ml, 90.62 mmol) and the solution was slowly warmed up to rt and stirred for 2 h at the same temperature. The reaction mixture was slowly poured into crushed ice and extracted with CH$_2$Cl$_2$, washed with 5% NaHCl$_3$, water and brine and dried. Residue obtained after evaporation of the solvent was purified by silica gel column chromatography using 1:1 Hexane/ethyl acetate containing 2% TEA to afford compound 34 in 70% yield. $^1$H NMR DMSO-d$_6$ 1.03–1.12 (2d, 24H), 2.69–2.75 (2t, 4H), 3.1–3.33 (m, 4H), 3.33–3.55 (m , 5H), 3.66–3.7 (m, 4H), 3.72 (s, 6H), 6.83–6.89 (m, 4H), 7.19–7.48 (m, 9H). $^{31}PD_3PO_4$ as an external standard 153.64 & 153.39 (2S).

Preparation of VEGF Dimers

Synthesis of VEGF dimers was done on 8800 automated DNA/RNA synthesizer. NX31838 was prepared, where rA stands for adenosine, mG and mA stands for 2'-O-methylguanosine and adenosine respectively and fC and fU stands for 2'-deoxy-2'-fluorocytidine and 2'-fluorouridine respectively and [3'-3'] stands for a 3',3'-internucleotidic linkage. The synthesis was carried out at a 1 mmol scale on a Millipore 8800 automated synthesizer using 5'-DMT-2'-O-methyl-N$^6$-tert-butylphenoxyacetyl-adenosine, 5'-DMT-2'-O-TBDMS-N$^2$-tert-butyl-phenoxyacetylguanosine and 5'-DMT-2'-O-TBDMS-N$^6$-tert-butylphenoxyacetyl-adenosine 3'-N,N-diisopropyl-(2-cyanoethyl) phosphoramidites and 2'-deoxy-2'-fluoro-5'-DMT-N4-acetylcytidine and 2'-deoxy-2'-fluoro-5'-DMT-uridine 3'-N,N-diisopropyl-(2-cyanoethyl)-phosphoramidites. The synthesis cycle was as follows. The activator formulations are described in Table 12. The syntheses were carried out using CPG support of 600 Å pore size, 80–120 mesh, and 60–70 μmol/g loading with 5'-succinylthymidine. The coupling cycle is shown in Table 12.

Example 6

Pharmacokinetic Properties of Phospholipid (PL) and PEG Modified VEGF Nucleic Acid Ligands Of the Sequences shown in Table 2, Sequence VT30.44 was chosen for further study and was renamed as NX31838. The pharmacokinetic properties of VEGF Nucleic Acid Ligand NX31838 conjugated to 20 and 40K PEG, were determined in Sprague Dawley rats (see FIG. 1 for molecular descriptions) (SEQ ID NOS:8 and 9). Similar studies were also carried out on NX31838 conjugated to PL lipid as a liposomal formulation and as free drug (see FIGS. 1H and 1 for molecular descriptions) (SEQ ID NOS:8 and 9). In each study the oligonucleotide was diluted in PBS to a solution concentration of 1.0 mg/ml based on UV absorption at 260 mn and an extinction coefficient of 0.037 μg oligo/ml. In all studies, 9 rats received 1.0 mg oligonucleotide/kg animal weight by bolus tail vein injection and plasma samples were taken at various times from 2 minutes to 24 hours. The plasma samples and quality control samples were analyzed using a hybridization assay. The hybridization assay utilized a capture oligonucleotide that contains a complementary sequence to the 5'-end of the VEGF Nucleic Acid Ligand conjugated to an iron oxide (FeO) bead (FeO-spacer-3'-d (GCC TTA GTC ACT T-5') (SEQ ID NO: 137) where spacer=(dT)$_8$), and a detection oligonucleotide containing two biotin molecules at the 5'-end (biotin-biotin-5'-d(spacer-CGG ATG TAT AAG CA-3'), where spacer=(dT)$_8$) (SEQ ID NO: 138). After incubation of the capture and detect probes with a plasma sample containing VEGF Nucleic Acid Ligand NX31838 the amount of the biotin oligonucleotide hybridized to the bead was quantitated with the strepavidin linked alkaline phosphatase, using CSPD-Sapphire as the luminescent substrate.

Figure 6:
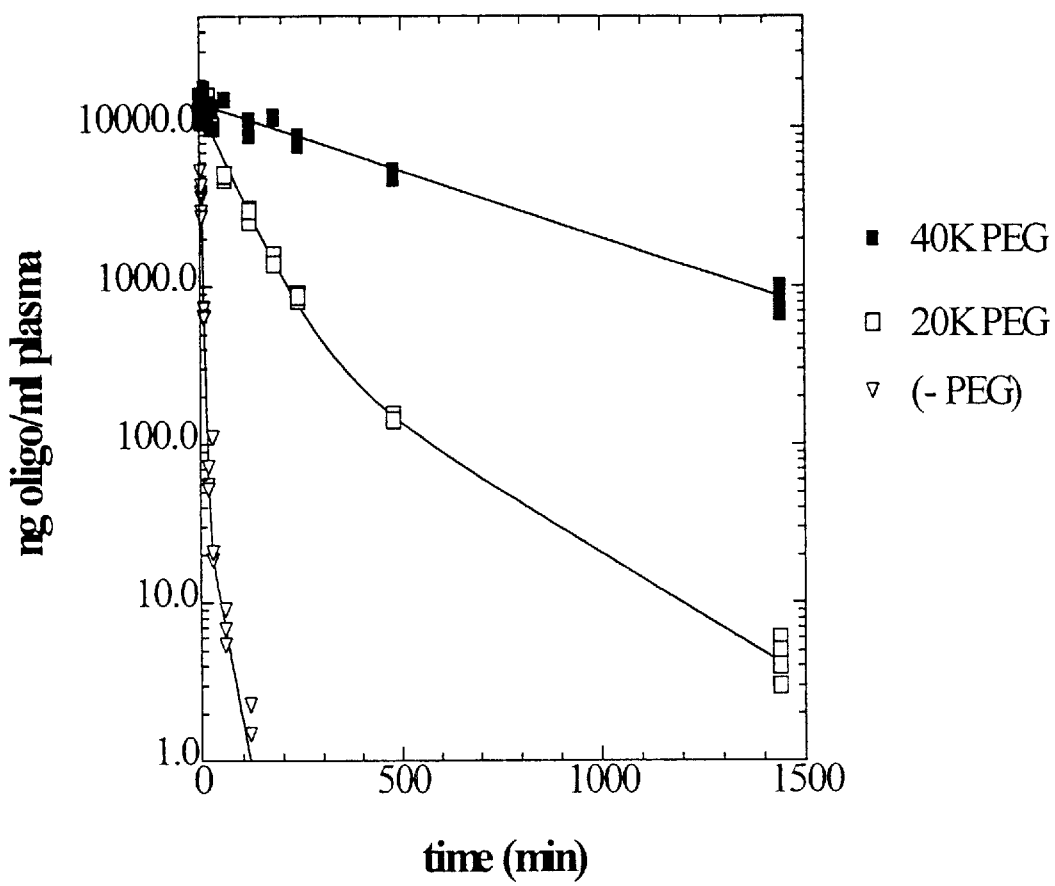
FIG. 6 summarizes the data for the plasma concentration of NX31838 20K PEG (□), 40K PEG (■), and NX31838 (minus PEG) (▽) as a function of time following the bolus injection.

Data for the plasma concentration of the free, PEG20K and PEG40K VEGF Nucleic Acid Ligands (NX31838) (SEQ ID NOS:8 and 9) as a function of time following bolus injection are summarized in FIG. 6. The 40K PEG conjugate was cleared with a monoexponential $t_{1/2}$ of 360 minutes, while the 20K PEG version was cleared much more rapidly with 95% of the Nucleic Acid Ligand being cleared with an alpha $t_{1/2}$ of 49 minutes and 5% being cleared with a beta $t_{1/2}$ of 192 minutes, indicating the apparent importance of size on clearance. Compared with the PEG-conjugated Nucleic Acid Ligands, the free (unconjugated) NX31838 was cleared from plasma very rapidly with a $t_{1/2}$ of several minutes. The plasma concentration of an oligonucleotide as a function of time can be significantly increased by introducing appropriate functional groups into the oligonucleotide.

Figure 7:
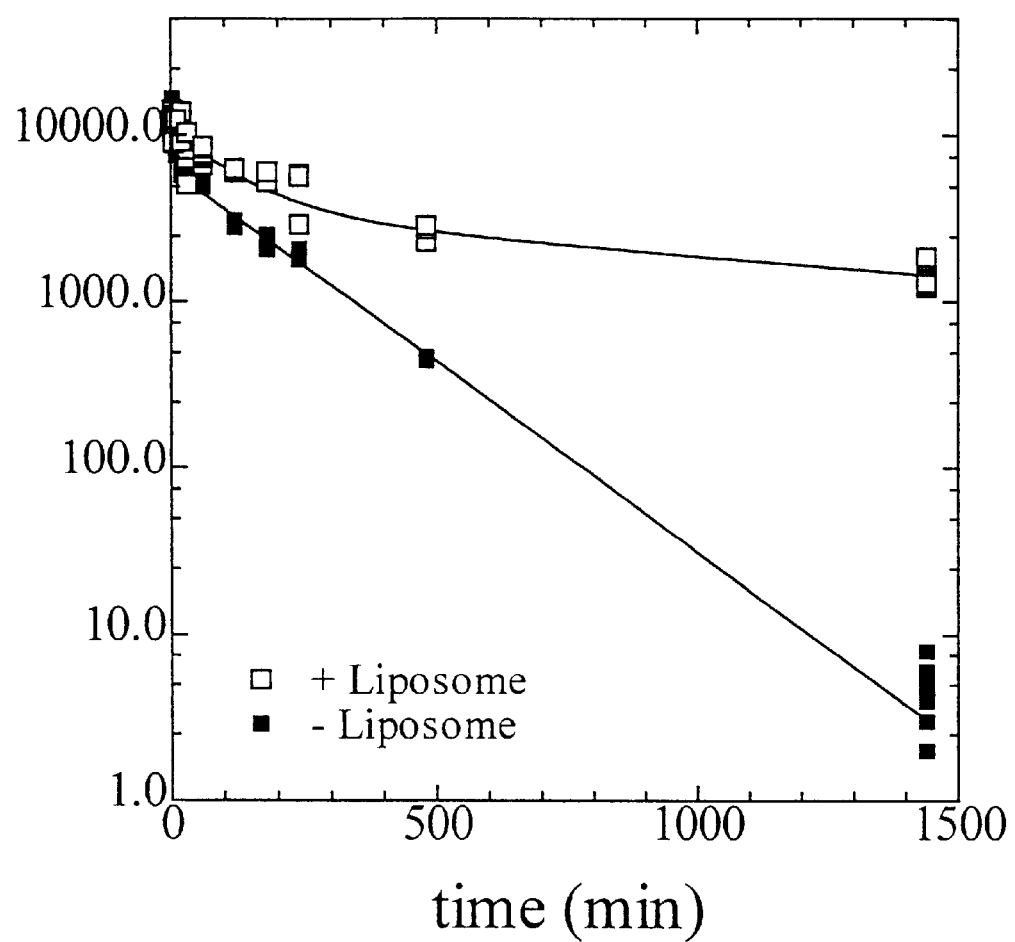
FIG. 7 summarizes the data for the plasma concentration of NX31838 PL as a function of time following the bolus injection.

Data for the plasma concentration of PL lipid conjugated VEGF Nucleic Acid Ligand (SEQ ID NO:5) formulated with and without liposomes as a function of time following bolus injection are summarized in FIG. 7. The liposomes were created as described in Example 7A by sonication in the presence of Nucleic Acid Ligand and contain oligonucleotide on the inside as well as the outside. The liposomal formulation was cleared much more slowly than the free drug, beta $t_{1/2}$ of 1161 minutes and 131 minutes, respectively. The plasma concentration of an oligonucleotide as a function of time can be significantly increased by liposomal formulation.

Example 7

Preparation of NX31838 PL-Liposome Complex

A. Liposome Preparation by Filming

The lipids are combined at a ratio of 2 moles DSPC to 1 mole cholesterol. NX 31838 PL, in water, is added to the lipids at a ratio of 1:50 (w/w). The material is combined by solvating with a solution of chloroform:methanol:water (1:3:1). The solvent is removed by rotary evaporation leaving a heterogeneous film of NX 31838 PL co-mixed with the lipids. The film is rehydrated to 50 mg/mL, based on the lipids, in a solution of 9% sucrose, buffered with 25 mM sodium phosphate at pH 7.4. The solution is mixed vigorously, heated to 65° C. and the resultant white milk-like solution sonicated in 75 mL aliquots to assemble the lipids into unilamellar liposomes. The progress of liposome formation is followed visually until the solution becomes opalescent and then by particle sizing via dynamic light scattering using a particle analyzer (Leeds & Northrup Model Microtrack UPA 150, Horsham, Pa.). Liposome size is in the range of 50 to 70 nm (by volume weight distribution method).

B. Liposome Preparation by Passive Anchoring scNX-278 (see FIG. 1C for molecular description) was tested to see whether it would undergo spontaneous incorporation into pre-formed ("empty") liposomes. Preliminary results using a DEAE assay (for removal of free Nucleic Acid Ligand/glycerol lipid complex) indicated two important findings: 1) loading could be achieved; and, more importantly, 2) essentially complete loading of the Nucleic Acid Ligand/glycerol lipid complex was observed over 24 hours at room temperature. A more detailed study to determine the effects of temperature upon loading was subsequently undertaken. It was observed that temperature had a dramatic effect on the rates of incorporation. Although complete loading could be achieved over 24 hours at room temperature, complete incorporation could be achieved in just minutes at elevated temperatures (67° C.). This proved to be a rapid and efficient method for incorporating Nucleic Acid Ligand/Lipophilic Compound Complex into pre-formed liposomes.

Size-exclusion chromatography was then used to separate free scNX-278 from the liposome-associated form. The preliminary work was conducted using the loading of scNX-278 into "empty" 2:1 DSPC:cholesterol liposomes. Chromatograms were generated using a Superdex S-200 column at 22° C. Over a 22 hour period, the gradual incorporation of the scNX-278 into the empty liposome population was observed as a shift in the peak areas (data not shown). The results correlate well with the data obtained from the DEAE assay.

Studies were also undertaken to determine whether additional scNX-278 could be loaded into sonicated oligo-liposomes. A sonicated preparation of scNX-278 was prepared by co-dissolving oligo-lipid with lipid and co-sonicating the two together. The resulting liposomes showed complete incorporation of the scNX-278. This sonicated preparation was then subjected to 2 separate rounds of passive anchoring with additional free scNX-278 to see whether more scNX-278 could be incorporated successfully. During the first round of passive anchoring, all of the free scNX-278 was passively anchored into the liposomes after incubation for 1 hour at 65° C. The second attempt at passive anchoring of additional scNX-278 resulted in incomplete loading.

The key finding from these experiments is that a Nucleic Acid Ligand/Lipophilic Compound Complex could be passively anchored into sonicated oligo-liposomes at high concentrations, but that the liposome's capacity for absorbing additional Nucleic Acid Ligand/Lipophilic Compound Complexes could be exceeded. After 2 rounds of passive loading (to approx. 3 mg lipid-oligo/50 mg lipid), the liposomes apparently reach their "capacity" to absorb additional oligo-lipid since some free lipid-oligo remains. These data were confirmed by DEAE spin-column analysis (data not shown). The conclusions that can be drawn are: 1) sonicated liposomes possess additional capacity for incorporating Nucleic Acid Ligand/Lipophilic Compound Complexes; and 2) 100% Nucleic Acid Ligand incorporation can be achieved via sonication.

Figure 1E:
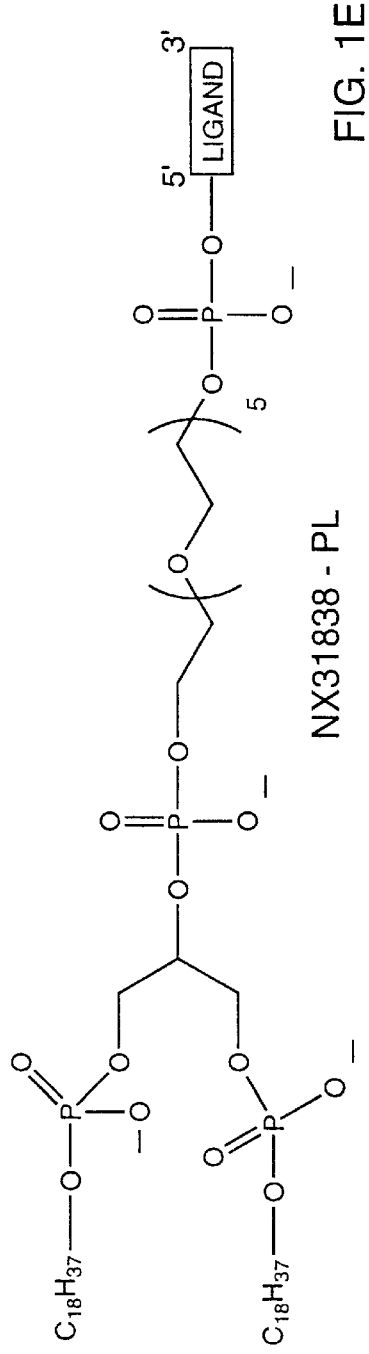
Figure 1F:
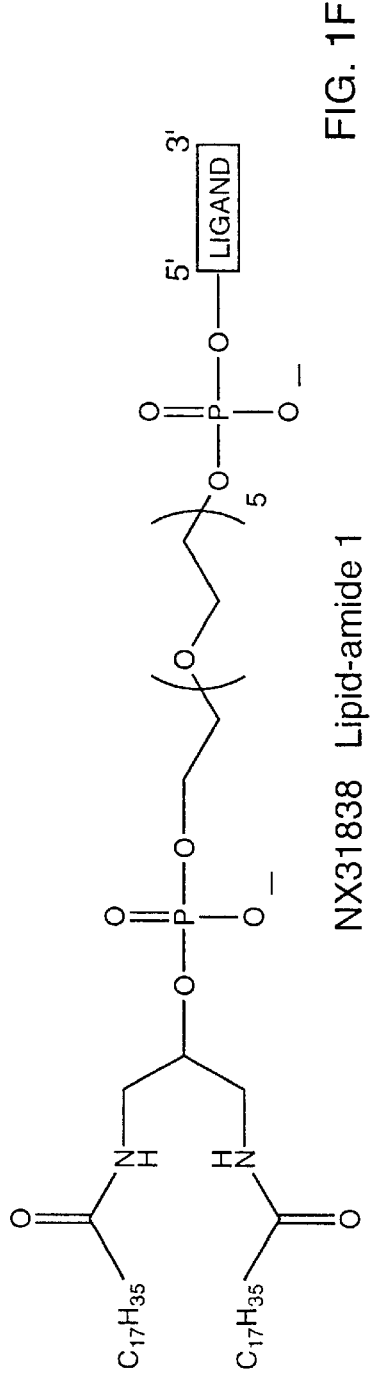
Figure 1G:
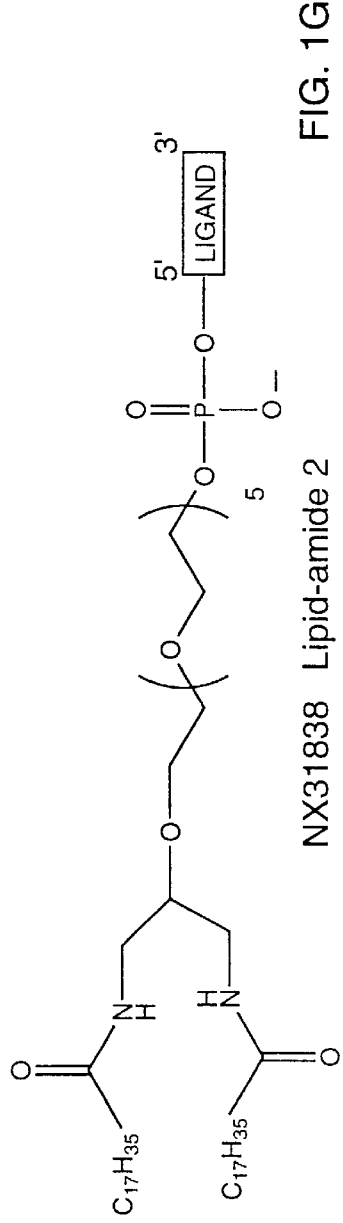

Subsequent studies were conducted on NX31838 PL (see FIG. 1E for molecular description). NX31838 is of significant interest because it has improved pharnacokinetics (see Example 6) and biodistribution against VEGF targets when incorporated in liposomes. Several studies were conducted to better understand the incorporation of NX31838 via passive anchoring into liposomes.

Studies on the kinetics of NX31838 PL indicated that the passive anchoring for this molecule was so rapid as to be considered impossible to measure via any of the chromatography techniques known in the literature (all which require a minimum of several minutes of run time).

In order to determine the orientation of the NX31838 PL molecule (i.e., whether the Nucleic Acid Ligand component was projecting externally from the Liposome, or projecting into the Liposome aqueous center), externally introduced RNase was used to selectively cleave any of the Nucleic Acid Ligand Component that was projecting externally from the Liposome. In the case of passively anchored NX31838 PL liposomes, all of the Nucleic Acid Ligand is exposed to RNAse I. No additional digestion was observed following Triton X-100 treatment. These results indicate that the passively loaded NX31838 PL is oriented such that the Nucleic Acid Ligand Component is projecting externally from the Liposome. If the passively anchored NX31838 PL liposomes are pre-digested with RNAse I, then run over a DEAE column approximately 99% of the Nucleic Acid Ligand is captured by the column, whereas if the same sample is run over DEAE but without pre-incubation with RNAse I, nearly 100% of the oligo is able to pass through the column, unbound to the DEAE. Liposome protects the oligo from DEAE. The Liposome acts to protect the Nucleic Acid Ligand Component from DEAE, since it associates with the Nucleic Acid Ligand with high affinity, greatly reducing its exposure to the DEAE groups.

Finally, as part of developing new methods to separate free Nucleic Acid Ligand/Lipophilic Compound Complex from the liposome-anchored form, we digested NX31838.05 PL with RNase I. The cleaved oligo could be easily separated using size exclusion chromatography (S-1000 resin) following removal of the lipid tail, whereas the intact Nucleic Acid Ligand/Lipophilic Compound Complex co-eluted with liposomes under identical conditions. This data indicates that the Nucleic Acid Ligand/Lipophilic Compound Complex is probably forming a micelle when free in solution. This results in it co-eluting in the void volume of the column with the liposomes. Removal of the lipid tail allows it to enter the gel filtration media and hence be sized and stored appropriately.

Example 8

In Vivo Efficacy of VEGF Nucleic Acid Ligand Complexes—Dermal Vascular Permeability Assay The ability of several different formulations of the NX31838 Nucleic Acid Ligand to attenuate VEGF-induced changes in the permeability of the dermal vasculature (Miles Assay) was performed as previously described (Senger et al. (1986) Cancer Research 46:5629–5632) with minor modifications. Briefly, adult female guinea pigs (3/study) were anesthetized with isoflurane and the hair on the dorsal and lateral back areas was removed with clippers. Evans Blue dye (2.5 mg/guinea pig) was administered intravenously. Injection solutions (PBS, VEGF, NX31838 formulations, and anti-VEGF monoclonal antibody) were prepared 30 min in advance, co-mixed where indicated, with final concentrations as shown. Each solution shown was then injected intradermally (duplicate injections/guinea pig; 40 µl/site) in a randomized manner in a grid pattern drawn on the clippered area. Guinea pigs were allowed to recover from anesthesia and were sacrificed by $CO_2$ exposure 30 min after completion of the intradermal injections. The skin was then harvested, trimmed free of subcutis, and transilluminated. Images were then captured using a color CCD camera (Hitachi Denshi KP-50U, Japan) and Image-Pro Plus software (Version 3.1, Media Cybernetics, Silver Springs, Md.). Each skin sample was normalized for intensity with each injection site analyzed for optical density and the area involved.

Figure 8A:
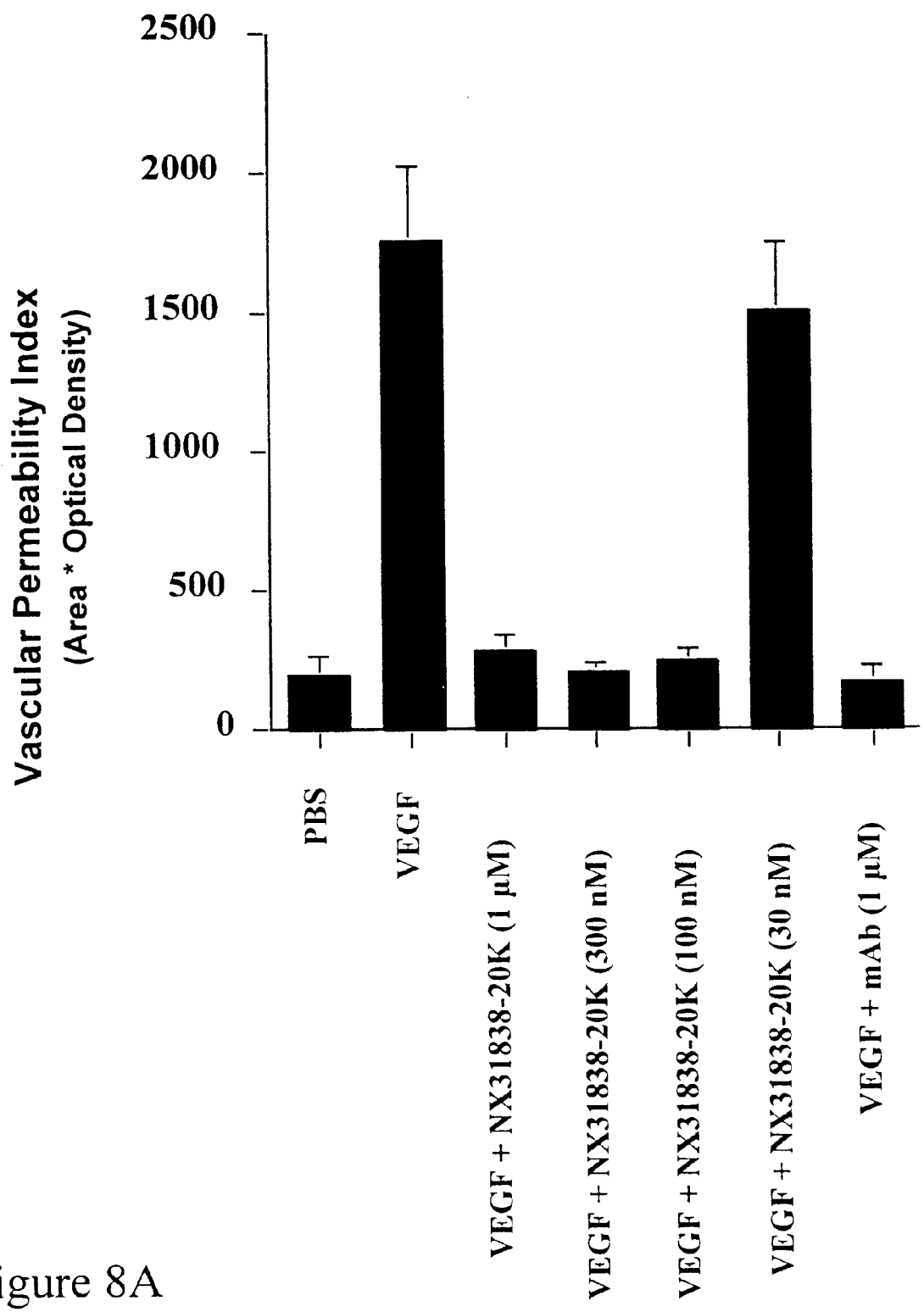
FIGS. 8A–8D show changes in vascular permeability elicited by intradermal injection of VEGF protein (0.8 pmol)±Nucleic Acid Ligand/monoclonal antibody as indicated. Local extravasation of Evans blue dye was determined 30 min after injection by transillumination of harvested skin. FIGS. A, B, C, and D show the effect of co-mixing NX31838-20K PEG, NX31838-40K PEG, NX31838-PL, or NX31838d2-40K PEG with protein 30 min prior to injection. Values are mean±SEM. *$P<0.05$ compared with VEGF alone. See FIG. 1 for molecular descriptions.
Figure 8B:
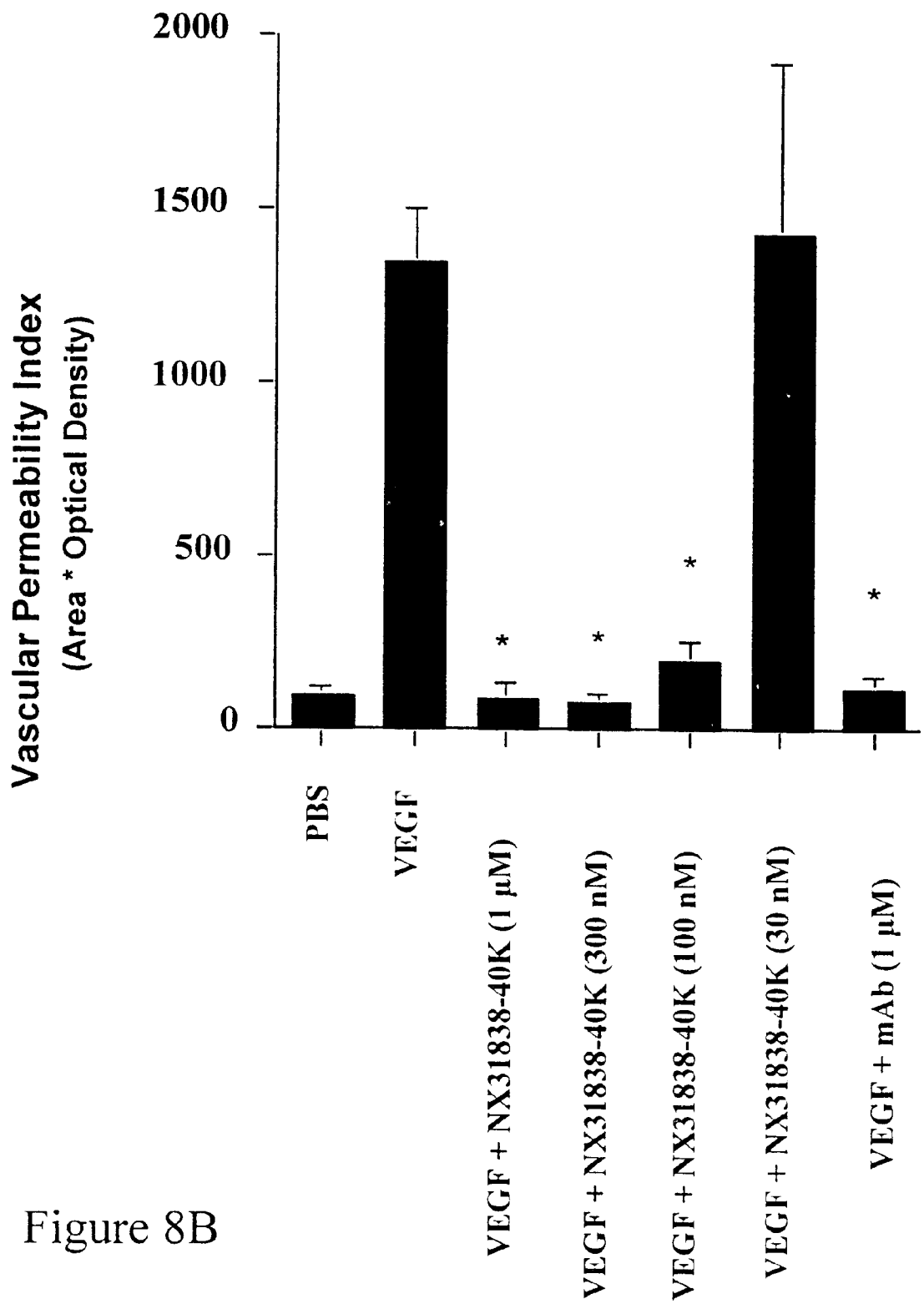
Figure 8C:
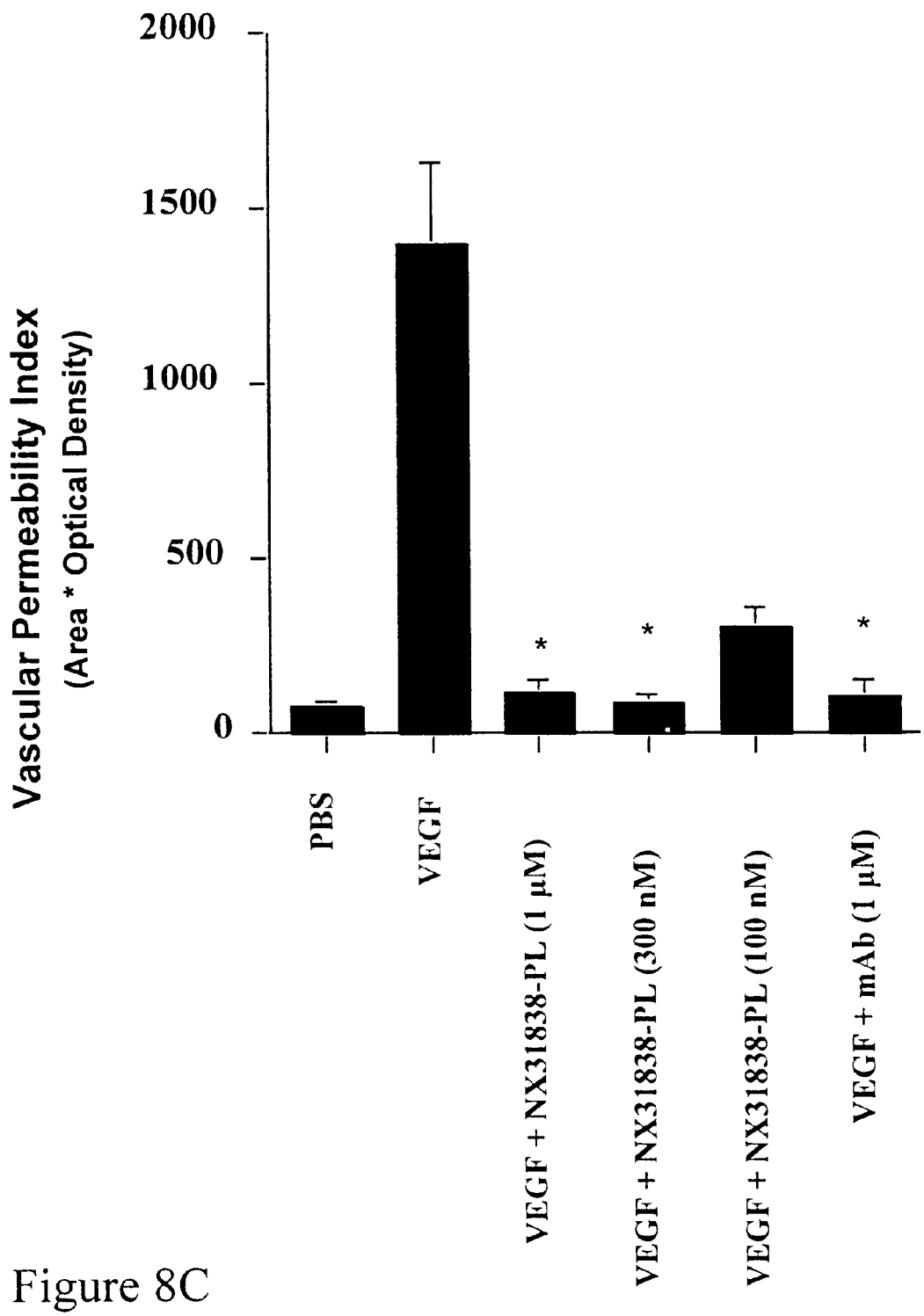
Figure 8D:
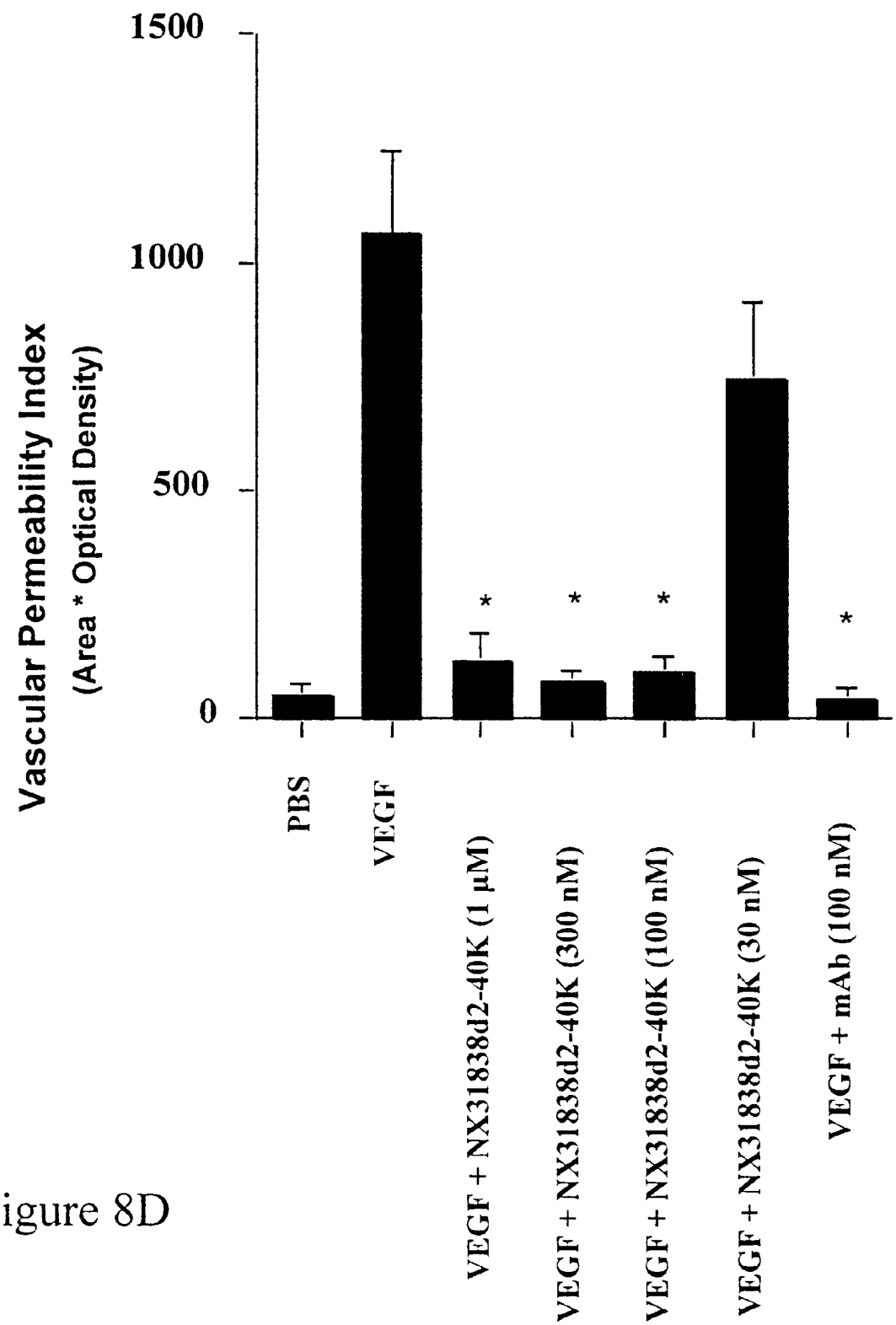

Panels A–C from FIGS. 8A–C show the results of Nucleic Acid Ligand attenuation of VEGF-induced vascular leakage for NX31838-20K PEG, NX31838-40K PEG, NX31838-PL in liposomal preparation as described in Example 7A. All formulations were able to significantly reduce vascular leakage down to or near PBS control levels with concentrations as low as 100 nM. At 30 nM the blocking effect of the Nucleic Acid Ligand was lost. The NX31838-PL liposomal formulation was not evaluated at this concentration but appeared to have reduced blocking activity at 100 nM. The anti-VEGF monoclonal antibody was also evaluated in this model system and was likewise effective down through 100 nM with loss of activity at 30 nM. Thus, suggesting that in this model system that NX31838 in the various formulations examined is equally effective as antibody in blocking one of the functional effects of VEGF protein.

Example 9

In Vivo Efficacy of VEGF Nucleic Acid Ligand Complexes—Corneal Pocket Model

VEGF Nucleic Acid Ligand (NX31838) formulations were tested in their ability to reduce VEGF-induced corneal angiogenesis in the normally avascular rat cornea. Briefly, biopolymer (Hydron) pellets±VEGF protein (3 pmol) were prepared approximately 30 hr before by adding the protein or carrier solution to 12% biopolymer in 95% ethanol. Adult, Sprague-Dawley rats (200–240 g) were anesthetized by intraperitoneal injection of ketamine HCl (50 mg/kg) and xylazine (10 mg/kg). The left eye was then prepared by topical administration of tetracaine HCl for local anesthesia followed by application of dilute povidone-iodine solution and subsequent rinsing with isotonic saline solution. A vertical partial thickness incision was made in the mid-cornea. A mid-stromal pocket was dissected caudally toward the lateral canthus extending to within 1.5 mm of the limbus. A pellet was then inserted into and pushed to the caudal limit of the pocket. Residual air was gently massaged out of the pocket. A drop of chloramphenicol ophthalmic solution was then applied to the eye. The animal was rolled over and the procedure repeated on the right eye with insertion of the same type of pellet. Upon completion of pellet insertion in each eye, each animal was then administered either PBS (volume matched to Nucleic Acid Ligand formulation group) or Nucleic Acid Ligand (10 mg/kg) intravenously twice daily as indicated. At 5 days, each animal was anesthetized and photographs were taken using a 35 mm camera (Minolta X9) mounted on a dissecting microscope (KAPS, Germany). Each eye was evaluated for the angiogenic response by measuring the maximum length of vessel growth (0–5), the density of vessel growth (1–4) adjacent to the implanted pellet, and the circumference of the eye with angiogenesis occurring (0–1). An angiogenic index was then determined as the product of length * density * circumference.

Figure 9A:
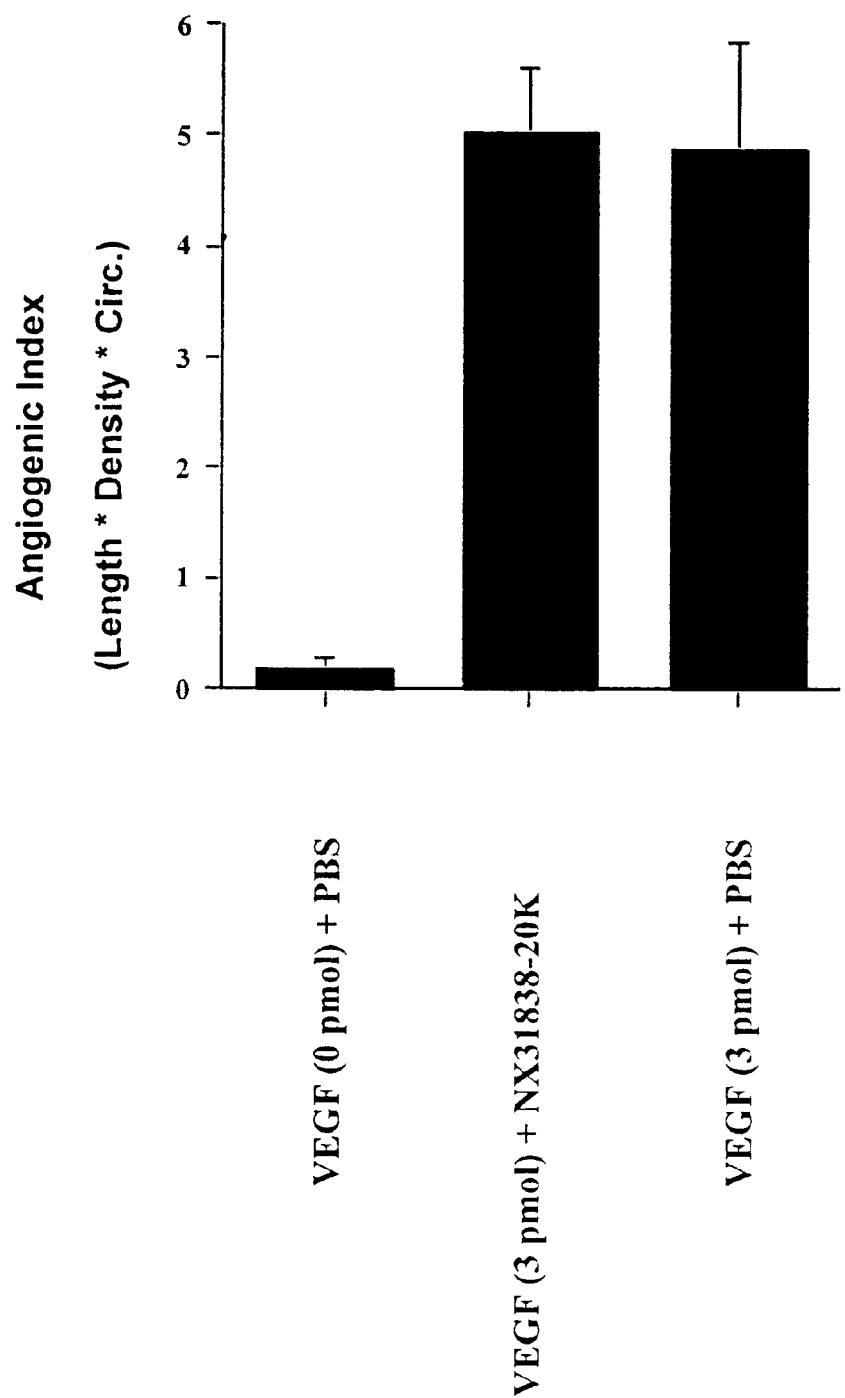
FIGS. 9A–9C show the evaluation of Nucleic Acid Ligand attenuation of VEGF-induced corneal angiogenesis. Zero or three pmol of VEGF protein were incorporated in a biopolymer (Hydron) and implanted in the corneal stroma. Animals were treated intravenously twice daily with either PBS or Nucleic Acid Ligand as indicated for 5 days. FIGS. A, B, and C illustrate the effect of systemic treatment with NX31838-20K PEG, NX31838-40K PEG, or NX31838-PL Nucleic Acid Ligand on neovascularization. Values are mean±SEM. * $P<0.05$ compared with 3 pmol VEGF+PBS group. See FIG. 1 for molecular descriptions.
Figure 9B:
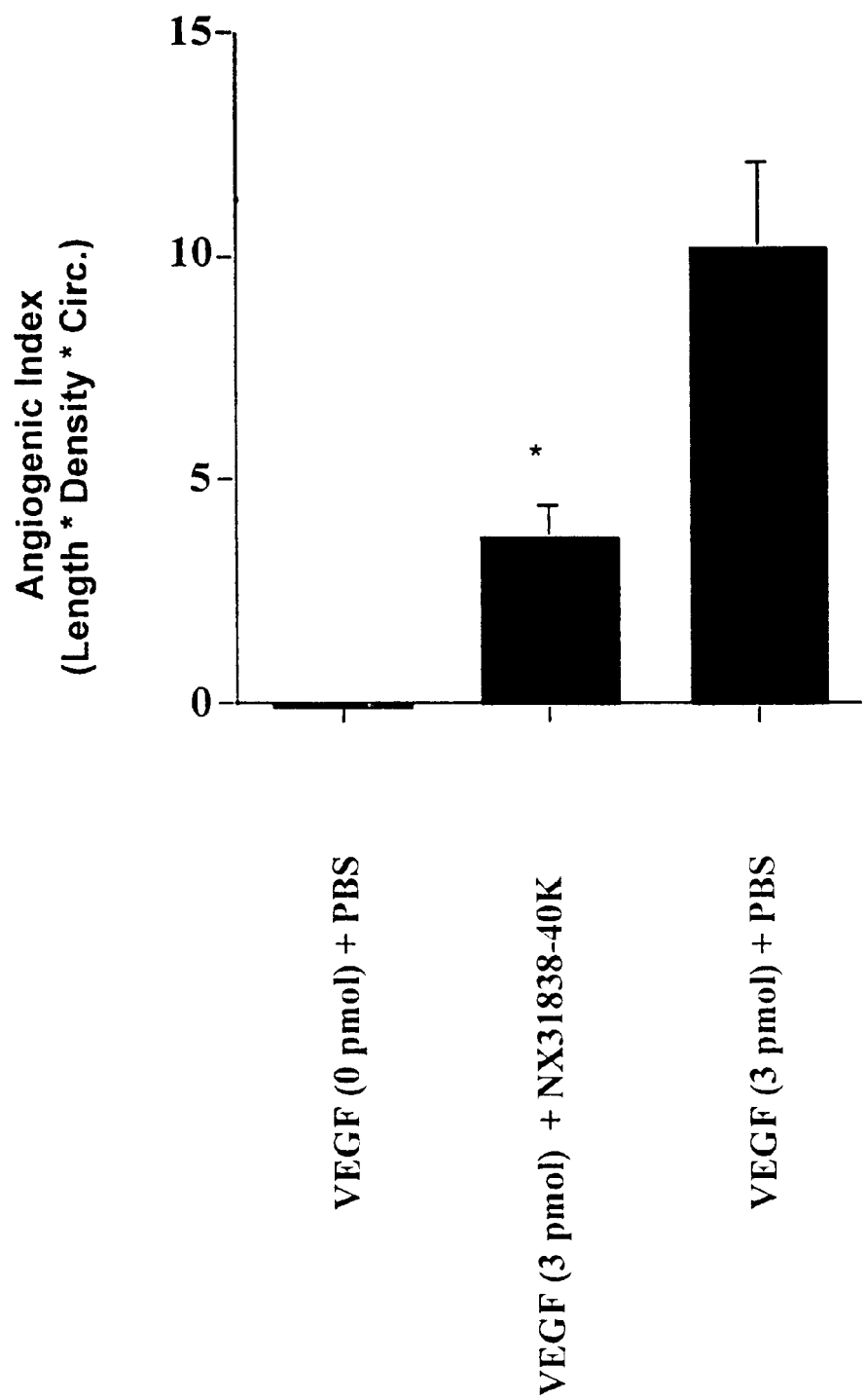
Figure 9C:
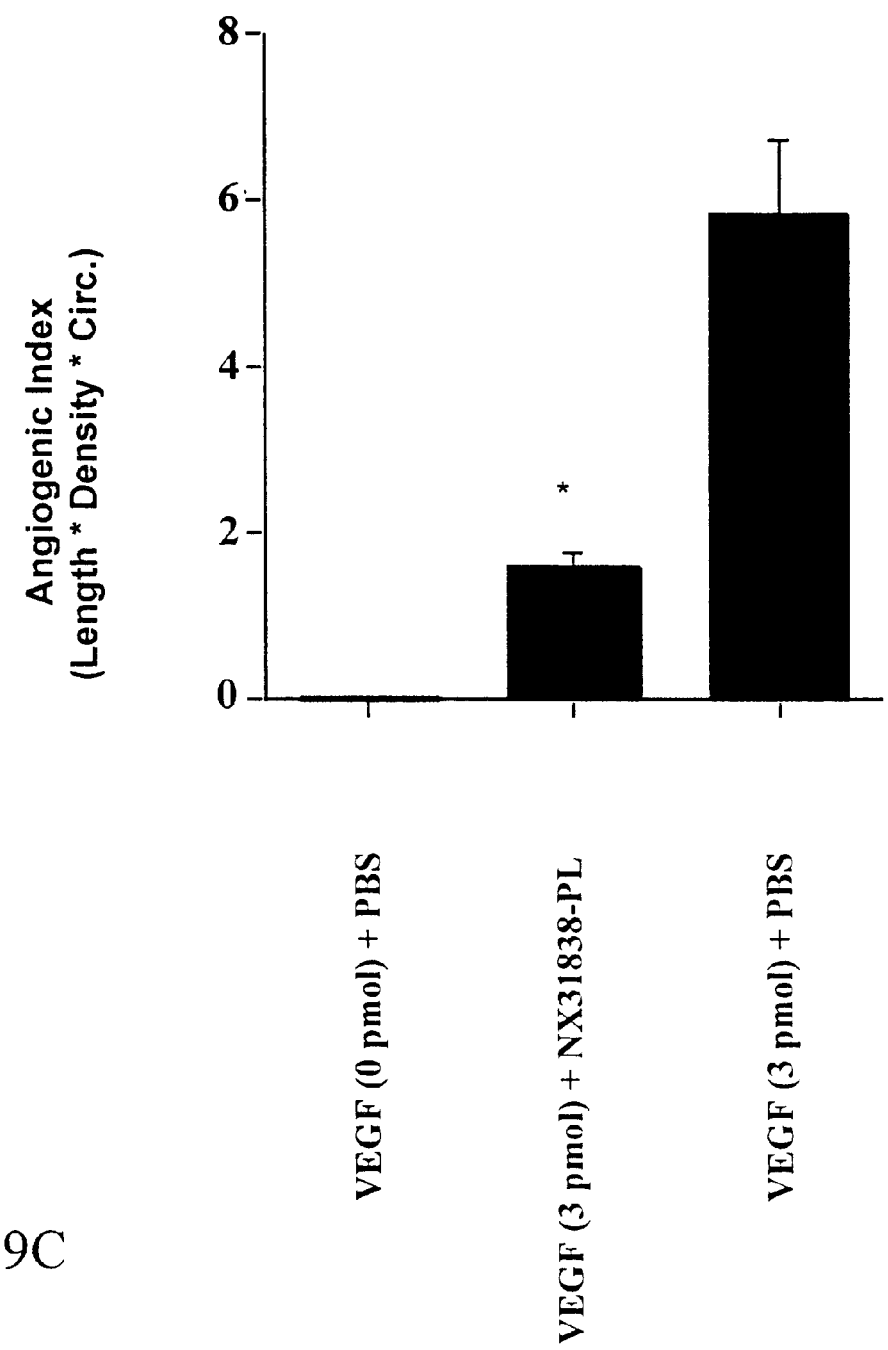
Figure 10:
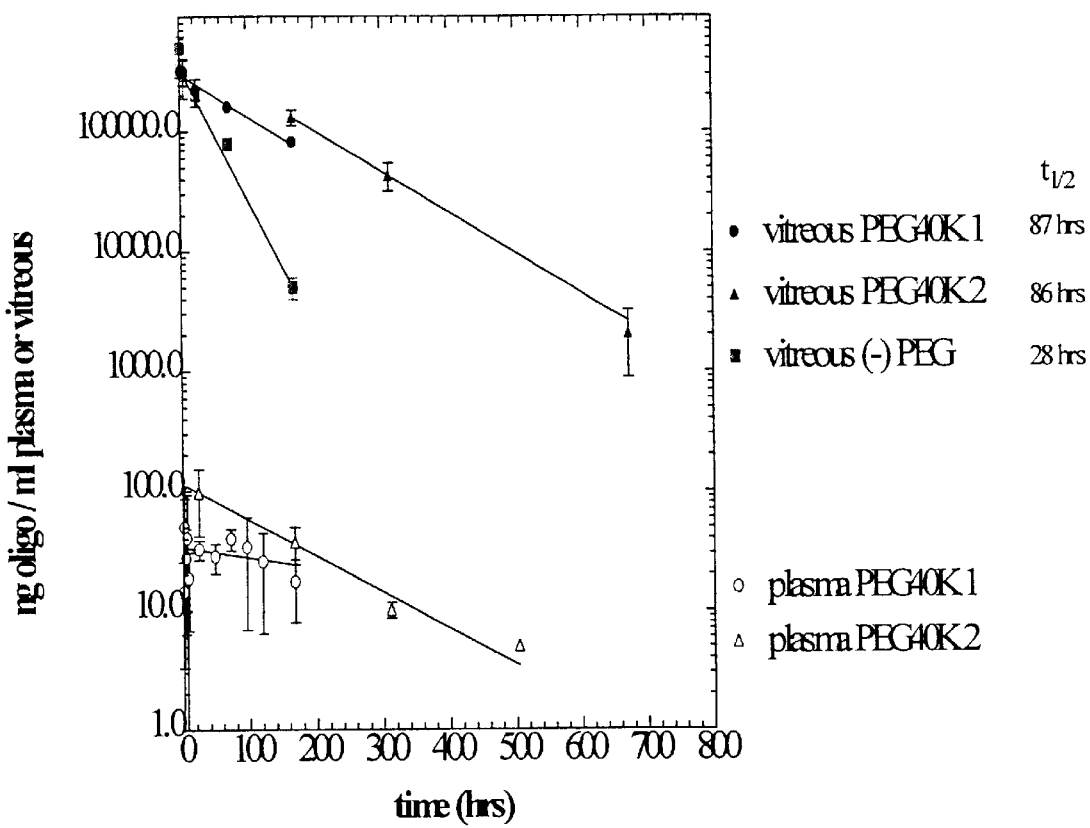
FIG. 10 summarizes the data for the plasma (○,△) or vitreous (●,▲,■) concentration of NX31838-40K PEG as a function of time following administration.

The ability of Nucleic Acid Ligand formulations to block VEGF-induced angiogenesis is seen in FIGS. 9A–C Despite being equally effective as the other formulations in blocking vascular permeability changes, NX3 1838–20K PEG was ineffective at attenuating the angiogenic response in the normally avascular cornea. However, both NX31838–40K PEG and liposomal NX31838-PL significantly reduced the level of angiogenesis by 65–70%. It is presumed that these differences are attributable to the respective pharmacokinetic profiles of the Nucleic Acid Ligands.

Statistical Analysis: Groups in the Miles assay and corneal angiogenesis models were compared using Rank ANOVA with Dunnett's comparisons.

Example 10

In Vivo Efficacy of VEGF Nucleic Acid Ligand in Tumor Models

Human Tumor Xenograft Model

Figure 11:
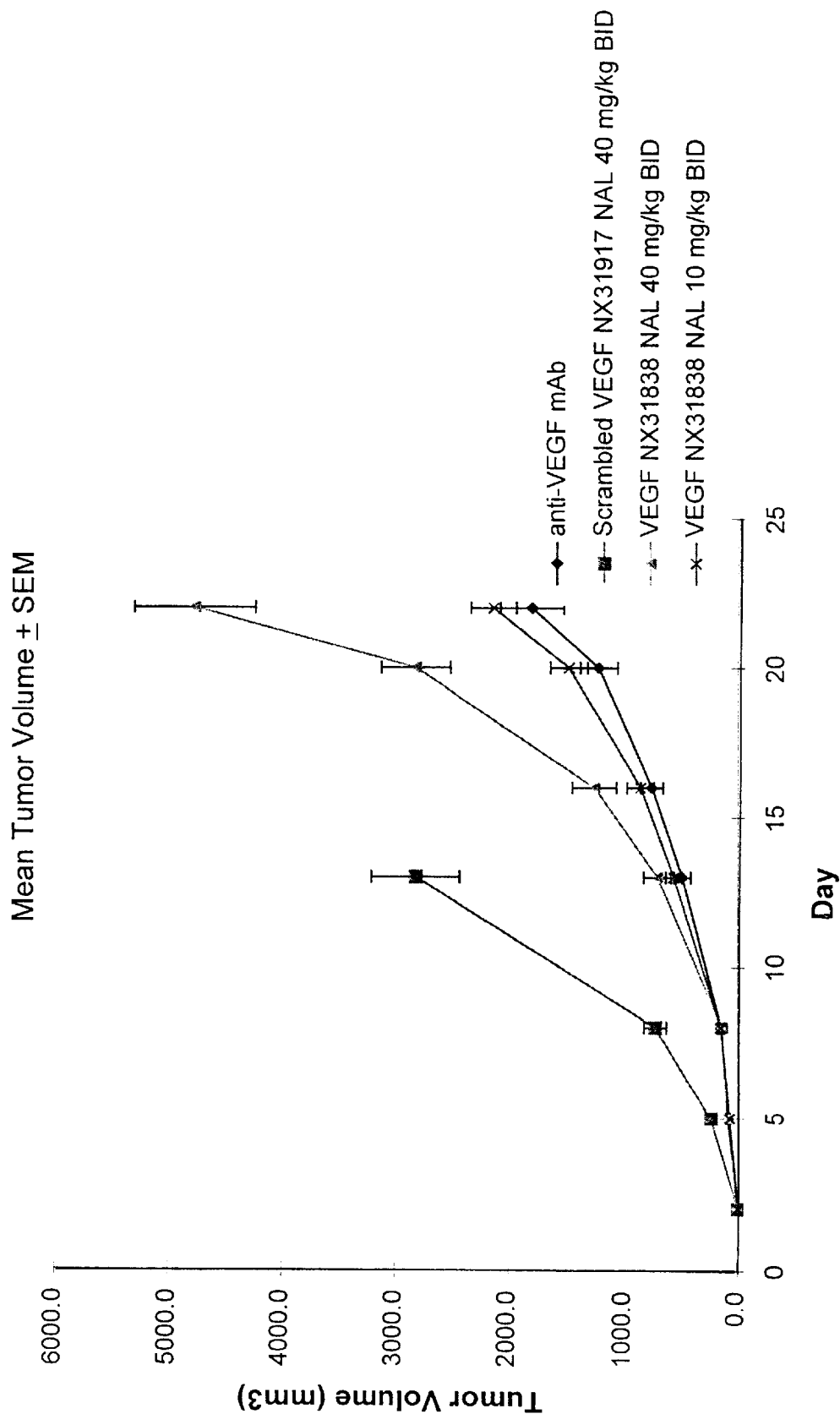
FIG. 11 shows tumor growth curves of human A673 tumors growing subcutaneously (s.c.) in nude mice treated with 40 mg/kg or 10 mg/kg of VEGF NX31838 40K PEG Nucleic Acid Ligand (NX 31838 NAL) delivered twice a day (BID). A negative control consisted of a scrambled VEGF Nucleic Acid Ligand sequence, NX31917 NAL (see FIG. 1R for molecular description), dosed at 40 mg/kg twice daily, and a positive control consisted of an anti-VEGF monoclonal antibody mAb 26503.11 (R&D Systems) dosed at 100 μg/mouse twice weekly. Since there appeared to be no significant difference between the 40 mg/kg dose group and the 10 mg/kg dose group, no further dosing of the 40 mg/kg group occurred after day 14. Groups of 8 mice were implanted s.c. with $1 \times 10^7$ A673 tumor cells on day 0, and treatment with test compounds by intraperitoneal injections initiated on day 1 for the duration of the experiment. Tumor volume, expressed as mm$^3$, was determined using the formula: Tumor vol.=L×W$^2$/2.

The ability of the VEGF Nucleic Acid Ligand NX31838 40K PEG to affect solid tumor growth was determined in a subcutaneous tumor model in nude mice. The A673 human rhabdomyosarcoma tumor cells were grown in tissue culture, harvested and $1\times10^7$ viable cells were implanted subcutaneously, in nude mice, proximal to the axillary region of the flank. Treatment with test compounds was initiated 12 hours later, and continued for the duration of the experiment. Compounds were dosed intraperitoneally, twice daily at 10 and 40mg/kg. A negative control consisted of dosing a scrambled aptamer sequence, NX31917–40K PEG (See FIG. 1R for molecular description) at 40 mg/kg twice daily, and a positive control consisted of anti-VEGF antibody Mab.26503.11 (R & D Systems, Lot # LD03) dosed at 100 μg/ mouse twice weekly. Both Nucleic Acid Ligand-treated groups, and the antibody treated groups demonstrated a significant slowing of tumor growth relative to the scrambled sequence negative control group (FIG. 11). The % Tumor Growth Inhibition (TGI), was determined to be 75% and 80% for the 40mg/kg and 10 mg/kg BID groups and 83% for the monoclonal antibody treated group (Table 8). Since there appeared to be no significant difference between the 40mg/kg dose group and the 10 mg/kg dose group, no further dosing of the 40mg/kg group occurred after day 14. As can be seen in FIG. 11, several days after termination of dosing, tumors grew rapidly and mimicked the growth rate of the negative control group, while the 10 mg/kg Nucleic Acid Ligand group and the antibody treated group continued to grow at a reduced rate.

Figure 12:
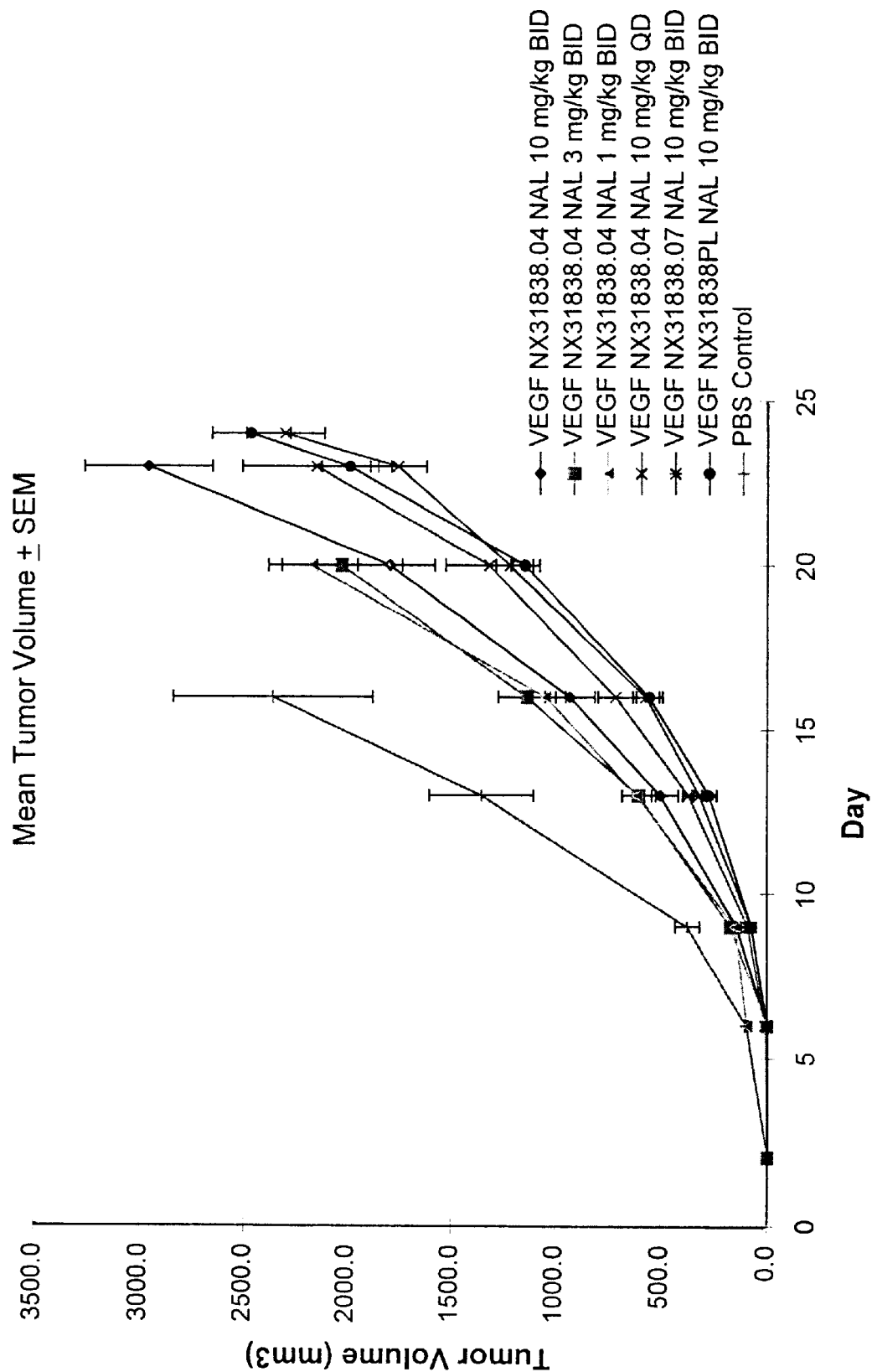
FIG. 12 shows tumor growth curves of different dose schedules (comparison of twice daily dosing (BID) to once daily dosing (QD)), 40K PEG batches (comparison NX31838.07 batch with the new NX31838.04 batch), and different drug formulations (comparison of liposomal VEGF NX31838PL NAL to VEGF NX31838 NAL 40K PEG) of VEGF NX31838 Nucleic Acid Ligand (NAL). Groups of 8 mice were implanted s.c. with $1 \times 10^7$ A673 tumor cells on day 0, and treatment with test compounds by intraperitoneal injections initiated on day 1 for the duration of the experiment. Several groups had animals where the tumors failed to grow, and consequently for final analysis some groups contain only 7 (NX31838.04 10 mg/kg BID, and NX31838.04 3 mg/kg BID), or 6 (NX31838.04 10 mg/kg QD, and NX31838.07 10 mg/kg BID) animals. Tumor volume, expressed as mm$^3$, was determined using the formula: Tumor vol.=L×W$^2$/2.

Additional studies were performed using the same tumor model where new batches of VEGF Nucleic Acid Ligand, NX31838 40K PEG (designated NX31838.04 and NX31838.07) were compared, and also dose titrated downward from 10 mg/kg BID, 3mg/kg BID and 1 mg/kg BID. The experiment also included a once daily dose of 10 mg/kg, as well as a Liposomal form of the VEGF Nucleic Acid Ligand, NX31838 PL at 10 mg/kg BID. As can be seen in FIG. 12 and Table 9, the same degree of tumor growth inhibition was achieved in both experiments. Both batches of VEGF Nucleic Acid Ligand were equivalent when compared on the twice daily dosing schedule, with TGI values of 61% and 70% for the old and new batch, respectively. In addition, it was determined that the once daily dosing (SID) was as effective as the twice daily dosing. However, the titration scheme used in this experiment failed to reach a no effect dose.

Figure 13:
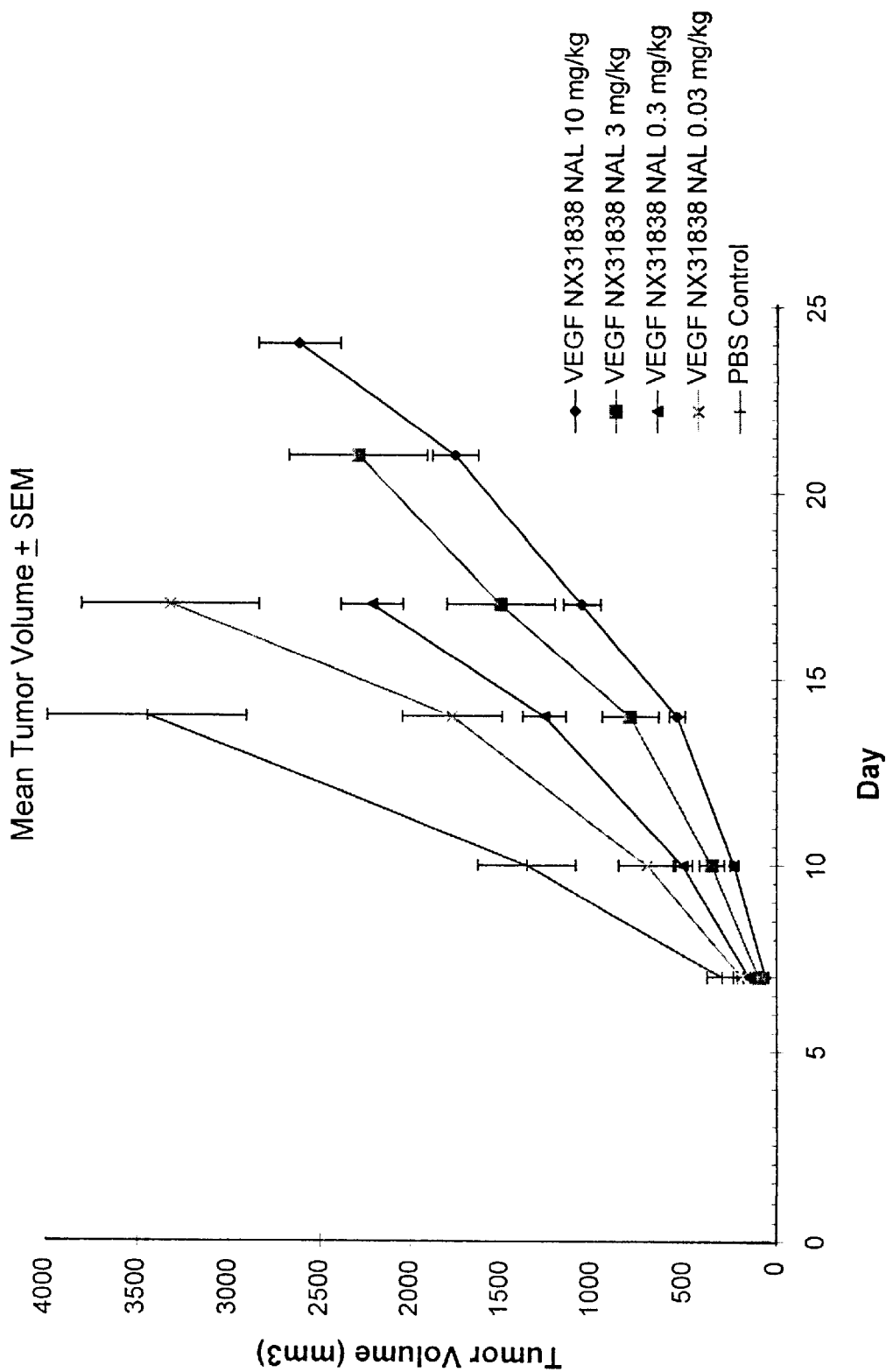
FIG. 13 shows dose-dependent inhibition of A673 tumors growing subcutaneously (s.c.) in nude mice by VEGF NX31838 40K PEG Nucleic Acid Ligand (NX31838 NAL) delivered once daily. This titration failed to reach a no effect dose; tumor inhibition was still observed with the lowest (0.03 mg/kg) dose. Groups of 8 mice were implanted s.c. with $1 \times 10^7$ A673 tumor cells on day 0, and treatment with test compounds by intraperitoneal injections initiated on day 1 for the duration of the experiment; group NX31838 NAL 3 mg/kg had 2 animals where tumors failed to grow and consequently contains only 6 animals. Tumor volume, expressed as mm$^3$, was determined using the formula: Tumor vol.=L×W$^2$/2.

A third experiment was performed where further downward titration of the VEGF Nucleic Acid Ligand was able to demonstrate a dose response relationship relative to tumor growth. In this experiment the VEGF Nucleic Acid Ligand was titrated down, approaching a no effect dose of 0.03 mg/kg. The relative tumor growth inhibition can be seen in FIG. 13 and is summarized in Table 10.

Figure 14:
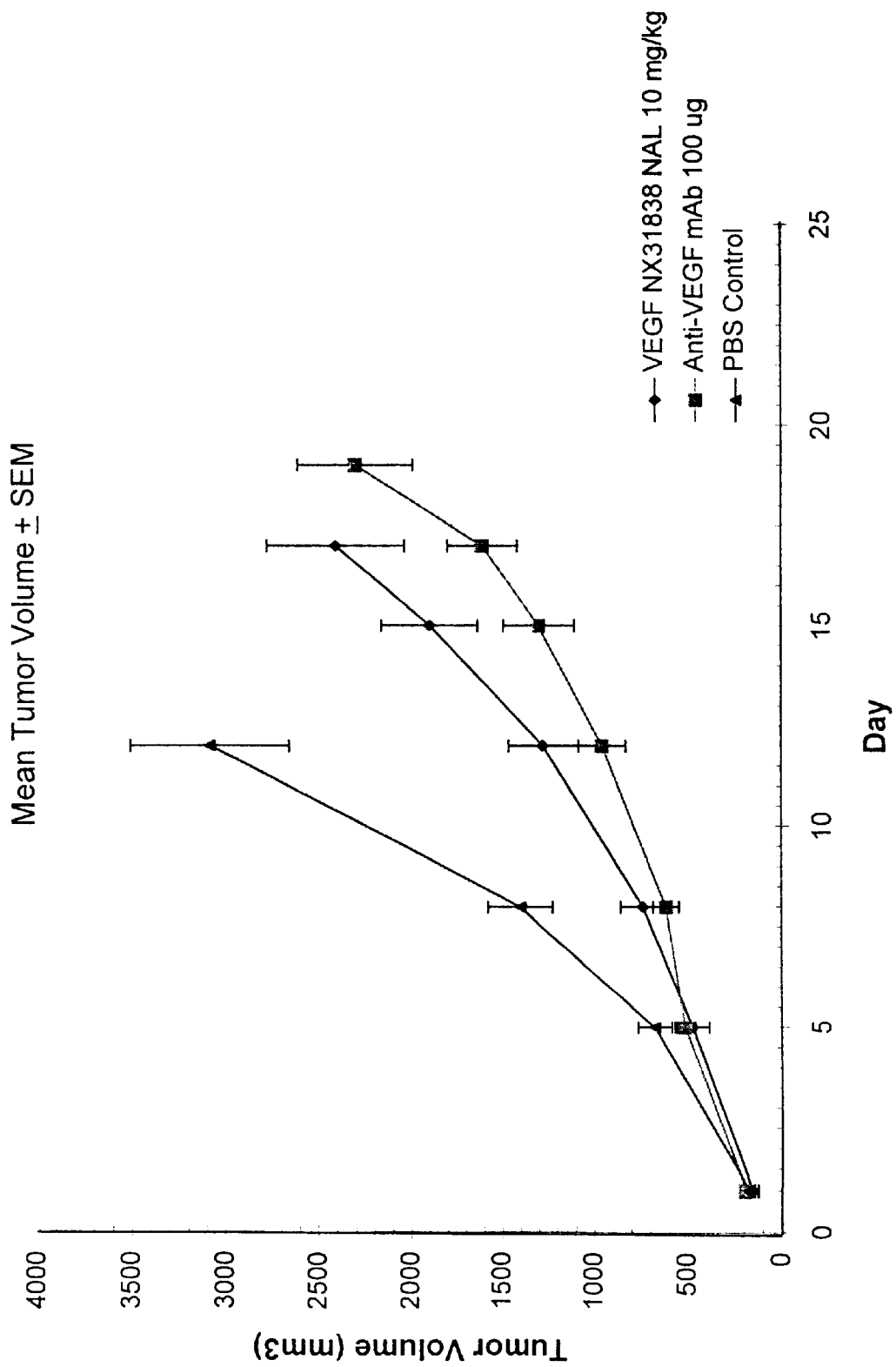
FIG. 14 shows tumor growth curves demonstrating inhibition of staged (i.e., established) A673 tumors growing subcutaneously (s.c.) in nude mice by VEGF NX31838 40K PEG Nucleic Acid Ligand (NAL) delivered once daily. A positive control consisted of an anti-VEGF monoclonal antibody mAb 26503.11 (R&D Systems) dosed at 100 μg/mouse twice weekly. Mice were implanted with $1 \times 10^7$ A673 cells, and tumors allowed to grow to a volume of 200±100 mm$^3$, at which time animals were sorted by weight, tattooed for permanent identification, and treatment with test compounds by intraperitoneal injections initiated and continued for the duration of the experiment. Each point represents the mean of 8 mice. Tumor volume, expressed as mm$^3$, was determined using the formula: Tumor vol.=L×W$^2$/2.

In addition to the three unstaged tumor studies, a staged tumor study was prepared where the tumors were allowed to establish and reach 200+/–100 $mm^3$ prior to initiation of treatment with the VEGF Nucleic Acid Ligand. The dose groups of 10 mg/kg of NX31838 40K PEG and the 100 μg twice weekly of mAb 26503 (R & D Systems) achieved 59% and 69% tumor growth inhibition respectively (FIG. 14, Table 11). These collective studies demonstrate that the VEGF Nucleic Acid Ligand is able to slow the A673 tumor from establishing as well as inhibiting tumor growth once tumors have established.

Kaposi's Sarcoma Model

Figure 16:
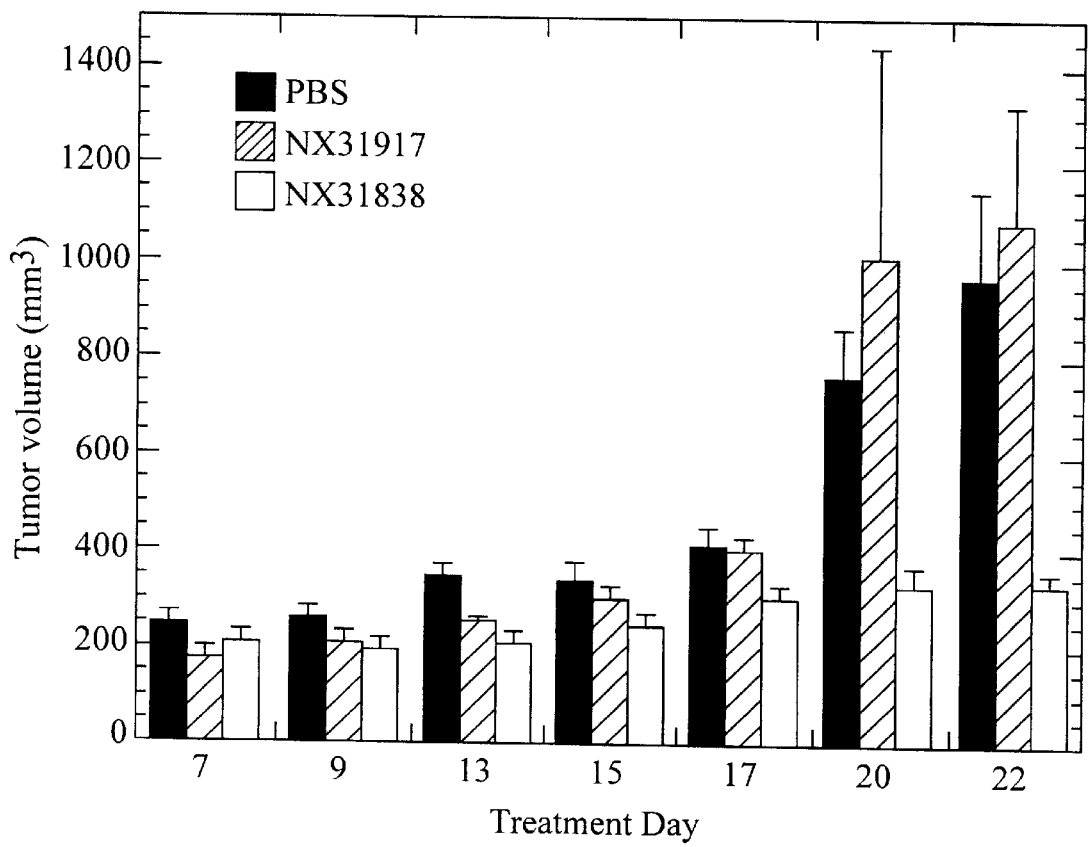
FIG. 16 shows the growth curves of KSY-1 tumors implanted subcutaneously in nude mice. The mice were treated by intraperitoneal injections of NX31917 40K PEG or is NX31838 40K PEG (30 mg/kg) or PBS twice daily for the duration of the experiment. Treatment was initiated one day after subcutaneous implantation of $2 \times 10^7$ KSY-1 cells in the hind flank of nude mice. Four mice were used in each group. Errors are SEM.

The effect of NX 31838–40K PEG on the subcutaneous growth of Kaposi's Sarcoma cell line KSY-1 in nude mice was also examined. KSY-1 cells are unique among tumor cell lines in that they can be inhibited in culture by VEGF antagonists. KSY-1 cells were grown in culture, pooled and injected subcutaneously ($2\times10^7$ cells/mouse) in the hind flank of mice. Three groups of mice (4 mice per group) were treated by intraperitoneal injections every 12 hours with either 30 mg/kg of NX31838–40 K PEG, 30 mg/kg NX31917–40 K PEG (see FIG. 1R for molecular description) or PBS for the duration of the experiment. Treatment was initiated one day after tumor cell implantation. While tumor growth in the PBS-treated and NX31917–40 K PEG-treated groups was comparable, considerable inhibition of tumor growth was observed in the NX31838–40K PEG-treated group (FIG. 16). NX31838–40K PEG inhibited the growth of KSY-1 tumors by 65% (compared with the PBS-treated group) or by 69% (compared with the NX31917-40 K PEG-treated group) at the time the experiment was terminated (day 22).

Example 11

Figure 1H:
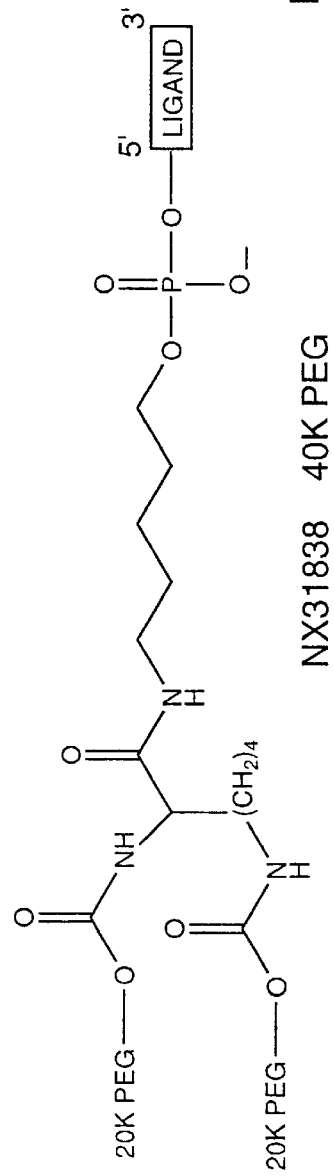
Figure 1I:
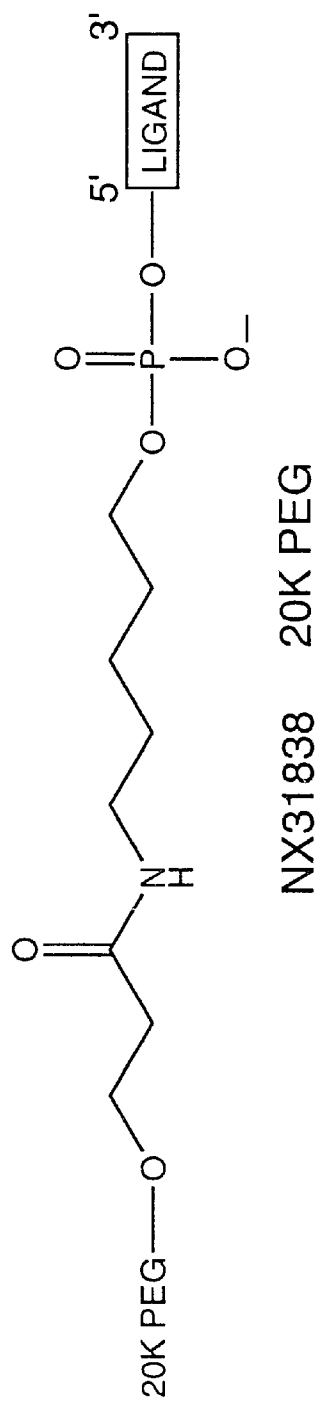
Figure 1K:
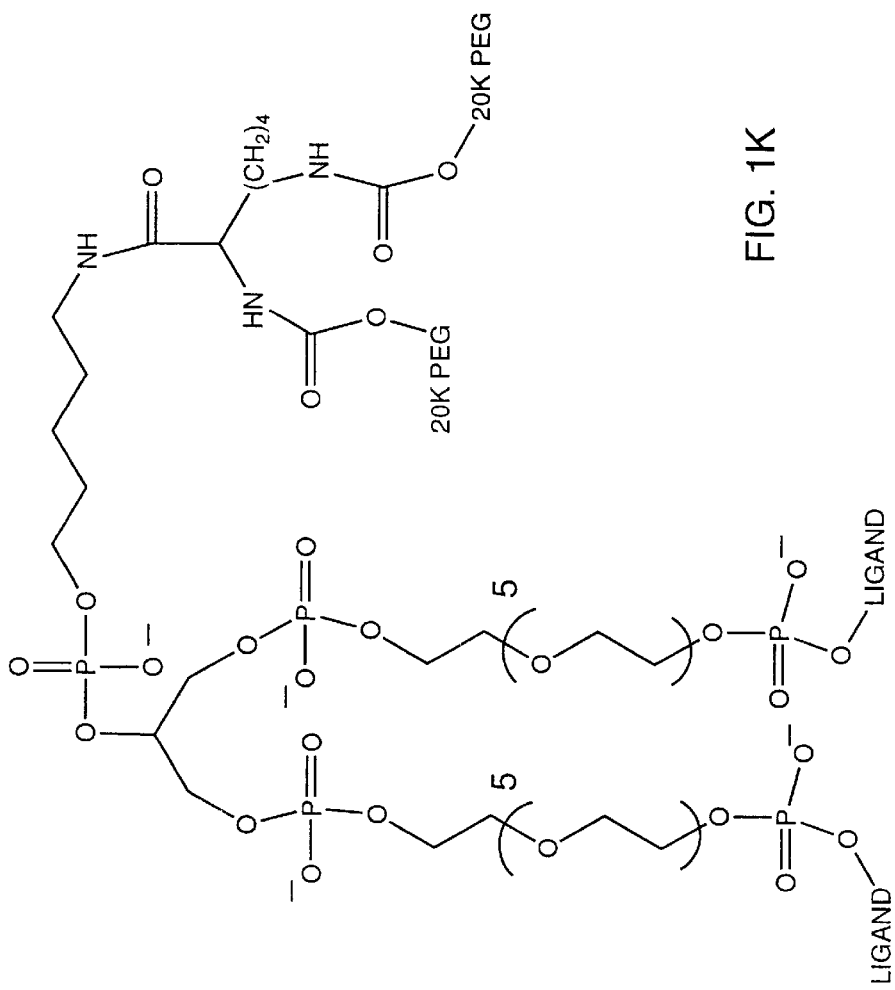
Figure 1M:
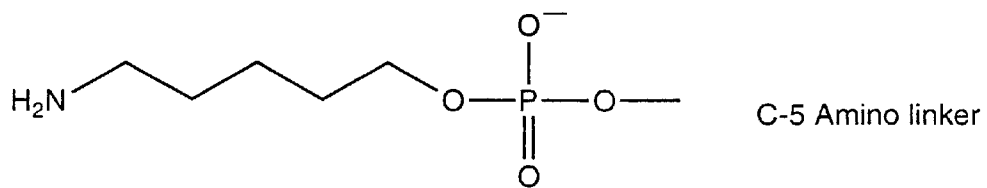
Figure 1N:
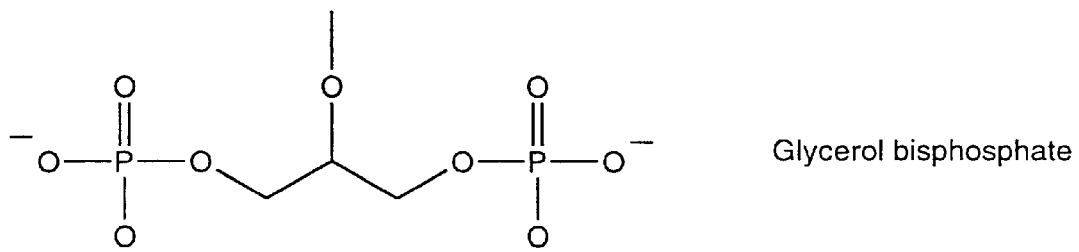
Figure 1O:
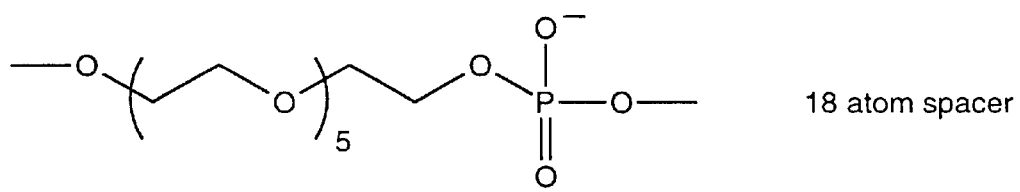
Figure 1P:
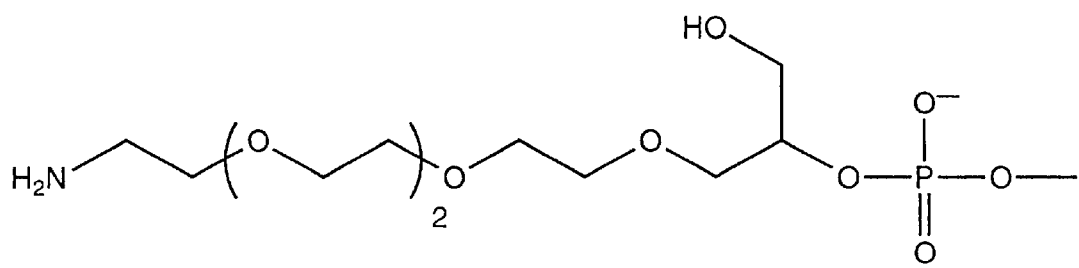
Figure 1Q:
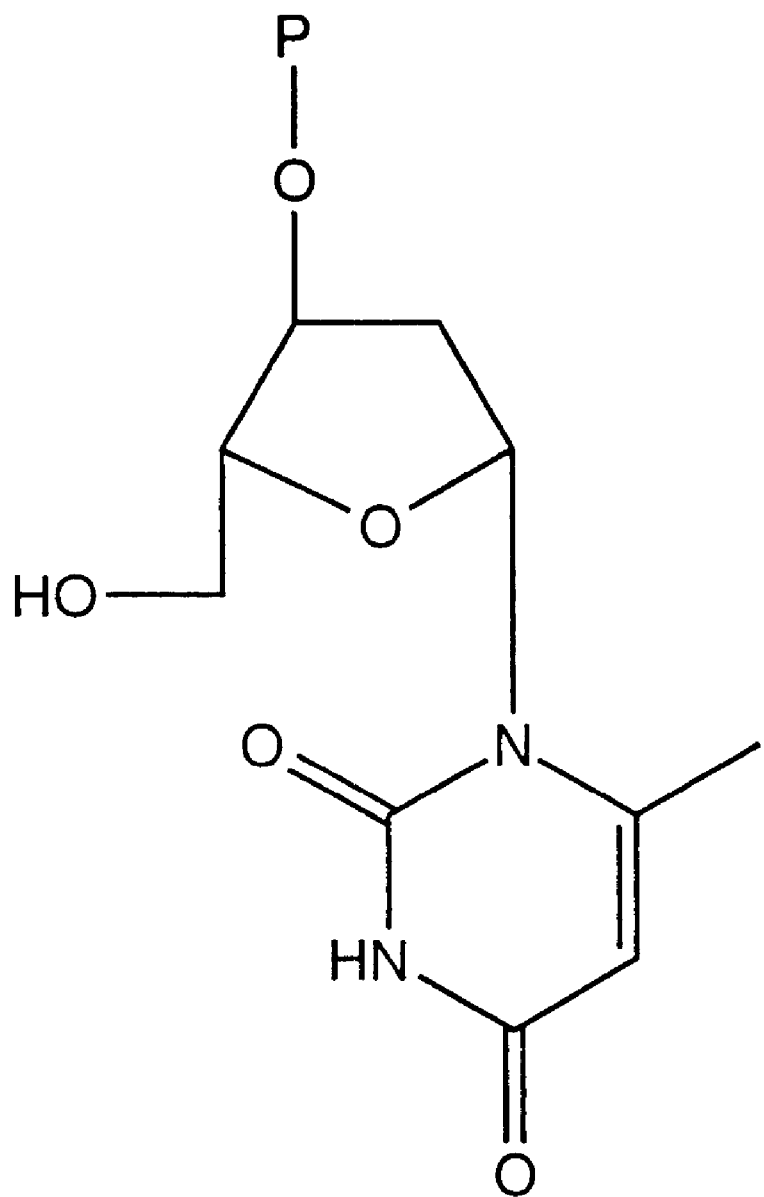
Figure 1R:
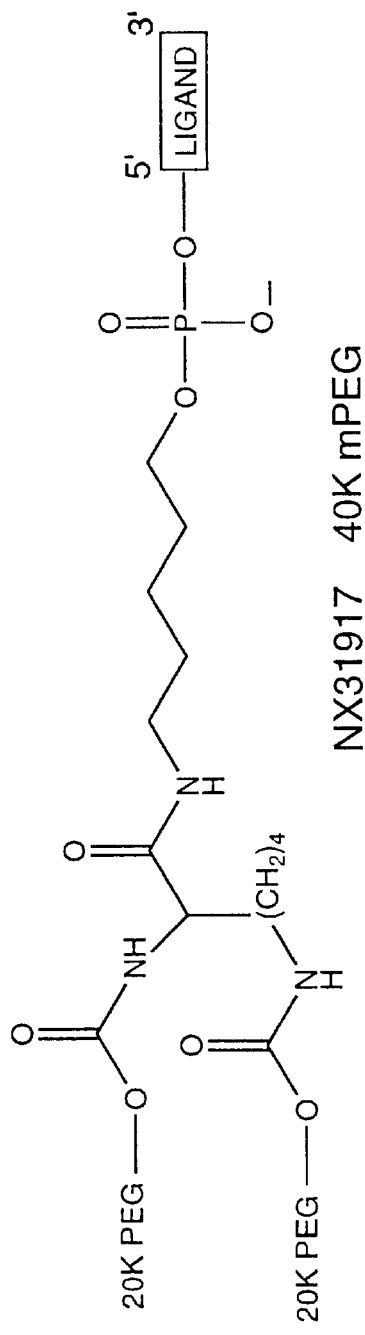

Intravitreal Pharmacokinetics of VEGF Nucleic Acid Ligand NX31838+40KPEG in Rabbits New Zealand White rabbits were treated with VEGF Nucleic Acid Ligand NX31838 conjugated to 40 mPEG by intravitreal administration at a dose of 0.5 mg/eye. 40K PEG was conjugated to the VEGF Nucleic Acid Ligand as described in Example 5, and the resulting complex is as shown in FIG. 1H (SEQ ID NO:8). Rabbits received intravitreal injection of NX31838–40K PEG in each eye. The time between doses for a given animal did not exceed 15 minutes. Blood and vitreous samples were collected as specified in Table 7.

Analysis of plasma and vitreous samples were carried out by the use of a double hybridization assay. In this assay, two hybridization probes are used, a capture probe attached to wells of 96 well plates, and a biotinylated detect probe. The capture probe forms a hybrid with the 5' end of the Nucleic Acid Ligand. This assay is highly specific and sensitive to full length Nucleic Acid Ligand to yield a positive signal. The current limit of quantitation is approximately 2 fmoles in 5 $\mu$l of plasma.

TABLE 1

Summary of VEGF Nucleic Acid Ligand pharmacokinetic parameters after i. v. bolus administration in Sprague Dawley rats determined from the data shown in FIG. 15 (compartmental analysis).

| Parameter | NX213 | NX278 | NX278-L |
|---|---|---|---|
| Total AUC ($\mu$g * min/ml) | 147 | 202 | 531 |
| C, t = 0 min ($\mu$g/ml) | 14.59 | 23.16 | 16.95 |
| C, t = 2 min ($\mu$g/ml) | 15.31 | 14.08 | 15.74 |
| $\alpha t_{1/2}$ (min) | 7 | 3 | 13 |
| $\beta t_{1/2}$ (min) | 49 | 67 | 113 |
| Clearance (ml/kg/min) | 6.80 | 4.95 | 1.88 |
| $V_{ss}$ (ml/kg) | 72 | 251 | 152 |

TABLE 2

2'-F-pyrimidine ligands to VEGF$_{165}$

| Ligand (frequency) | Sequence of variable region 5'-gggaggacgaugcgg [variable region] cagacgacucgcccga-3' | | $K_d$ (pM) | SEQ. ID NO: 14 & 139 |
|---|---|---|---|---|
| Family 1 | | | | |
| VP30.7 | gcggg | gAAGAAUUGG UCAUCGUCGUCUCCGCCUCCC | 3000 | 15 |
| VP30.12 | gcggAAUACG | GAAGAAUUGG AUACAUAUGCUCGU | 7 | 16 |
| VP30.13 (7) | ugcggGAUAACA | GAAGAAUUGG UGAACAACGUGGU | 10 | 17 |
| VP30.16 | AUGAUCGCGUAG | GAAGUAUUGG AAGGCCCU | 6 | 18 |
| VP30.19 | gcggCACUUUA | GAAGAAUUGA AUUUCCCGCUGGU | 9 | 19 |
| VP30.22 (6) | gcggUAG | GAAGAAUUGG AAGCGCAUUUUCCUCGY | 20 | 20 |
| VP30.25 | cggCGGGAUUUUG | GAAGAAUUGG AUAUUGGCCU | 20 | 21 |
| VP30.26 (2) | gcggCGGYACUUUG | GAAGAAUUGA AUUUCCCGCU | 10 | 22 |
| VP30.27 | gcggg | gAAGAAUUGG AUAUAUCGUUCACCCCCACCU | 400 | 23 |
| VP30.40 | ugcgAAACG | GAAGAAUUGG AUACGCAAGCACGUU | 6 | 24 |
| VP30.41 | gcggUAG | GAAGUAUUGU AAGCGCCUCGUUUUCGC | 7 | 25 |
| VP30.51 (2) | gcggAGUUUUG | GAAGAAUUGG AUGUUCCGAUCGU | 90 | 26 |
| VP30.54 | gcggAAGAAACG | GAAGAAUUGG AGACACGCUCGU | 10 | 27 |
| VP40.4 (5) | gggaggacgaugcgg | GAAGAAUUGA UGUUGUAUUGUCCUUCCGAUUUCCUGCCGU | 200 | 28 |
| VP40.43 | ggaggacgaugcggACA | GAAGAAUUGG GCUUCGCAUUAUCCUCUGUCAGCCGC | 30 | 29 |
| VP40.53 | ugcggUGAGAGAAACG | GAAGAAUUGG AUACGAUACUCAUCGCGCU | 8 | 30 |
| VT30.4 | augcggCUUAAGUUUUG | GAAGAAUUGA AUACUGGGU | 20 | 31 |
| VT30.7 | gcggUAACCAGUG | GAAGAAUUGG CUGCUAUCCU | 10 | 32 |
| VT30.10 | augcggAACG | GAAGAAUUGG AUACGUAGCAUGCGU | 2 | 33 |
| VT30.13 | ugcggCAGGAUUUUG | GAAGAAUUGG AUAUUGGCCGca | 10 | 34 |
| VT30.20 | gaugcggAAACG | GAAGAAUUGG AUACCGCUACGUGUU | 4 | 35 |

TABLE 2-continued

2'-F-pyrimidine ligands to VEGF$_{165}$

| Ligand (frequency) | Sequence of variable region 5'-gggaggacgaugcgg [variable region] cagacgacucgcccga-3' | | $K_d$ (pM) | SEQ. ID NO: 14 & 139 |
|---|---|---|---|---|
| VT30.52 | ugcggg | gAAGAAUUGA GCAUUCCUUCUCCUUGUGCCU | 9000 | 36 |
| VT30.53 | gaugcggAGCUAACG | GAAGAAUUGG AAACAACCGCGUc | 10 | 37 |
| Family 2 | | | | |
| VP30.2 (5) | ggYGA | ACCGA UGGAA UUU UUGGACGC UCGCCU | 10 | 38 |
| VP30.5 (4) | gAYCA | ACCGA UUGAC GUUA UGGGACGC UGGUc | 8 | 39 |
| VP30.31 (5) | gcggUA | ACCGA UUGAA CUUC UUGGACGC UACCGU | 6 | 40 |
| VP30.43 | ggUA | ACCGAA UUGAA GUUA UUGGACGC UACCU | 5 | 41 |
| VP40.9 | gGAGCAGA | ACCGA UAGAA GAA UUGGACGC UCAGCUCCGGGU | 30 | 42 |
| VP40.14 | GUACCAGAAUGAGCA | ACCGA AUGAA GAA CUGGACGC UGCUca | 8 | 43 |
| VP40.17 | ugcggUGA | ACCGA UGGAA UCGC UUGGACGC UCAUCGCACGUUGCU | 10 | 44 |
| VT30.9 (6) | ggUCA | ACCGG UUGAA UAU UUGGUCGC UGACCU | 30 | 45 |
| Family 3 | | | | |
| VT30.1 (2) | gacgaugcgg | A ACUA GUGAAUGCUU AUA CGA CCGUUUGUc | 10 | 46 |
| VT30.2 | gcgg | AUCA GUGAAUGCUU AUA GA CCGCCUCCGU | 2 | 47 |
| VT30.3 (7) | gaugcgg | AGA AUCA GUGAAUGCUU AUA AAUC UCGYGUc | 5 | 48 |
| VT30.11 | gaugcgg | A AUCA GUGAAUGCUU AUA GCUC CCGCGUCCU | 4 | 49 |
| VT30.15 | gcgg | A ACCA GUGAAUGCUU AUA AGA CUGCUCGU | 3 | 50 |
| VT30.21 | cgaugcgg | AUCA GUGAAUGCUU AUA GA CCGUAUUGCGU | 6 | 51 |
| VT30.28 | gaugcgg | AGA AUCA GUGAAUGCUU AUA AACC UCGUGUc | 60 | 52 |
| VT30.29 | augcggA | AUCA GUGAAUGCUU AUA GC UCCGCGUGGU | 10 | 53 |
| VT30.35 | cgg | ACCA GUGAAUGCUU AUA AGCCCA UCGACCU | N.D. | 54 |
| VT30.41 | gaugcgg | CAGG GUGAAUGCCA AUG UACUUU UCGCGUc | 40 | 55 |
| VT30.42 | gacgaugcggA | AUCA GUGAAUGCUU AUA GC UCCACGUCGUc | N.D. | 56 |
| VT30.44 | gcggA | AUCA GUGAAUGCUU AUA CA UCCGCUCGGU | 10 | 57 |
| VT30.54 | gcggG | ACUAG GUGAAUGCCA AUA UUCUUC UCCGU | 10 | 58 |

TABLE 3

| Ligand | Sequence | Length (nts) | $K_D$ (pM) | SEQ ID NO: |
|---|---|---|---|---|
| t22 | GACGAUGCGGUAGGAAGAAUUGGAAGCGC* | 29 | 70 | 59 |
| t22a | GACGAUGCGGUAGGAAGAAUUGGAAGCG | 28 | 3000 | 60 |
| t22b | ACGAUGCGGUAGGAAGAAUUGGAAGCGC | 28 | 80 | 61 |
| t22c | GCGGUAGGAAGAAUUGGAAGCGC | 23 | 90 | 62 |
| t22d | CGGUAGGAAGAAUUGGAAGCGC | 22 | 100 | 63 |
| t22e | GGUAGGAAGAAUUGGAAGCGC* | 21 | 200 | 64 |
| t22f | GUAGGAAGAAUUGGAAGCGC* | 20 | >100,000 | 65 |
| t2 | GGCGAACCGAUGGAAUUUUUGGACGCUCGCC* | 31 | 20 | 66 |
| t2a | GCGAACCGAUGGAAUUUUUGGACGCUCGC | 29 | 40 | 67 |
| t2b | CGAACCGAUGGAAUUUUUGGACGCUCG | 27 | 100 | 68 |
| t2c | GAACCGAUGGAAUUUUUGGACGCUC* | 25 | 200 | 69 |
| t2d | AACCGAUGGAAUUUUUGGACGCU* | 23 | 20,000 | 70 |
| t2e | ACCGAUGGAAUUUUUGGACGC* | 21 | >100,000 | 71 |

TABLE 3-continued

| Ligand | Sequence | Length (nts) | $K_D$ (pM) | SEQ ID NO: |
|---|---|---|---|---|
| t44 | GCGGAAUCAGUGAAUGCUUAUACAUCCGC* | 29 | 10 | 72 |
| t44a | CGGAAUCAGUGAAUGCUUAUACAUCCG | 27 | 10 | 73 |
| t44b | GGAAUCAGUGAAUGCUUAUACAUC<u>C</u> | 25 | 60 | 74 |
| t44c | GAAUCAGUGAAUGCUUAUACAUC* | 23 | 2000 | 75 |
| t44d | AAUCAGUGAAUGCUUAUACAU* | 21 | >100,000 | 76 |
| t44e | AUCAGUGAAUGCUUAUACA* | 19 | >100,000 | 77 |

TABLE 4

Effect of 2'-OMe-purine substitutions on affinity for VEGF.

| Ligand | Sequence | $K_D$ (pM) | SEQ ID NO: |
|---|---|---|---|
| t22OMe (OH-10,12,22) | GACGAUGCGGUAGGAAGAAUUGGAAGCGC | 10 | 78 |
| t22OMe (OH-10,12) | GACGAUGCGGUAGGAAGAAUUGGAAGCGC | 20 | 79 |
| t22OMe (OH-10,22) | GACGAUGCGGUAGGAAGAAUUGGAAGCGC | 4,000 | 80 |
| t22OMe (OH-12,22) | GACGAUGCGGUAGGAAGAAUUGGAAGCGC | 90 | 81 |
| t2OMe (OH-6,21) | GGCGAACCGAUGGAAUUUUUGGACGCUCGCC | 60 | 82 |
| t2OMe (OH-6) | GGCGAACCGAUGGAAUUUUUGGACGCUCGCC | 500 | 83 |
| t2OMe (OH-21) | GGCGAACCGAUGGAAUUUUUGGACGCUCGCC | 20,000 | 84 |
| t44OMe (OH-5,6) | GCGGAAUCAGUGAAUGCUUAUACAUCCGC | 40 | 85 |
| t44OMe (OH-5) | GCGGAAUCAGUGAAUGCUUAUACAUCCGC | >100,000 | 86 |
| t44OMe (OH-6) | GCGGAAUCAGUGAAUGCUUAUACAUCCGC | >100,000 | 87 |

TABLE 5

| Ligand | Sequence | $K_D$(S.d.) (pM) | $k_d$(s.d.) (sec$^{-1}$) | $k_a$ (M$^{-1}$sec$^{-1}$) | SEQ ID NO: |
|---|---|---|---|---|---|
| t22OMe | GCGGUAGGAAGAAUUGGAAGCGC | 67 (36) | 0.012 (0.004) | $1.8 \times 10^8$ | 88 |
| t2OMe | GCGAACCGAUGGAAUUUUGGACGCUCGC | 140 (50) | 0.0042 (0.002) | $3.0 \times 10^7$ | 89 |
| t44OMe | CGGAAUCAGUGAAUGCUUAUACAUCCG | 51 (11) | 0.0074 (0.002) | $1.5 \times 10^8$ | 90 |

TABLE 6

Additional 2'-F-pyrimidine ligands to VEGF$_{165}$.

| Ligand (frequency) | Sequence of variable region 5'-gggaggacgaugcgg [variable region] cagacgacucgcccga-3' | Kd (Pm) | SEQ. ID NO: 14 and 139 |
|---|---|---|---|
| VP30.1 | UCUUUGAGUUUUUGCCAACGGUUUUCGCU | 32,000 | 91 |
| VP30.6 | AACGGAAUUCUUGGAUACACACCUCGUCCU | 20 | 92 |
| VP30.11 | UCAGGAACGGAAUUUUUGGAGACACGCCCU | 25 | 93 |
| VP30.14 | ACUGGGAGAAUCCGAAAAACCUUCACGCGU | 25 | 94 |
| VP30.18 | AUCCAUCAUUUAACCGUUUGCUCUCCCCCU | 27 | 95 |
| VP30.20 (3) | UUGAUCGGACGUUAGUCAUUUCCCGAUCGU | 57 | 96 |
| VP30.23 | GAGCUUGAAGUUUCAGUAUUGGCACAACCU | 63 | 97 |
| VP30.29 | CGCCACUUUGGAAGUUAUUGAAUUUCGCGU | 7 | 98 |
| VP30.35 | UGAAUGAGCUGACGACCCUGAAUUGCUCGU | 6 | 99 |
| VP30.48 | GAGCUUGAAGUUUCGGUAUUGGCACAACCU | >10,000 | 100 |
| VP30.58 | CAACUAUUCGUUGAUGUUUCCGUGAGCCGU | 6 | 101 |
| VP30.61 | GAGCUUGAAGUUUCAGUACUGGCACAACCU | 43 | 102 |
| VP30.63 | AACCAAUAGAGAUCUUCGGCUGCCCCGCGU | 16 | 103 |

TABLE 6-continued

Additional 2'-F-pyrimidine ligands to VEGF$_{165}$.

| Ligand (frequency) | Sequence of variable region 5'-gggaggacgaugcgg [variable region] cagacgacucgcccga-3' | Kd (Pm) | SEQ. ID NO: 14 and 139 |
|---|---|---|---|
| VP30.65 | AAAACGCUUUUCUUGGCCCCCUCGUUGCGC | 33 | 104 |
| VP30.67 | UUAACGGAAUUCUUGGAUACAUAGCAUGGU | 24 | 105 |
| VP40.1 | CAAAGUUUGAGUUGAUCUGAUACGUUUCAGUAUUGGCGU | N.D. | 106 |
| VP40.2 (5) | AUCUGUGAACUGGGUUUUUGCCGACGGUUACGCUUUUGCU | 35 | 107 |
| VP40.3 (5) | CAAAAGUUUGAGUUGAUCUGAUACGUUUCAGUAUUGGCGU | 2,000 | 108 |
| VP40.5 | UUGAUCGAGGUUCUAAAGCCUAUUUCCUGACUUUCUCCCC | 19 | 109 |
| VP40.10 | AUCUGUGAACUGGGUUUUUGCCGACGGUUACGCUUUUGCU | N.D. | 110 |
| VP40.11 (6) | AAGGAAGAUGUUGAUCGUUUGACGUGAUGUGGAUCCGCGU | 980 | 111 |
| VP40.18 | UAGUAAGUUAUUGAAAGCGCAUCUCUAUCAACUCUCGGCC | 12 | 112 |
| VP40.20 | UACUUUCUUCUUUCUUUGCCUUUCUUUUUCUUUUACGCCU | N.D. | 113 |
| VP40.21 | CAGUUAAUUAAUUUGAGUUGUGAUGUGUGUCGUUAUGGGU | >100,000 | 114 |
| VP40.24 | GAUGCUGAGUGAGGAAGUCUGAUUGUUGCAGUAUUGGCGU | 5,000 | 115 |
| VP40.25 | AAUGGAAUUUGAGUCGAUCUAGAAUGCGUCGUAUGGGCU | 740 | 116 |
| VP40.26 | ACUCAACUGGACGCUAUGUUGACGGUUAUCGCUUUUGGGU | 13 | 117 |
| VP40.36 | CAGGUUCAGAAUUGGCAGUCGCAUUGAUCUUUUUCACCGC | 1,300 | 118 |
| VP40.37 | CAAAAGUUUGAGUUGAUCUGAUACGUUUCCAGUAUUGGCGU | N.D. | 119 |
| VP40.39 | CAGUUAAUUAACUUGAGUUGUGAUGUGUGUCGUUAUGGGU | 73,000 | 120 |
| VP40.41 | CAAAUUCAAGGUCGAGUUAUGCGUAGAUGUGGCUCCUGUG | 11,000 | 121 |

TABLE 8

Anti-Tumor Efficacy of VEGF Nucleic Acid Ligand (NX31838) in the A673 Nude Mouse Xenograph Model % Tumor Growth Inhibition (TGI)

| Treatment | Mean Tumor Volume | Day | % TGI |
|---|---|---|---|
| Scrambled Nucleic Acid Ligand 40 mg/kg BID | 2823 | 13 | 0 |
| VEGF Nucleic Acid Ligand 40 mg/kg BID | 710 | 13 | 74.8 |
| VEGF Nucleic Acid Ligand 10 mg/kg BID | 565 | 13 | 80.0 |
| Anti-VEGF mAb 2× weekly | 489 | 13 | 82.7 |

% TGI = 100 (1 − $W_t/W_c$);
$W_t$ is the mean tumor volume of the treated group at time x;
$W_c$ is the mean tumor volume of the control group at time x
42% TGI or greater is significant

| Tumor Growth Delay | Day to 1000 mm³ | GD ($t_t − t_c$) | Day to 1500 mm³ | GD |
|---|---|---|---|---|
| Scrambled Nucleic Acid Ligand 40 mg/kg BID | 8.5 | 0 | 10 | 0 |
| VEGF Nucleic Acid Ligand 40 mg/kg BID | 14.5 | 6** | — | — |
| VEGF Nucleic Acid Ligand 10 mg/kg BID | 17 | 8.5 | 20 | 10 |
| Anti-VEGF mAb 2× weekly | 18 | 9.5 | 21 | 11 |

**note:
dosing for VEGF Nucleic Acid Ligand @ 40 mg/kg was terminated on day 14

TABLE 9

Anti-Tumor Efficacy of VEGF Nucleic Acid Ligand (NX31838) in the A673 Nude Mouse Xenograph Model % Tumor Growth Inhibition (TGI)

| Treatment | Mean Tumor Volume mean (± SD) | # Animals | Day | % TGI |
|---|---|---|---|---|
| PBS control | 2357 (± 1361) | 8 | 16 | 0 |
| VEGF NX31838.04 10 mg/kg BID | 930 (± 312) | 7 | 16 | 61 |
| VEGF NX31838.04 3 mg/kg BID | 1135 (± 364) | 7 | 16 | 52 |
| VEGF NX31838.04 1 mg/kg BID | 1045 (± 265) | 8 | 16 | 56 |
| VEGF NX31838.04 10 mg/kg SID | 713 (± 206) | 6 | 16 | 70 |
| VEGF NX31838.07 10 mg/kg BID | 570 (± 273) | 6 | 16 | 76 |
| VEGF NX31838PL 10 mg/kg BID | 555 (± 174) | 8 | 16 | 76 |

% TGI = 100 (1 − $W_t/W_c$);
$W_t$ is the mean tumor volume of the treated group at time x;
$W_c$ is the mean tumor volume of the control group at time x
42% TGI or greater is significant

TABLE 10

Anti-tumor Efficacy of VEGF Nucleic Acid Ligand
(NX31838) 40K PEG in Nude Mouse Xenograph Model
% Tumor Growth Inhibition (TGI)

| Treatment | Mean Tumor Volume Mean (± SD) | # Animals | Day | % TGI |
|---|---|---|---|---|
| PBS Control | 3446 (± 1522) | 8 | 14 | 0 |
| NX31838 10 mg/kg | 540 (± 122) | 8 | 14 | 84 |
| NX31838 3 mg/kg | 795 (± 403) | 7 | 14 | 77 |
| NX31838 0.3 mg/kg | 1261 (± 337) | 8 | 14 | 63 |
| NX31838 0.03 mg/kg | 1773 (± 785) | 8 | 14 | 49 |

% TGI = 100 (1 − $W_t/W_c$);
$W_t$ is the mean tumor volume of the treated group at time x;
$W_c$ is the mean tumor volume of the control group at time x
42% TGI or greater is significant

TABLE 11

Anti-Tumor Efficacy of VEGF Nucleic Acid Ligand (NX31838)
vs Anti-VEGF MAb in a Growth Staged A673 Xenograph Model % Tumor Growth Inhibition (TGI)

| Treatment | Mean Tumor Volume Mean (± SD) | # Animals | Day | % TGI |
|---|---|---|---|---|
| PBS Control | 3082 (± 1198) | 8 | 12 | 0 |
| NX31838 10 mg/kg | 1278 (± 543) | 8 | 12 | 59 |
| Anti-VEGF Mab 100 µg Twice weekly | 959 (± 359) | 8 | 12 | 69 |

% TGI = 100 (1 − $W_t/W_c$);
$W_t$ is the mean tumor volume of the treated group at time x;
$W_c$ is the mean tumor volume of the control group at time x
42% TGI or greater is significant Tumor Growth Delay (TGD)

| Treatment | Days to 1000 mm³ | TGD ($t_t − t_c$) | Days to 2000 mm³ | TGD ($t_t − t_c$) |
|---|---|---|---|---|
| PBS Control | 6.3 | | 9.5 | |
| NX31838 10 mg/kg | 10 | 3.7 | 15.5 | 6 |
| Anti-VEGF mAb 100 µg Twice weekly | 12.3 | 6 | 18.3 | 8.8 |

TABLE 12

Automated synthesis cycle for the preparation of NX31838

| Step | Reagents | Equivalents* | Reaction Time |
|---|---|---|---|
| Detritylation | Dichloroacetic acid in $CH_2Cl_2$ (3% v/v) | 250 | 15 min |
| Coupling | Nucleoside phosphoramidite (0.2M in $CH_3CN$) | 2 | 20 min for fC & fU and 30 min for all others |
| | 1.0 M DCI | 8** | |
| Oxidation | 0.05 M $I_2$ in 2:1 pyridine:water | 5.2 | 2 |
| Capping | Cap A: 1:1:8 $Ac_2O$:2,6-lutidine:THF Cap B: 16% NMI in THF | 32 | 1 |

*Equivalents are based on the moles of CPG-bound 3'-terminal nucleoside.
**Activator equivalents are based on moles of nucleoside phosphoramidite.

General Procedure for the Synthesis of Dimers

All other phosphoramidites were coupled by the same manner as mentioned above, except the glycerol bis amidite

| Step | Reagents | Equivalents* | Reaction Time |
|---|---|---|---|
| Detritylation | Dichloroacetic acid in $CH_2Cl_2$ (3% v/v) | 250 | 15 min |
| Coupling (Coupled twice) | Nucleoside phosphoramidite (0.04M in $CH_3CN$) | 0.75 eq per coupling | 2 × 20 min |
| | 1.0 M DCI | 16** | |
| Oxidation | 0.05 M $I_2$ in 2:1 pyridine:water | 5.2 | 2 |
| Capping | Cap A: 1:1:8 $Ac_2O$:2,6-lutidine:THF Cap B: 16% NMI in THF | 32 | 1 |

We claim:

1. A method for treating a VEGF mediated disease or medical condition selected from the group consisting of cancer, psoriasis, ocular disorders characterized by excessive angiogenesis, collagen vascular diseases and rheumatoid arthritis comprising administering a pharmaceutically effective amount of a Complex comprised of a VEGF Nucleic Acid Ligand comprising 2'F-modified nucleotides and a Non-Immunogenic, High Molecular Weight Compound or a Lipophilic Compound to a patient in need of said Complex.

2. The method of claim 1 wherein said Non-Immunogenic, High Molecular Weight Compound is a Polyalkylene Glycol.

3. The method of claim 2 wherein said Polyalkylene Glycol is polyethylene glycol.

4. The method of claim 3 wherein said polyethylene glycol has a molecular weight of about between 10–80K.

5. The method of claim 3 wherein said polyethylene glycol has a molecular weight of about 20–45K.

6. The method of claim 5 wherein said Complex has the structure

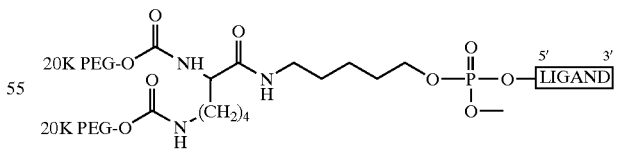

Ligand Component=fCmGmGrArAfUfCmAmGfUmG mAmAfUmGfCfUfUmAfUmAfCmAfUfCfCmG-3'3'-dT (VEGF ligand).

7. The method of claim 1 wherein said Lipophilic Compound is a glycerol lipid.

8. The method of claim 7 wherein said Complex is further associated with a lipid construct.

9. The method of claim 8 wherein said Complex has the structure

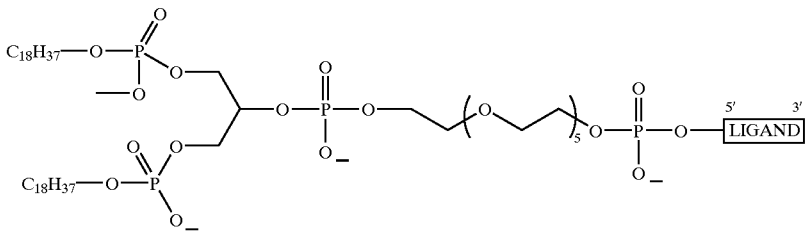

Ligand Component=fCmGmGrArAfUfCmAmGfUmGm AmAfUmGfCfUfUmAfUmAfCmAfUfCfCmG-3'3'-dT (VEGF ligand).

10. A method for improving the pharmacokinetic properties of a VEGF Nucleic Acid Ligand comprising 2'F-modified nucleotides comprising:

covalently linking said VEGF Nucleic Acid Ligand with a Non-Immunogenic, High Molecular Weight Compound or Lipophilic Compound to form a Complex comprised of a VEGF Nucleic Acid Ligand and a Non-Immunogenic, High Molecular Weight Compound or Lipophilic Compound; and administering said Complex to a patient, whereby the pharmacokinetic properties of said VEGF Nucleic Acid Ligand are improved.

11. A method for targeting a therapeutic or diagnostic agent to a specific predetermined biological target that is expressing VEGF in a patient comprising:

covalently linking said therapeutic or diagnostic agent with a Complex comprised of a VEGF Nucleic Acid Ligand comprising 2'F-modified nucleotides and a Non-Immunogenic, High Molecular Weight Compound or Lipophilic Compound, and administering said Complex to said patient, whereby said therapeutic or diagnostic agent is targeted to a specific predetermined biological target that is expressing VEGF.

12. A method of inhibiting VEGF mediated angiogenesis in a patient comprising:

covalently linking a VEGF Nucleic Acid Ligand comprising 2'F-modified nucleotides to a Non-Immunogenic, High Molecular Weight Compound or Lipophilic Compound to form a Complex, said Complex being capable of inhibiting VEGF mediated angiogenesis; and administering said Complex to said patient, whereby said VEGF mediated angiogenesis is inhibited.

13. A method of inhibiting the growth of tumors in a patient comprising:

covalently linking a VEGF Nucleic Acid Ligand comprising 2'F-modified nucleotides to a Non-Immunogenic, High Molecular Weight Compound or Lipophilic Compound to form a Complex, said Complex being capable of inhibiting the growth of tumors; and administering said Complex to said patient, whereby said growth of tumors is inhibited.

14. The method of claim 13 wherein said tumors or cells or tissues surrounding said tumors are expressing VEGF.

15. The method of claim 13 wherein said tumors or cells or tissues surrounding said tumors are expressing VEGF receptors.

16. The method of claim 15 wherein said tumors are comprised of Kaposi's sarcoma cells.

17. A method of inhibiting macular degeneration in a patient comprising:

covalently linking a VEGF Nucleic Acid Ligand comprising 2' F-modified nucleotides to a Non-Immunogenic, High Molecular Weight Compound or Lipophilic Compound to form a Complex, said Complex being capable of inhibiting macular degeneration; and administering said Complex to said patient, whereby said macular degeneration is inhibited.

18. The method of claim 17 wherein said Non-Immunogenic, High Molecular Weight Compound is a polyalkylene glycol.

19. The method of claim 18 wherein said polyalkylene glycol is polyethylene glycol.

20. The method of claim 19 wherein said polyethylene glycol has a molecular weight of about between 10–80k.

21. The method of claim 19 wherein said polyethylene glycol has a molecular weight of about between 20–45k.

22. The method of claim 21 wherein said complex has the structure

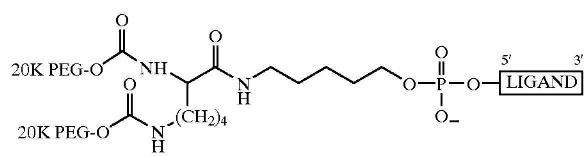

Ligand Component=fCmGmGrArAfUfCmAmGfUmGm AmAfUmGfCfUfUmAfUmAfCmAfUfCfCmG-3'3'-dT (VEGF ligand).

23. A method for prolonging the residence time of a Nucleic Acid Ligand in an ocular application comprising attaching a Non-Immunogenic, High Molecular Weight Compound to a Nucleic Acid Ligand to form a Complex, and administering said complex to the eye, whereby the residence time of said Nucleic Acid Ligand is prolonged.

* * * * *

```
                        SEQUENCE LISTING (1) GENERAL INFORMATION:

(iii) NUMBER OF SEQUENCES: 139

(2) INFORMATION FOR SEQ ID NO: 1:

(i) SEQUENCE CHARACTERISTICS:
         (A) LENGTH: 33
         (B) TYPE: nucleic acid
         (C) STRANDEDNESS: single
         (D) TOPOLOGY: linear (ii) MOLECULE TYPE: RNA (ix) FEATURE:
         (D) OTHER INFORMATION:  Nucleotides at positions 1-4 and 29-33
             are bound by a phosphorothioate bond (ix) FEATURE:
```

(D) OTHER INFORMATION: Nucleotides at positions 5, 13, 16,
                17, 20, 23-26, and 28 are 2'-OMethyl (2'-OMe) modified (ix) FEATURE:
            (D) OTHER INFORMATION: Nucleotides at positions 6-9, 12, 15,
                19, 21, 22 and 27 are 2'-amino (2'-NH2) modified (xi) SEQUENCE DESCRIPTION: SEQ ID NO: 1:

TTTTACCCUG AUGGUAGACG CCGGGGUGTT TTT                                33

(2) INFORMATION FOR SEQ ID NO: 2:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothioate bond (ix) FEATURE:
        (D) OTHER INFORMATION: Nucleotides at positions 5, 13, 16,
            17, 20, 23-26, and 28 are 2'-OMethyl (2'-OMe) modified (ix) FEATURE:
        (D) OTHER INFORMATION: Nucleotides at positions 6-9, 12, 15,
            19, 21, 22 and 27 are 2'-amino (2'-NH2) modified (xi) SEQUENCE DESCRIPTION: SEQ ID NO: 2:

TTTTACCCUG AUGGUAGACG CCGGGGUGTT TTT                                33

(2) INFORMATION FOR SEQ ID NO: 3:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothiate bond (ix) FEATURE:
        (D) OTHER INFORMATION: Nucleotides at positions 5, 8-9, 11,
            14, 16, 18, 23, 26, and 28 are 2'-OMethyl (2'OMe) modified (ix) FEATURE:
        (D) OTHER INFORMATION: Nucleotides at positions 6-7, 10, 12,
            17, 21-22, 24-25, and 27 are 2'-amino (2'-NH2) modified (xi) SEQUENCE DESCRIPTION: SEQ ID NO: 3:

TTTTGUCGGU ACGGAGUGGA CCGUCACGTT TTT                                33

(2) INFORMATION FOR SEQ ID NO: 4:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1-4 and 29-33
            are bound by a phosphorothiate bond

```
    (ix) FEATURE:
          (D) OTHER INFORMATION: Nucleotides at positions 5, 8-9, 11,
              14, 16, 18, 23, 26, and 28 are 2'-OMethyl (2'OMe) modified (ix) FEATURE:
          (D) OTHER INFORMATION: Nucleotides at positions 6-7, 10, 12,
              17, 21-22, 24-25, and 27 are 2'-amino (2'-NH2) modified (xi) SEQUENCE DESCRIPTION: SEQ ID NO: 4:

TTTTGUCGGU ACGGAGUGGA CCGUCACGTT TTT                                    33

(2) INFORMATION FOR SEQ ID NO: 5:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
          (D) OTHER INFORMATION: Nucleotides at positions 1, 6-7, 10,
              14, 16-18, 20, 22, and 24-26 are 2'-fluoro (2'-F) modified (ix) FEATURE:
          (D) OTHER INFORMATION: Nucleotides at positions 2-3, 8-9,
              11-13, 15, 19, 21, 23, and 27 are 2'-OMethyl (2'-OMe)
              modified (ix) FEATURE:
          (D) OTHER INFORMATION: T in position 28 is a 3'-3'-linked
              deoxythymidine (xi) SEQUENCE DESCRIPTION: SEQ ID NO: 5:

CGGAAUCAGU GAAUGCUUAU ACAUCCGT                                          28

(2) INFORMATION FOR SEQ ID NO: 6:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
          (D) OTHER INFORMATION: Nucleotides at positions 1, 6-7, 10,
              14, 16-18, 20, 22, and 24-26 are 2'-fluoro (2'-F) modified (ix) FEATURE:
          (D) OTHER INFORMATION: Nucleotides at positions 2-3, 8-9,
              11-13, 15, 19, 21, 23, and 27 are 2'-OMethyl (2'-OMe)
              modified (ix) FEATURE:
          (D) OTHER INFORMATION: T in position 28 is a 3'-3'-linked
              deoxythymidine (xi) SEQUENCE DESCRIPTION: SEQ ID NO: 6:

CGGAAUCAGU GAAUGCUUAU ACAUCCGT                                          28

(2) INFORMATION FOR SEQ ID NO: 7:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA
```

(ix) FEATURE:
              (D) OTHER INFORMATION: Nucleotides at positions 1, 6-7, 10,
                    14, 16-18, 20, 22, and 24-26 are 2'-fluoro (2'-F) modified (ix) FEATURE:
              (D) OTHER INFORMATION: Nucleotides at positions 2-3, 8-9,
                    11-13, 15, 19, 21, 23, and 27 are 2'-OMethyl (2'-OMe)
                    modified (ix) FEATURE:
              (D) OTHER INFORMATION: T in position 28 is a 3'-3'-linked
                    deoxythymidine (xi) SEQUENCE DESCRIPTION: SEQ ID NO: 7:

CGGAAUCAGU GAAUGCUUAU ACAUCCGT                                                  28

(2) INFORMATION FOR SEQ ID NO: 8:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: Nucleotides at positions 1, 6-7, 10,
                14, 16-18, 20, 22, and 24-26 are 2'-fluoro (2'-F) modified (ix) FEATURE:
          (D) OTHER INFORMATION: Nucleotides at positions 2-3, 8-9,
                11-13, 15, 19, 21, 23, and 27 are 2'-OMethyl (2'-OMe)
                modified (ix) FEATURE:
          (D) OTHER INFORMATION: T in position 28 is a 3'-3'-linked
                deoxythymidine (xi) SEQUENCE DESCRIPTION: SEQ ID NO: 8:

CGGAAUCAGU GAAUGCUUAU ACAUCCGT                                                  28

(2) INFORMATION FOR SEQ ID NO: 9:

(i) SEQUENCE CHARACTERISTICS:
          (A) LENGTH: 28
          (B) TYPE: nucleic acid
          (C) STRANDEDNESS: single
          (D) TOPOLOGY: linear (ii) MOLECULE TYPE: RNA (ix) FEATURE:
          (D) OTHER INFORMATION: Nucleotides at positions 1, 6-7, 10,
                14, 16-18, 20, 22, and 24-26 are 2'-fluoro (2'-F) modified (ix) FEATURE:
          (D) OTHER INFORMATION: Nucleotides at positions 2-3, 8-9,
                11-13, 15, 19, 21, 23, and 27 are 2'-OMethyl (2'-OMe)
                modified (ix) FEATURE:
          (D) OTHER INFORMATION: T in position 28 is a 3'-3'-linked
                deoxythymidine (xi) SEQUENCE DESCRIPTION: SEQ ID NO: 9:

CGGAAUCAGU GAAUGCUUAU ACAUCCGT                                                  28

(2) INFORMATION FOR SEQ ID NO: 10:

(i) SEQUENCE CHARACTERISTICS:
          (A) LENGTH: 28

(B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  Nucleotides at positions 1, 6-7, 10,
            14, 16-18, 20, 22, and 24-26 are 2'-fluoro (2'-F) modified (ix) FEATURE:
        (D) OTHER INFORMATION:  Nucleotides at positions 2-3, 8-9,
            11-13, 15, 19, 21, 23, and 27 are 2'-OMethyl (2'-OMe)
            modified (ix) FEATURE:
        (D) OTHER INFORMATION:  T in position 28 is a 3'-3'-linked
            deoxythymidine (xi) SEQUENCE DESCRIPTION: SEQ ID NO: 10:

CGGAAUCAGU GAAUGCUUAU ACAUCCGT                                              28

(2) INFORMATION FOR SEQ ID NO: 11:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  Nucleotides at positions 1, 6-7, 10,
            14, 16-18, 20, 22, and 24-26 are 2'-fluoro (2'-F) modified (ix) FEATURE:
        (D) OTHER INFORMATION:  Nucleotides at positions 2-3, 8-9,
            11-13, 15, 19, 21, 23, and 27 are 2'-OMethyl (2'-OMe)
            modified (ix) FEATURE:
        (D) OTHER INFORMATION:  T in position 28 is a 3'-3'-linked
            deoxythymidine (xi) SEQUENCE DESCRIPTION: SEQ ID NO: 11:

CGGAAUCAGU GAAUGCUUAU ACAUCCGT                                              28

(2) INFORMATION FOR SEQ ID NO: 12:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  Nucleotides at positions 1, 6-7, 10,
            14, 16-18, 20, 22, and 24-26 are 2'-fluoro (2'-F) modified (ix) FEATURE:
        (D) OTHER INFORMATION:  Nucleotides at positions 2-3, 8-9,
            11-13, 15, 19, 21, 23, and 27 are 2'-OMethyl (2'-OMe)
            modified (ix) FEATURE:
        (D) OTHER INFORMATION:  T in position 28 is a 3'-3'-linked
            deoxythymidine (xi) SEQUENCE DESCRIPTION: SEQ ID NO: 12:

CGGAAUCAGU GAAUGCUUAU ACAUCCGT                                              28

(2) INFORMATION FOR SEQ ID NO: 13:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: Nucleotides at positions 1, 3-4, 6,
           8-9, 14-16, 18, 20, 24, and 26 are 2'-fluoro (2'-F)
           modified (ix) FEATURE:
        (D) OTHER INFORMATION: Nucleotides at positions 5, 7, 10,
           12-13, 17, 19, 21-23, 25, and 27 are 2'-OMethyl (2'-OMe)
           modified (ix) FEATURE:
        (D) OTHER INFORMATION: T at position 28 is a 3'-3'-linked
           deoxythymidine (xi) SEQUENCE DESCRIPTION: SEQ ID NO: 13:

CAUUACACCG AAGUUUACGU GAGUAUGT                        28

(2) INFORMATION FOR SEQ ID NO: 14:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
           modified (xi) SEQUENCE DESCRIPTION: SEQ ID NO: 14:

GGGAGGACGA UGCGGNNNNN NNNNNNNNNN NNNNNNNNNN NNNNNCAGAC      50

GACUCGCCCG A                                               61

(2) INFORMATION FOR SEQ ID NO: 15:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
           modified (xi) SEQUENCE DESCRIPTION: SEQ ID NO: 15:

GGGAGGACGA UGCGGAAGAA UUGGUCAUCG UCGUCCCGC CUCCCCAGAC       50

GACUCGCCCG A                                               61

(2) INFORMATION FOR SEQ ID NO: 16:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 16:

GGGAGGACGA UGCGGAAUAC GGAAGAAUUG GAUACAUAUG CUCGUCAGAC           50

GACUCGCCCG A                                                    61

(2) INFORMATION FOR SEQ ID NO: 17:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 17:

GGGAGGACGA UGCGGGAUAA CAGAAGAAUU GGUGAACAAC GUGGUCAGAC           50

GACUCGCCCG A                                                    61

(2) INFORMATION FOR SEQ ID NO: 18:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 18:

GGGAGGACGA UGCGGAUGAU CGCGUAGGAA GUAUUGGAAG GCCCUCAGAC           50

GACUCGCCCG A                                                    61

(2) INFORMATION FOR SEQ ID NO: 19:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 19:

GGGAGGACGA UGCGGCACUU UAGAAGAAUU GAAUUUCCCG CUGGUCAGAC           50

GACUCGCCCG A                                                    61

(2) INFORMATION FOR SEQ ID NO: 20:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 20:

GGGAGGACGA UGCGGUAGGA AGAAUUGGAA GCGCAUUUUC CUCGYCAGAC          50

GACUCGCCCG A                                                   61

(2) INFORMATION FOR SEQ ID NO: 21:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 21:

GGGAGGACGA UGCGGCGGGA UUUUGGAAGA AUUGGAUAUU GGCCUCAGAC          50

GACUCGCCCG A                                                   61

(2) INFORMATION FOR SEQ ID NO: 22:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 22:

GGGAGGACGA UGCGGCGGYA CUUUGGAAGA AUUGAAUUUC CCGCUCAGAC          50

GACUCGCCCG A                                                   61

(2) INFORMATION FOR SEQ ID NO: 23:

(i) SEQUENCE CHARACTERISTICS:
            (A) LENGTH: 61
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-fluoro (2'-F)
                modified (xi) SEQUENCE DESCRIPTION: SEQ ID NO: 23:

GGGAGGACGA UGCGGAAGAA UUGGAUAUAU CGUUCACCCC CACCUCAGAC          50

```
GACUCGCCCG A                                                    61

(2) INFORMATION FOR SEQ ID NO: 24:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 24:

GGGAGGACGA UGCGGAAACG GAAGAAUUGG AUACGCAAGC ACGUUCAGAC            50

GACUCGCCCG A                                                    61

(2) INFORMATION FOR SEQ ID NO: 25:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 25:

GGGAGGACGA UGCGGUAGGA AGUAUUGUAA GCGCCUCGUU UUCGCCAGAC            50

GACUCGCCCG A                                                    61

(2) INFORMATION FOR SEQ ID NO: 26:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 26:

GGGAGGACGA UGCGGAGUUU UGGAAGAAUU GGAUGUUCCG AUCGUCAGAC            50

GACUCGCCCG A                                                    61

(2) INFORMATION FOR SEQ ID NO: 27:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified
```

(xi) SEQUENCE DESCRIPTION: SEQ ID NO: 27:

GGGAGGACGA UGCGGAAGAA ACGGAAGAAU UGGAGACACG CUCGUCAGAC         50

GACUCGCCCG A                                                  61

(2) INFORMATION FOR SEQ ID NO: 28:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 28:

GGGAGGACGA UGCGGGAAGA AUUGAUGUUG UAUUGUCCUU CCGAUUUCCU         50

GCCGUCAGAC GACUCGCCCG A                                       71

(2) INFORMATION FOR SEQ ID NO: 29:

(i) SEQUENCE CHARACTERISTICS:
        (A) LENGTH: 70
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 29:

GGGAGGACGA UGCGGACAGA AGAAUUGGGC UUCGCAUUAU CCUCUGUCAG         50

CCGCCAGACG ACUCGCCCGA                                         70

(2) INFORMATION FOR SEQ ID NO: 30:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 30:

GGGAGGACGA UGCGGUGAGA GAAACGGAAG AAUUGGAUAC GAUACUCAUC         50

GCGCUCAGAC GACUCGCCCG A                                       71

(2) INFORMATION FOR SEQ ID NO: 31:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
                  (D) OTHER INFORMATION:  All pyrimidines are 2'-fluoro (2'-F)
                      modified (xi) SEQUENCE DESCRIPTION: SEQ ID NO: 31:

GGGAGGACGA UGCGGCUUAA GUUUUGGAAG AAUUGAAUAC UGGGUCAGAC        50

GACUCGCCCG A                                                  61

(2) INFORMATION FOR SEQ ID NO: 32:

(i) SEQUENCE CHARACTERISTICS:
                  (A) LENGTH: 60
                  (B) TYPE: nucleic acid
                  (C) STRANDEDNESS: single
                  (D) TOPOLOGY: linear (ii) MOLECULE TYPE: RNA (ix) FEATURE:
                  (D) OTHER INFORMATION:  All pyrimidines are 2'-fluoro (2'-F)
                      modified (xi) SEQUENCE DESCRIPTION: SEQ ID NO: 32:

GGGAGGACGA UGCGGUAACC AGUGGAAGAA UUGGCUGCUA UCCUCAGACG        50

ACUCGCCCGA                                                    60

(2) INFORMATION FOR SEQ ID NO: 33:

(i) SEQUENCE CHARACTERISTICS:
                  (A) LENGTH: 60
                  (B) TYPE: nucleic acid
                  (C) STRANDEDNESS: single
                  (D) TOPOLOGY: linear (ii) MOLECULE TYPE: RNA (ix) FEATURE:
                  (D) OTHER INFORMATION:  All pyrimidines are 2'-fluoro (2'-F)
                      modified (xi) SEQUENCE DESCRIPTION: SEQ ID NO: 33:

GGGAGGACGA UGCGGAACGG AAGAAUUGGA UACGUAGCAU GCGUCAGACG        50

ACUCGCCCGA                                                    60

(2) INFORMATION FOR SEQ ID NO: 34:

(i) SEQUENCE CHARACTERISTICS:
                  (A) LENGTH: 61
                  (B) TYPE: nucleic acid
                  (C) STRANDEDNESS: single
                  (D) TOPOLOGY: linear (ii) MOLECULE TYPE: RNA (ix) FEATURE:
                  (D) OTHER INFORMATION:  All pyrimidines are 2'-fluoro (2'-F)
                      modified (xi) SEQUENCE DESCRIPTION: SEQ ID NO: 34:

GGGAGGACGA UGCGGCAGGA UUUUGGAAGA AUUGGAUAUU GGCCGCAGAC        50

GACUCGCCCG A                                                  61

(2) INFORMATION FOR SEQ ID NO: 35:

(i) SEQUENCE CHARACTERISTICS:

(A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 35:

GGGAGGACGA UGCGGAAACG GAAGAAUUGG AUACCGCUAC GUGUUCAGAC         50

GACUCGCCCG A                                                  61

(2) INFORMATION FOR SEQ ID NO: 36

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 36

GGGAGGACGA UGCGGAAGAA UUGAGCAUUC CUUCUCCUUG UGCCUCAGAC         50

GACUCGCCCG A                                                  61

(2) INFORMATION FOR SEQ ID NO: 37:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 37:

GGGAGGACGA UGCGGAGCUA ACGGAAGAAU UGGAAACAAC CGCGUCAGAC         50

GACUCGCCCG A                                                  61

(2) INFORMATION FOR SEQ ID NO: 38:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 38:

GGGAGGACGA UGCGGYGAAC CGAUGGAAUU UUUGGACGCU CGCCUCAGAC         50

GACUCGCCCG A                                                  61

(2) INFORMATION FOR SEQ ID NO: 39:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 39:

GGGAGGACGA UGCGGAYCAA CCGAUUGACG UUAUGGGACG CUGGUCAGAC          50

GACUCGCCCG A                                                   61

(2) INFORMATION FOR SEQ ID NO: 40:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 40:

GGGAGGACGA UGCGGUAACC GAUUGAACUU CUUGGACGCU ACCGUCAGAC          50

GACUCGCCCG A                                                   61

(2) INFORMATION FOR SEQ ID NO: 41:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 41:

GGGAGGACGA UGCGGUAACC GAAUUGAAGU UAUUGGACGC UACCUCAGAC          50

GACUCGCCCG A                                                   61

(2) INFORMATION FOR SEQ ID NO: 42:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 42:

GGGAGGACGA UGCGGGAGCA GAACCGAUAG AAGAAUUGGA CGCUCAGCUC          50

CGGGUCAGAC GACUCGCCCG A                                        71

(2) INFORMATION FOR SEQ ID NO: 43:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 43:

GGGAGGACGA UGCGGGUACC AGAAUGAGCA ACCGAAUGAA GAACUGGACG          50

CUGCUCAGAC GACUCGCCCG A                                        71

(2) INFORMATION FOR SEQ ID NO: 44:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 44:

GGGAGGACGA UGCGGUGAAC CGAUGGAAUC GCUUGGACGC UCAUCGCACG          50

UUGCUCAGAC GACUCGCCCG A                                        71

(2) INFORMATION FOR SEQ ID NO: 45:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 45:

GGGAGGACGA UGCGGUCAAC CGGUUGAAUA UUUGGUCGCU GACCUCAGAC          50

GACUCGCCCG A                                                   61

(2) INFORMATION FOR SEQ ID NO: 46:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All pyrimidines are 2'-fluoro (2'-F)
        modified (xi) SEQUENCE DESCRIPTION: SEQ ID NO: 46:

GGGAGGACGA UGCGGAACUA GUGAAUGCUU AUACGACCGU GUUGUCAGAC          50

GACUCGCCCG A                                                    61

(2) INFORMATION FOR SEQ ID NO: 47:

(i) SEQUENCE CHARACTERISTICS:
        (A) LENGTH: 60
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 47:

GGGAGGACGA UGCGGAUCAG UGAAUGCUUA UAGACCGCCU CCGUCAGACG          50

ACUCGCCCGA                                                      60

(2) INFORMATION FOR SEQ ID NO: 48:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 48:

GGGAGGACGA UGCGGAGAAU CAGUGAAUGC UUAUAAAUCU CGYGUCAGAC          50

GACUCGCCCG A                                                    61

(2) INFORMATION FOR SEQ ID NO: 49:

(i) SEQUENCE CHARACTERISTICS:
        (A) LENGTH: 62
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 49:

GGGAGGACGA UGCGGAAUCA GUGAAUGCUU AUAGCUCCCG CGUCCUCAGA          50

CGACUCGCCC GA                                                   62

(2) INFORMATION FOR SEQ ID NO: 50:

(i) SEQUENCE CHARACTERISTICS:
        (A) LENGTH: 60

```
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 50:

GGGAGGACGA UGCGGAACCA GUGAAUGCUU AUAAGACUGC UCGUCAGACG         50

ACUCGCCCGA                                                    60

(2) INFORMATION FOR SEQ ID NO: 51:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 51:

GGGAGGACGA UGCGGAUCAG UGAAUGCUUA UAGACCGUAU UGCGUCAGAC         50

GACUCGCCCG A                                                  61

(2) INFORMATION FOR SEQ ID NO: 52:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 52:

GGGAGGACGA UGCGGAGAAU CAGUGAAUGC UUAUAAACCU CGUGUCAGAC         50

GACUCGCCCG A                                                  61

(2) INFORMATION FOR SEQ ID NO: 53:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 53:

GGGAGGACGA UGCGGAAUCA GUGAAUGCUU AUAGCUCCGC GUGGUCAGAC         50

GACUCGCCCG A                                                  61
```

(2) INFORMATION FOR SEQ ID NO: 54:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 54:

```
GGGAGGACGA UGCGGACCAG UGAAUGCUUA UAAGCCCAUC GACCUCAGAC          50

GACUCGCCCG A                                                    61
```

(2) INFORMATION FOR SEQ ID NO: 55:

(i) SEQUENCE CHARACTERISTICS:
        (A) LENGTH: 60
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 55:

```
GGGAGGACGA UGCGGCAGGG UGAAUGCCAA UGUACUUUUC GCGUCAGACG          50

ACUCGCCCGA                                                      60
```

(2) INFORMATION FOR SEQ ID NO: 56:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 56:

```
GGGAGGACGA UGCGGAAUCA GUGAAUGCUU AUAGCUCCAC GUCGUCAGAC          50

GACUCGCCCG A                                                    61
```

(2) INFORMATION FOR SEQ ID NO: 57:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 57:

GGGAGGACGA UGCGGAAUCA GUGAAUGCUU AUACAUCCGC UCGGUCAGAC        50

GACUCGCCCG A                                                  61

(2) INFORMATION FOR SEQ ID NO: 58:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 58:

GGGAGGACGA UGCGGGACUA GGUGAAUGCC AAUAUUCUUC UCCGUCAGAC        50

GACUCGCCCG A                                                  61

(2) INFORMATION FOR SEQ ID NO: 59:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 30 is a 3'-3'-linked
            deoxythymidine (xi) SEQUENCE DESCRIPTION: SEQ ID NO: 59:

GACGAUGCGG UAGGAAGAAU UGGAAGCGCN                              30

(2) INFORMATION FOR SEQ ID NO: 60:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 60:

GACGAUGCGG UAGGAAGAAU UGGAAGCG                                28

(2) INFORMATION FOR SEQ ID NO: 61:

(i) SEQUENCE CHARACTERISTICS:
        (A) LENGTH: 28
        (B) TYPE: nucleic acid
        (C) STRANDEDNESS: single
        (D) TOPOLOGY: linear (ii) MOLECULE TYPE: RNA (ix) FEATURE:
              (D) OTHER INFORMATION: All pyrimidines are 2'-fluoro (2'-F)
                   modified (ix) FEATURE:
              (D) OTHER INFORMATION: C in position 28 is 2'-OH C (xi) SEQUENCE DESCRIPTION: SEQ ID NO: 61:

ACGAUGCGGU AGGAAGAAUU GGAAGCGC                                              28

(2) INFORMATION FOR SEQ ID NO: 62:

(i) SEQUENCE CHARACTERISTICS:
              (A) LENGTH: 23
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-fluoro (2'-F)
                   modified (ix) FEATURE:
              (D) OTHER INFORMATION: C in position 23 is 2'-OH C (xi) SEQUENCE DESCRIPTION: SEQ ID NO: 62:

GCGGUAGGAA GAAUUGGAAG CGC                                                   23

(2) INFORMATION FOR SEQ ID NO: 63:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-fluoro (2'-F)
                   modified (ix) FEATURE:
              (D) OTHER INFORMATION: C in position 22 is 2'-OH C (xi) SEQUENCE DESCRIPTION: SEQ ID NO: 63:

CGGUAGGAAG AAUUGGAAGC GC                                                    22

(2) INFORMATION FOR SEQ ID NO: 64:

(i) SEQUENCE CHARACTERISTICS:
              (A) LENGTH: 22
              (B) TYPE: nucleic acid
              (C) STRANDEDNESS: single
              (D) TOPOLOGY: linear (ii) MOLECULE TYPE: RNA (ix) FEATURE:
              (D) OTHER INFORMATION: All pyrimidines are 2'-fluoro (2'-F)
                   modified (ix) FEATURE:
              (D) OTHER INFORMATION: N at position 22 is a 3'-3'-linked
                   deoxythymidine (xi) SEQUENCE DESCRIPTION: SEQ ID NO: 64:

GGUAGGAAGA AUUGGAAGCG CN                                                    22

(2) INFORMATION FOR SEQ ID NO: 65:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (ix) FEATURE:
        (D) OTHER INFORMATION: N at position 21 is a 3'-3'-linked
            deoxythymidine (xi) SEQUENCE DESCRIPTION: SEQ ID NO: 65:

GUAGGAAGAA UUGGAAGCGCN                                              21

(2) INFORMATION FOR SEQ ID NO: 66:

(i) SEQUENCE CHARACTERISTICS:
        (A) LENGTH: 32
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (ix) FEATURE:
        (D) OTHER INFORMATION: N at position 32 is a 3'-3'-linked
            deoxythymidine (xi) SEQUENCE DESCRIPTION: SEQ ID NO: 66:

GGCGAACCGA UGGAAUUUUU GGACGCUCGC CN                                 32

(2) INFORMATION FOR SEQ ID NO: 67:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (ix) FEATURE:
        (D) OTHER INFORMATION: C in position 29 is 2'-OH C (xi) SEQUENCE DESCRIPTION: SEQ ID NO: 67:

GCGAACCGAU GGAAUUUUUG GACGCUCGC                                     29

(2) INFORMATION FOR SEQ ID NO: 68:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: RNA (ix) FEATURE:

```
        (D) OTHER INFORMATION:  All pyrimidines are 2'-fluoro (2'-F)
            modified (xi) SEQUENCE DESCRIPTION: SEQ ID NO: 68:

CGAACCGAUG GAAUUUUUGG ACGCUCG                                          27

(2) INFORMATION FOR SEQ ID NO: 69:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 26 is a 3'-3'-linked
            deoxythymidine (xi) SEQUENCE DESCRIPTION: SEQ ID NO: 69:

GAACCGAUGG AAUUUUGGA CGCUCN                                            26

(2) INFORMATION FOR SEQ ID NO: 70:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 24 is a 3'-3'-linked
            deoxythymidine (xi) SEQUENCE DESCRIPTION: SEQ ID NO: 70:

AACCGAUGGA AUUUUGGAC GCUN                                              24

(2) INFORMATION FOR SEQ ID NO: 71:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 22 is a 3'-3'-linked
            deoxythymidine (xi) SEQUENCE DESCRIPTION: SEQ ID NO: 71:

ACCGAUGGAA UUUUUGGACG CN                                               22

(2) INFORMATION FOR SEQ ID NO: 72:
```

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 30 is a 3'-3'-linked
            deoxythymidine (xi) SEQUENCE DESCRIPTION: SEQ ID NO: 72:

GCGGAAUCAG UGAAUGCUUA UACAUCCGCN                                          30

(2) INFORMATION FOR SEQ ID NO: 73:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 73:

CGGAAUCAGU GAAUGCUUAU ACAUCCG                                             27

(2) INFORMATION FOR SEQ ID NO: 74:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  C in position 25 is 2'-OH C (xi) SEQUENCE DESCRIPTION: SEQ ID NO: 74:

GGAAUCAGUG AAUGCUUAUA CAUCC                                               25

(2) INFORMATION FOR SEQ ID NO: 75:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 24 is a 3'-3'-linked
            deoxythymidine (xi) SEQUENCE DESCRIPTION: SEQ ID NO: 75:

GAAUCAGUGA AUGCUUAUAC AUCN                                              24

(2) INFORMATION FOR SEQ ID NO: 76:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 22 is a 3'-3'-linked
            deoxythymidine (xi) SEQUENCE DESCRIPTION: SEQ ID NO: 76:

AAUCAGUGAA UGCUUAUACA UN                                                22

(2) INFORMATION FOR SEQ ID NO: 77:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  N at position 20 is a 3'-3'-linked
            deoxythymidine (xi) SEQUENCE DESCRIPTION: SEQ ID NO: 77:

AUCAGUGAAU GCUUAUACAN                                                   20

(2) INFORMATION FOR SEQ ID NO: 78:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:
        (D) OTHER INFORMATION:  G in position 10, A in position 12,
            and G in position 22 are unmodified (i.e., 2'-OH)

(xi) SEQUENCE DESCRIPTION: SEQ ID NO: 78:

GACGAUGCGG UAGGAAGAAU UGGAAGCGC                                         29

(2) INFORMATION FOR SEQ ID NO: 79:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (ix) FEATURE:
        (D) OTHER INFORMATION: Purines are 2'-OMethyl (2'-OMe)
            modified (ix) FEATURE:
        (D) OTHER INFORMATION: G in position 10 and A in position 12
            are unmodified (i.e., 2'-OH)

(xi) SEQUENCE DESCRIPTION: SEQ ID NO: 79:

GACGAUGCGG UAGGAAGAAU UGGAAGCGC                                       29

(2) INFORMATION FOR SEQ ID NO: 80:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (ix) FEATURE:
        (D) OTHER INFORMATION: Purines are 2'-OMethyl (2'-OMe)
            modified (ix) FEATURE:
        (D) OTHER INFORMATION: G in positions 10 and 22 is unmodified
            (i.e., 2'-OH)

(xi) SEQUENCE DESCRIPTION: SEQ ID NO: 80:

GACGAUGCGG UAGGAAGAAU UGGAAGCGC                                       29

(2) INFORMATION FOR SEQ ID NO: 81:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (ix) FEATURE:
        (D) OTHER INFORMATION: Purines are 2'-OMethyl (2'-OMe)
            modified (ix) FEATURE:
        (D) OTHER INFORMATION: A in position 12 and G in position 22
            are unmodified (i.e., 2'-OH)

(xi) SEQUENCE DESCRIPTION: SEQ ID NO: 81:

GACGAUGCGG UAGGAAGAAU UGGAAGCGC                                       29

(2) INFORMATION FOR SEQ ID NO: 82:

(i) SEQUENCE CHARACTERISTICS:
        (A) LENGTH: 31
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
           modified (ix) FEATURE:
        (D) OTHER INFORMATION: Purines are 2'-OMethyl (2'-OMe)
           modified (ix) FEATURE:
        (D) OTHER INFORMATION: A in position 6 and G in position 21
           are unmodified (i.e., 2'-OH)

(xi) SEQUENCE DESCRIPTION: SEQ ID NO: 82:

GGCGAACCGA UGGAAUUUUU GGACGCUCGC C                          31

(2) INFORMATION FOR SEQ ID NO: 83:

(i) SEQUENCE CHARACTERISTICS:
        (A) LENGTH: 31
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
           modified (ix) FEATURE:
        (D) OTHER INFORMATION: Purines are 2'-OMethyl (2'-OMe)
           modified (ix) FEATURE:
        (D) OTHER INFORMATION: A in position 6 is unmodified
           (i.e., 2'- OH)

(xi) SEQUENCE DESCRIPTION: SEQ ID NO: 83:

GGCGAACCGA UGGAAUUUUU GGACGCUCGC C                          31

(2) INFORMATION FOR SEQ ID NO: 84:

(i) SEQUENCE CHARACTERISTICS:
        (A) LENGTH: 31
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
           modified (ix) FEATURE:
        (D) OTHER INFORMATION: Purines are 2'-OMethyl (2'-OMe)
           modified (ix) FEATURE:
        (D) OTHER INFORMATION: G in position 21 is unmodified
           (i.e., 2'- OH)

(xi) SEQUENCE DESCRIPTION: SEQ ID NO: 84:

GGCGAACCGA UGGAAUUUUU GGACGCUCGC C                                    31

(2) INFORMATION FOR SEQ ID NO: 85:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:
        (D) OTHER INFORMATION:  A in positions 5 and 6 is unmodified
            (i.e., 2'-OH)

(xi) SEQUENCE DESCRIPTION: SEQ ID NO: 85:

GCGGAAUCAG UGAAUGCUUA UACAUCCGC                                       29

(2) INFORMATION FOR SEQ ID NO: 86:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:
        (D) OTHER INFORMATION:  A in position 5 is unmodified
            (i.e., 2'- OH)

(xi) SEQUENCE DESCRIPTION: SEQ ID NO: 86:

GCGGAAUCAG UGAAUGCUUA UACAUCCGC                                       29

(2) INFORMATION FOR SEQ ID NO: 87:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:
        (D) OTHER INFORMATION:  A in position 6 is unmodified
            (i.e., 2'- OH)

(xi) SEQUENCE DESCRIPTION: SEQ ID NO: 87:

GCGGAAUCAG UGAAUGCUUA UACAUCCGC                                    29

(2) INFORMATION FOR SEQ ID NO: 88:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:
        (D) OTHER INFORMATION:  G in position 4 and A in position 6
            are unmodified (i.e., 2'-OH)

(xi) SEQUENCE DESCRIPTION: SEQ ID NO: 88:

GCGGUAGGAA GAAUUGGAAG CGC                                          23

(2) INFORMATION FOR SEQ ID NO: 89:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:
        (D) OTHER INFORMATION:  A in position 5 and G in position 20
            are unmodified (i.e., 2'-OH)

(xi) SEQUENCE DESCRIPTION: SEQ ID NO: 89:

GCGAACCGAU GGAAUUUUUG GACGCUCGC                                    29

(2) INFORMATION FOR SEQ ID NO: 90:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (ix) FEATURE:
        (D) OTHER INFORMATION:  Purines are 2'-OMethyl (2'-OMe)
            modified (ix) FEATURE:

(D) OTHER INFORMATION: A in positions 4 and 5 is unmodified
            (i.e., 2'-OH)

(xi) SEQUENCE DESCRIPTION: SEQ ID NO: 90:

CGGAAUCAGU GAAUGCUUAU ACAUCCG                                            27

(2) INFORMATION FOR SEQ ID NO: 91:

(i) SEQUENCE CHARACTERISTICS:
        (A) LENGTH: 60
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 91:

GGGAGGACGA UGCGGUCUUU GAGUUUUUGC CAACGGUUUU CGCUCAGACG                    50

ACUCGCCCGA                                                               60

(2) INFORMATION FOR SEQ ID NO: 92:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 92:

GGGAGGACGA UGCGGAACGG AAUUCUUGGA UACACACCUC GUCCUCAGAC                    50

GACUCGCCCG A                                                             61

(2) INFORMATION FOR SEQ ID NO: 93:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 93:

GGGAGGACGA UGCGGUCAGG AACGGAAUUU UUGGAGACAC GCCCUCAGAC                    50

GACUCGCCCG A                                                             61

(2) INFORMATION FOR SEQ ID NO: 94:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
             (D) OTHER INFORMATION: All pyrimidines are 2'-fluoro (2'-F)
                 modified (xi) SEQUENCE DESCRIPTION: SEQ ID NO: 94:

GGGAGGACGA UGCGGACUGG GAGAAUCCGA AAAACCUUCA CGCGUCAGAC         50

GACUCGCCCG A                                                  61

(2) INFORMATION FOR SEQ ID NO: 95:

(i) SEQUENCE CHARACTERISTICS:
             (A) LENGTH: 61
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-fluoro (2'-F)
                 modified (xi) SEQUENCE DESCRIPTION: SEQ ID NO: 95:

GGGAGGACGA UGCGGAUCCA UCAUUUAACC GUUUGCUCUC CCCCUCAGAC         50

GACUCGCCCG A                                                  61

(2) INFORMATION FOR SEQ ID NO: 96:

(i) SEQUENCE CHARACTERISTICS:
             (A) LENGTH: 61
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-fluoro (2'-F)
                 modified (xi) SEQUENCE DESCRIPTION: SEQ ID NO: 96:

GGGAGGACGA UGCGGUUGAU CGGACGUUAG UCAUUCCCG AUCGUCAGAC          50

GACUCGCCCG A                                                  61

(2) INFORMATION FOR SEQ ID NO: 97:

(i) SEQUENCE CHARACTERISTICS:
             (A) LENGTH: 61
             (B) TYPE: nucleic acid
             (C) STRANDEDNESS: single
             (D) TOPOLOGY: linear (ii) MOLECULE TYPE: RNA (ix) FEATURE:
             (D) OTHER INFORMATION: All pyrimidines are 2'-fluoro (2'-F)
                 modified (xi) SEQUENCE DESCRIPTION: SEQ ID NO: 97:

GGGAGGACGA UGCGGGAGCU UGAAGUUUCA GUAUUGGCAC AACCUCAGAC         50

GACUCGCCCG A                                                  61

(2) INFORMATION FOR SEQ ID NO: 98:

(i) SEQUENCE CHARACTERISTICS:

(A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 98:

GGGAGGACGA UGCGGCGCCA CUUUGGAAGU UAUUGAAUUU CGCGUCAGAC         50

GACUCGCCCG A                                                   61

(2) INFORMATION FOR SEQ ID NO: 99:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 99:

GGGAGGACGA UGCGGUGAAU GAGCUGACGA CCCUGAAUUG CUCGUCAGAC         50

GACUCGCCCG A                                                   61

(2) INFORMATION FOR SEQ ID NO: 100:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 100:

GGGAGGACGA UGCGGGAGCU UGAAGUUUCG GUAUUGGCAC AACCUCAGAC         50

GACUCGCCCG A                                                   61

(2) INFORMATION FOR SEQ ID NO: 101:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 101:

GGGAGGACGA UGCGGCAACU AUUCGUUGAU GUUUCCGUGA GCCGUCAGAC         50

GACUCGCCCG A                                                   61

(2) INFORMATION FOR SEQ ID NO: 102:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 102:

GGGAGGACGA UGCGGGAGCU UGAAGUUUCA GUACUGGCAC AACCUCAGAC          50

GACUCGCCCG A                                                   61

(2) INFORMATION FOR SEQ ID NO: 103:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 103:

GGGAGGACGA UGCGGAACCA AUAGAGAUCU UCGGCUGCCC CGCGUCAGAC          50

GACUCGCCCG A                                                   61

(2) INFORMATION FOR SEQ ID NO: 104:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 104:

GGGAGGACGA UGCGGAAAAC GCUUUUCUUG GCCCCCUCGU UGCGCCAGAC          50

GACUCGCCCG A                                                   61

(2) INFORMATION FOR SEQ ID NO: 105:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 105:

GGGAGGACGA UGCGGUUAAC GGAAUUCUUG GAUACAUAGC AUGGUCAGAC     50

GACUCGCCCG A     61

(2) INFORMATION FOR SEQ ID NO: 106:

(i) SEQUENCE CHARACTERISTICS:
        (A) LENGTH: 70
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 106:

GGGAGGACGA UGCGGCAAAG UUUGAGUUGA UCUGAUACGU UUCAGUAUUG     50

GCGUCAGACG ACUCGCCCGA     70

(2) INFORMATION FOR SEQ ID NO: 107:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 107:

GGGAGGACGA UGCGGAUCUG UGAACUGGGU UUUUGCCGAC GGUUACGCUU     50

UUGCUCAGAC GACUCGCCCG A     71

(2) INFORMATION FOR SEQ ID NO: 108:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 108:

GGGAGGACGA UGCGGCAAAA GUUUGAGUUG AUCUGAUACG UUUCAGUAUU     50

GGCGUCAGAC GACUCGCCCG A     71

(2) INFORMATION FOR SEQ ID NO: 109:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
    (D) OTHER INFORMATION: All pyrimidines are 2'-fluoro (2'-F)
        modified (xi) SEQUENCE DESCRIPTION: SEQ ID NO: 109:

GGGAGGACGA UGCGGUUGAU CGAGGUUCUA AAGCCUAUUU CCUGACUUUC    50

UCCCCCAGAC GACUCGCCCG A    71

(2) INFORMATION FOR SEQ ID NO: 110:

(i) SEQUENCE CHARACTERISTICS:
        (A) LENGTH: 70
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 110:

GGGAGGACGA UGCGGAUCUG UGAACUGGGU UUUGCCGACG GUUACGCUUU    50

UGCUCAGACG ACUCGCCCGA    70

(2) INFORMATION FOR SEQ ID NO: 111:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 111:

GGGAGGACGA UGCGGAAGGA AGAUGUUGAU CGUUUGACGU GAUGUGGAUC    50

CGCGUCAGAC GACUCGCCCG A    71

(2) INFORMATION FOR SEQ ID NO: 112:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 112:

GGGAGGACGA UGCGGUAGUA AGUUAUUGAA AGCGCAUCUC UAUCAACUCU    50

CGGCCCAGAC GACUCGCCCG A    71

(2) INFORMATION FOR SEQ ID NO: 113:

(i) SEQUENCE CHARACTERISTICS:
        (A) LENGTH: 71

```
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
             modified (xi) SEQUENCE DESCRIPTION: SEQ ID NO: 113:

GGGAGGACGA UGCGGUACUU UCUUCUUUCU UUGCCUUUCU UUUUCUUUUA          50

CGCCUCAGAC GACUCGCCCG A                                         71

(2) INFORMATION FOR SEQ ID NO: 114:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
             modified (xi) SEQUENCE DESCRIPTION: SEQ ID NO: 114:

GGGAGGACGA UGCGGCAGUU AAUUAAUUUG AGUUGUGAUG UGUGUCGUUA          50

UGGGUCAGAC GACUCGCCCG A                                         71

(2) INFORMATION FOR SEQ ID NO: 115:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
             modified (xi) SEQUENCE DESCRIPTION: SEQ ID NO: 115:

GGGAGGACGA UGCGGGAUGC UGAGUGAGGA AGUCUGAUUG UUGCAGUAUU          50

GGCGUCAGAC GACUCGCCCG A                                         71

(2) INFORMATION FOR SEQ ID NO: 116:

(i) SEQUENCE CHARACTERISTICS:
        (A) LENGTH: 70
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
             modified (xi) SEQUENCE DESCRIPTION: SEQ ID NO: 116:

GGGAGGACGA UGCGGAAUGG AAUUUGAGUC GAUCUAGAAU GCGUCGUAUG          50

GGCUCAGACG ACUCGCCCGA                                           70
```

(2) INFORMATION FOR SEQ ID NO: 117:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 117:

GGGAGGACGA UGCGGACUCA ACUGGACGCU AUGUUGACGG UUAUCGCUUU      50

UGGGUCAGAC GACUCGCCCG A      71

(2) INFORMATION FOR SEQ ID NO: 118:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 118:

GGGAGGACGA UGCGGCAGGU UCAGAAUUGG CAGUCGCAUU GAUCUUUUUC      50

ACCGCCAGAC GACUCGCCCG A      71

(2) INFORMATION FOR SEQ ID NO: 119:

(i) SEQUENCE CHARACTERISTICS:
        (A) LENGTH: 72
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 119:

GGGAGGACGA UGCGGCAAAA GUUUGAGUUG AUCUGAUACG UUUCCAGUAU      50

UGGCGUCAGA CGACUCGCCC GA      72

(2) INFORMATION FOR SEQ ID NO: 120:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 120:

GGGAGGACGA UGCGGCAGUU AAUUAACUUG AGUUGUGAUG UGUGUCGUUA        50

UGGGUCAGAC GACUCGCCCG A                                       71

(2) INFORMATION FOR SEQ ID NO: 121:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 121:

GGGAGGACGA UGCGGCAAAU UCAAGGUCGA GUUAUGCGUA GAUGUGGCUC        50

CUGUGCAGAC GACUCGCCCG A                                       71

(2) INFORMATION FOR SEQ ID NO: 122:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 122:

GGGAGGACGA UGCGGAUCUG UUGAACUGGG UUUUGCCGAC GGUUACGCUU        50

UUGCUCAGAC GACUCGCCCG A                                       71

(2) INFORMATION FOR SEQ ID NO: 123:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  All pyrimidines are 2'-fluoro (2'-F)
            modified (xi) SEQUENCE DESCRIPTION: SEQ ID NO: 123:

GGGAGGACGA UGCGGCAGUU AAUUAAUUUG AGUUGUGAUG UGUGUCGUUA        50

UGGGCCAGAC GACUCGCCCG A                                       71

(2) INFORMATION FOR SEQ ID NO: 124:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 124:

GGGAGGACGA UGCGGUUGAU CGAUUUCCU GGCGUCCUUA UGGGUCAGAC        50

GACUCGCCCG A                                                61

(2) INFORMATION FOR SEQ ID NO: 125:

(i) SEQUENCE CHARACTERISTICS:
        (A) LENGTH: 60
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 125:

GGGAGGACGA UGCGGUCUUU GGGUUUUUGC CAACGGUUUU CGCUCAGACG        50

ACUCGCCCGA                                                  60

(2) INFORMATION FOR SEQ ID NO: 126:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 126:

GGGAGGACGA UGCGGUUCAG AAUUGGCUGC GAUCCUUUUC CCCCUCAGAC        50

GACUCGCCCG A                                                61

(2) INFORMATION FOR SEQ ID NO: 127:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 127:

GGGAGGACGA UGCGGUUGAU CGACUUUCC UGAUCUUCUC CUCCUCAGAC        50

GACUCGCCCG A                                                61

(2) INFORMATION FOR SEQ ID NO: 128:

(i) SEQUENCE CHARACTERISTICS:
        (A) LENGTH: 61
        (B) TYPE: nucleic acid

```
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 128:

GGGAGGACGA UGCGGCACUA GGUGCAUGCC AUGAAAUCUU GCUGUCAGAC          50

GACUCGCCCG A                                                   61

(2) INFORMATION FOR SEQ ID NO: 129:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 129:

GGGAGGACGA UGCGGGAUCA CGGCUUUGCA CGAUCUUCUU CUCCUCAGAC          50

GACUCGCCCG A                                                   61

(2) INFORMATION FOR SEQ ID NO: 130:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 130:

GGGAGGACGA UGCGGGAUCA CGAUACUUGA CGAUUUUCCU CUCCUCAGAC          50

GACUCGCCCG A                                                   61

(2) INFORMATION FOR SEQ ID NO: 131:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 131:

GGGAGGACGA UGCGGAGCGG UAUUCUGUUC GGUCGUUUUC CUCCUCAGAC          50

GACUCGCCCG A                                                   61
```

(2) INFORMATION FOR SEQ ID NO: 132:

(i) SEQUENCE CHARACTERISTICS:
        (A) LENGTH: 61
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-fluoro (2'-F)
            modified (xi) SEQUENCE DESCRIPTION: SEQ ID NO: 132:

GGGAGGACGA UGCGGAUUUG GAUGCAUGUC AAGGCGUUUU GCCCUCAGAC           50

GACUCGCCCG A                                                    61

(2) INFORMATION FOR SEQ ID NO: 133:

(i) SEQUENCE CHARACTERISTICS:
        (A) LENGTH: 78
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 133:

TAATACGACT CACTATAGGG AGGACGATGC GGNNNNNNNN NNNNNNNNNN           50

NNNNNNNNNN NNCAGACGAC TCGCCCGA                                  78

(2) INFORMATION FOR SEQ ID NO: 134:

(i) SEQUENCE CHARACTERISTICS:
        (A) LENGTH: 88
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 134:

TAATACGACT CACTATAGGG AGGACGATGC GGNNNNNNNN NNNNNNNNNN           50

NNNNNNNNNN NNNNNNNNNN NNCAGACGAC TCGCCCGA                       88

(2) INFORMATION FOR SEQ ID NO: 135:

(i) SEQUENCE CHARACTERISTICS:
        (A) LENGTH: 16
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 135:

TCGGGCGAGT CGTCTG                                               16

(2) INFORMATION FOR SEQ ID NO: 136:

(i) SEQUENCE CHARACTERISTICS:
        (A) LENGTH: 32
        (B) TYPE: nucleic acid
        (C) STRANDEDNESS: single
        (D) TOPOLOGY: linear (ii) MOLECULE TYPE: DNA

```
        (xi) SEQUENCE DESCRIPTION: SEQ ID NO: 136:

TAATACGACT CACTATAGGG AGGACGATGC GG                                    32

(2) INFORMATION FOR SEQ ID NO: 137:

(i) SEQUENCE CHARACTERISTICS:
        (A) LENGTH: 13
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 137:

GCCTTAGTCA CTT                                                         13

(2) INFORMATION FOR SEQ ID NO: 138:

(i) SEQUENCE CHARACTERISTICS:
        (A) LENGTH: 14
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 138:

CGGATGTATA AGCA                                                        14

(2) INFORMATION FOR SEQ ID NO: 139:

(i) SEQUENCE CHARACTERISTICS:
        (A) LENGTH: 71
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:   All pyrimidines are 2'-fluoro (2'-F)
             modified (xi) SEQUENCE DESCRIPTION: SEQ ID NO: 139:

GGGAGGACGA UGCGGNNNNN NNNNNNNNNN NNNNNNNNNN NNNNNNNNNN                 50

NNNNNCAGAC GACUCGCCCG A                                                71
```